United States Patent
Shen et al.

(10) Patent No.: US 10,925,264 B2
(45) Date of Patent: Feb. 23, 2021

(54) GENETICALLY MODIFIED NON-HUMAN ANIMAL WITH HUMAN OR CHIMERIC LAG-3

(71) Applicant: Biocytogen Pharmaceuticals (Beijing) Co., Ltd, Beijing (CN)

(72) Inventors: Yuelei Shen, Beijing (CN); Yanan Guo, Beijing (CN); Chaoshe Guo, Beijing (CN); Yang Bai, Beijing (CN); Jiawei Yao, Beijing (CN); Lei Zhao, Beijing (CN); Rui Huang, Beijing (CN)

(73) Assignee: Biocytogen Pharmaceuticals (Beijing) Co., Ltd, Beijing (CN)

( * ) Notice: Subject to any disclaimer, the term of this patent is extended or adjusted under 35 U.S.C. 154(b) by 0 days.

(21) Appl. No.: 16/409,683

(22) Filed: May 10, 2019

(65) Prior Publication Data

US 2019/0364860 A1 Dec. 5, 2019

Related U.S. Application Data

(63) Continuation of application No. PCT/CN2017/110435, filed on Nov. 10, 2017.

(30) Foreign Application Priority Data

Nov. 11, 2016 (CN) .......................... 201610993414.8
Jun. 9, 2017 (CN) .......................... 201710431882.0
Nov. 10, 2017 (CN) .......................... 201711103773.2

(51) Int. Cl.
| | | |
|---|---|---|
| *A01K 67/027* | (2006.01) | |
| *A61K 49/00* | (2006.01) | |
| *C07K 14/705* | (2006.01) | |
| *C12N 15/11* | (2006.01) | |
| *C12N 15/85* | (2006.01) | |
| *C12N 15/89* | (2006.01) | |

(52) U.S. Cl.
CPC ...... *A01K 67/0278* (2013.01); *A61K 49/0008* (2013.01); *C07K 14/70503* (2013.01); *C12N 15/11* (2013.01); *C12N 15/8509* (2013.01); *A01K 2207/15* (2013.01); *A01K 2217/072* (2013.01); *A01K 2227/105* (2013.01); *A01K 2267/0331* (2013.01); *C07K 2319/03* (2013.01); *C12N 15/89* (2013.01); *C12N 2310/20* (2017.05); *C12N 2800/107* (2013.01); *C12N 2810/10* (2013.01)

(58) Field of Classification Search
USPC .......................... 800/13, 18, 3; 435/455, 463
See application file for complete search history.

(56) References Cited

U.S. PATENT DOCUMENTS

| | | | |
|---|---|---|---|
| 4,683,195 A | 7/1987 | Mullis et al. | |
| 10,306,874 B2 * | 6/2019 | Mujica | ............... A01K 67/0278 |
| 2015/0106961 A1 | 4/2015 | Rojas et al. | |
| 2017/0142943 A1 * | 5/2017 | Mujica | ............... A01K 67/0278 |

FOREIGN PATENT DOCUMENTS

| | | |
|---|---|---|
| CN | 104561095 | 4/2015 |
| WO | WO2004078928 | 9/2004 |
| WO | WO2017087780 | 5/2017 |
| WO | WO2018001241 | 1/2018 |
| WO | WO2018041119 | 3/2018 |
| WO | WO2018041120 | 3/2018 |
| WO | WO2018041121 | 3/2018 |
| WO | WO2018068756 | 4/2018 |
| WO | WO2018041118 | 3/2019 |

OTHER PUBLICATIONS

Auerbach et al., "Establishment and Chimera Analysis of 129/SvEv- and C57BL/6-Derived Mouse Embryonic Stem Cell Lines," BioTechniques, 2000, 29:1024-1032.
Burova et al., "Combined treatment with anti-LAG-3 and anti-PD-1 fully human monoclonal antibodies inhibits tumor growth and immunocompetent double humanized LAG-3/PD-1 mice," Cancer Research, 2016, 76(14):1484, abstract.
Burugu et al., "Emerging targets in cancer immunotherapy." Seminars in Cancer Biology. Academic Press, 2017, 52(2):39-52.
Festing et al., "Revised nomenclature for strain 129 mice," Mammalian Genome, 1999, 10(8):836.
GenBank accession: NP_032506, "Laminin subunit alpha-1 precursor [Mus musculus]," Mar. 19, 2019, 9 pages.
Hemon et al. "MHC class II engagement by its ligand LAG-3 (CD223) contributes to melanoma resistance to apoptosis." The Journal of Immunology, 2011, 186(9):5173-5183.
International Search Report and Written Opinion in Appln. No. PCT/CN2017/110435, dated Feb. 9, 2018, 14 pages.
Joller et al., "Tim-3, Lag-3, and TIGIT," Curr. Top Microbiol. Immunol., 2017, 410:127-156.
Workman et al., "The CD4-related molecule, LAG-3 (CD223), regulates the expansionof activated T cells," European journal of immunology, 2003, 33(4):970-979.
Huard et al., "Characterization of the major histocompatibility complex class II binding site on LAG-3 protein," Proc. Natl. Acad. Sci. USA, 1997, 94:5744-5749.
GenBank Accession No. X51985.3, "Human LAG-3 mRNA for CD4-related protein involved in lymphocyte activation," GenBank, Feb. 26, 1990, 4 pages.
GenBank accession No. NM_008479.2, "Mus musculus lymphocyte-activation gene 3 (Lag3), mRNA," May 2, 2019, 5 pages.

* cited by examiner

*Primary Examiner* — Anne Marie S Wehbe
(74) *Attorney, Agent, or Firm* — Fish & Richardson P.C.

(57) ABSTRACT

The present disclosure relates to the genetically modified non-human animals that express a human or chimeric (e.g., humanized) Lymphocyte Activation Gene 3 (LAG-3), and methods of use thereof.

12 Claims, 23 Drawing Sheets

Specification includes a Sequence Listing.

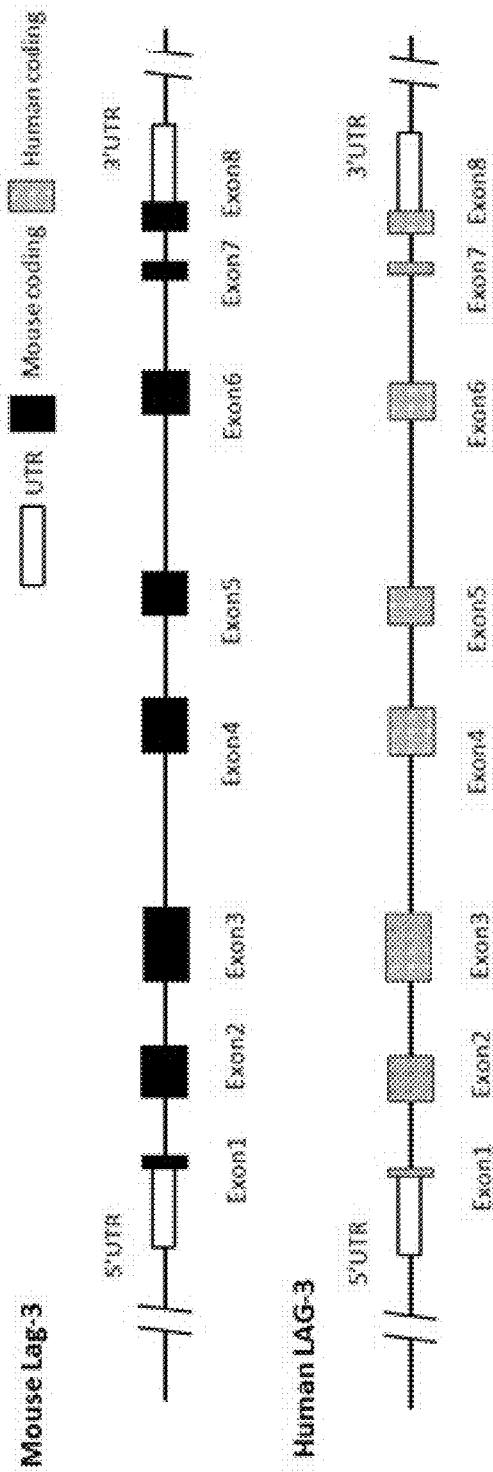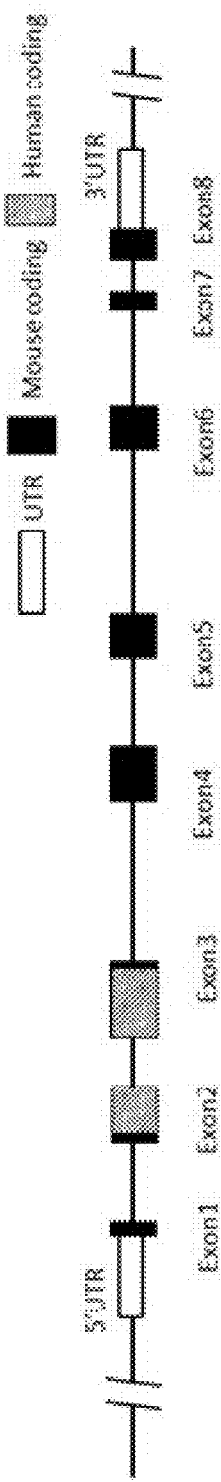
FIG. 3A
FIG. 3B

FIG. 21

```
        Score      Expect    Method                              Identities       Positives        Gaps
    613 bits(1580) 0.0()     Compositional matrix adjust.        344/499(69%)     369/499(73%)     8/499(1%)

Mouse   1   MREDLLLGFLLLGLLWEAPVVSSGPGKELPVVWAQEGAPVHLPCSLKSPNLDPNFLRRGG   60
            M E   LG L L  LW APV     PG E+PVVWAQEGAP  LPCS   P  D + LRR G
Human   1   MWEAQFLGLLFLQPLWVAPVKPLQPGAEVPVVWAQEGAPAQLPCSPTIPLQDLSLLRRAG   60

Mouse  61   VIWQHQPDSGQPTPIPALDL-----HQGMPSPRQPAPGRYTVLSVAPGGLRSGRQPLHPHV   116
            V WQHQPDSG P    P  L      H    PS   P P RYTVLSV PGGLRSGR PL P V
Human  61   VTWQHQPDSGPPAAAPGHPLAPGPHPAAPSSWGPRPRPRYTVLSVGPGGLRSGRLPLQPRV   120

Mouse 117   QLEERGLQRGDFSLMLRPALRTDAGEYHATVRLPNRALSCSLRLRVGQASMIASPSGVLK   176
            QL+ERG  QRGDFSLMLRPA R DAGEY A V L  +RALSC  LRLR+GQASM ASP G L+
Human 121   QLDERGRQRGDFSLMLRPARRADAGEYRAAVHLRDRALSCRLRLRLGQASMTASPPGSLR   180

Mouse 177   LSDWVLLNCSFSRPDRPVSVHWFQ---GQNRVPVYNSPRHFLAETFLLLPQVSPLDSGTWG   234
            SDWV+LNCSFSRPDRP SVHWF+    GQ RVPV   SP H  LAE+FL LPQVSP+DSG WG
Human 181   ASDWVILNCSFSRPDRPASVHWFRNRGQGRVPVRESPHHHLAESFLFLPQVSPMDSGPWG   240

Mouse 235   CVLTYRDGFNVSITYNLKVLIGLEPVAPLTVYAAEEGSRVELPCHLPPGVGTPSLLIAKWTP   294
            C+LTYRDGFNVSI  YNL VLGLEP  PLTVYA  GSRV LPC LP GVGT  S L  AKWTP
Human 241   CILTYRDGFNVSIMYNLTVLGLEPPTPLTVYAGAGSRVGLPCRLPAGVGTRSFLTAKWTP   300

Mouse 295   PGGGPELPVAGKSGNFTLHLEAVGLAQAGTYTCSIHLQGQQLNATVTLAVITVTPKSFGL   354
            PGGGP+L  V G  +G+FTL LE V  AQAGTYTC  IHLQ  QLNATVTLA+ITVTPKSFG
Human 301   PGGGPDLLVTGDNGDFTLRLEDVSQAQAGTYTCHIHLQEQQLNATVTLAIITVTPKSFGS   360

Mouse 355   PGSRGKLLCEVTPASGKERFVWRPLNNLS-RSCPGPVLEIQEARLLAERWCQLYEGQRL   413
            PGS GKLLCEVTP SG+ERFVW  L+ S  RS  GP LE  QEA+LL++ WQCQLY+G+RL
Human 361   PGSLGKLLCEVTPVSGQERFVWSSLDTPSQRSFSGPWLEAQEAQLLSQPWQCQLYQGERL   420

Mouse 414   LGATVYAAE-SSSGAHSARRISGDLKGGHLVLVLILGALSLFLLIVAGAFGFHWWRKQLLL   472
            LGA VY  E  SS GA  + R  G L  GHL+L  LILG LSL LIV GAFGFH  WR+Q
Human 421   LGAAVYFTELSSPGAQRSGRAPGALPAGHLLLFLILGVLSLLLLVTGAFGFHLWRRQWRP   480

Mouse 473   RRFSALEHGIQPFPAQRKI   491
            RRFSALE GI P   AQ KI
Human 481   RRFSALEQGIHPFQAQSKI   499
```

GENETICALLY MODIFIED NON-HUMAN ANIMAL WITH HUMAN OR CHIMERIC LAG-3

CLAIM OF PRIORITY

This application claims benefit of PCT/CN2017/110435, which further claims the benefit of Chinese Patent Application App. No. 201610993414.8, filed on Nov. 11, 2016, and Chinese Patent Application App. No. 201710431882.0, filed on Jun. 9, 2017, and Chinese Patent Application App. No. 201711103773.2, filed on Nov. 10, 2017. The entire contents of the foregoing are incorporated herein by reference.

TECHNICAL FIELD

This disclosure relates to genetically modified animal expressing human or chimeric (e.g., humanized) Lymphocyte Activation Gene 3 (LAG-3), and methods of use thereof.

BACKGROUND

The immune system has developed multiple mechanisms to prevent deleterious activation of T cells. One such mechanism is the intricate balance between positive and negative costimulatory signals delivered to T cells. Targeting the inhibitory pathways for the immune system is considered to be a potential approach for the treatment of various diseases, e.g., cancers, and autoimmune diseases.

The traditional drug research and development for these inhibitory receptors typically use in vitro screening approaches. However, these screening approaches cannot provide the body environment (such as tumor microenvironment, stromal cells, extracellular matrix components and immune cell interaction, etc.), resulting in a higher rate of failure in drug development. In addition, in view of the differences between humans and animals, the test results obtained from the use of conventional experimental animals for in vivo pharmacological test may not be able to reflect the real disease state and the identification and interaction at the targeting sites, resulting in that the results in many clinical trials are significantly different from the animal experimental results. Therefore, the development of humanized animal models that are suitable for human antibody screening and evaluation will significantly improve the efficiency of new drug development and reduce the costs for drug research and development.

SUMMARY

This disclosure is related to an animal model with humanized LAG-3. The animal model can express human LAG-3 or chimeric LAG-3 (e.g., humanized LAG-3) protein in its body. It can be used in the studies on the function of LAG-3 gene, and can be used in the screening and evaluation of anti-human LAG-3 antibodies. In addition, the animal models prepared by the methods described herein can be used in drug screening, pharmacodynamics studies, treatments for immune-related diseases (e.g., autoimmune disease), and cancer therapy for human LAG-3 target sites; in addition, they can be used to facilitate the development and design of new drugs, and save time and cost. In summary, this disclosure provides a powerful tool for studying the function of LAG-3 protein and screening for cancer drugs.

Furthermore, the disclosure also provides LAG-3 gene knockout mice. Moreover, the mice described in the present disclosure can be mated with the mice containing other human or chimeric genes (e.g., chimeric CTLA-4, chimeric PD-1, or other immunomodulatory factors), so as to obtain a mouse expressing two or more human or chimeric proteins. The mice can also, e.g., be used for screening antibodies in the case of a combined use of drugs, as well as evaluating the efficacy of the combination therapy.

In one aspect, the disclosure relates to genetically-modified, non-human animals whose genome comprises at least one chromosome comprising a sequence encoding a human or chimeric Lymphocyte Activation Gene 3 (LAG-3). In some embodiments, the sequence encoding the human or chimeric LAG-3 is operably linked to an endogenous regulatory element at the endogenous LAG-3 gene locus in the at least one chromosome. In some embodiments, the sequence encoding a human or chimeric LAG-3 comprises a sequence encoding an amino acid sequence that is at least 50%, 55%, 65%, 70%, 75%, 80%, 85%, 90%, 95%, 99%, or 100% identical to human LAG-3 (NP 002277.4 (SEQ ID NO: 27)). In some embodiments, the sequence encoding a human or chimeric LAG-3 comprises a sequence encoding an amino acid sequence that is at least 50%, 55%, 65%, 70%, 75%, 80%, 85%, 90%, 95%, 99%, or 100% identical to SEQ ID NO: 31. In some embodiments, the sequence encoding a human or chimeric LAG-3 comprises a sequence encoding an amino acid sequence that corresponds to amino acids 25-166 of SEQ ID NO: 27.

In some embodiments, the animal is a mammal, e.g., a monkey, a rodent or a mouse. In some embodiments, the animal is a C57BL/6 mouse. In some embodiments, the animal does not express endogenous LAG-3. In some embodiments, the animal has one or more cells expressing human or chimeric LAG-3. In some embodiments, the animal has one or more cells expressing human or chimeric LAG-3, and the expressed human or chimeric LAG-3 can bind to or interact with human protein MHC II (Major Histocompatibility Complex Class II), human CD3, human L-selectin or human galectin-3. In some embodiments, the animal has one or more cells expressing human or chimeric LAG-3, and the expressed human or chimeric LAG-3 can bind to or interact with endogenous MHC II, endogenous CD3, endogenous L-selectin or endogenous galectin-3.

In one aspect, the disclosure relates to genetically-modified, non-human animals, wherein the genome of the animals comprises a replacement, at an endogenous LAG-3 gene locus, of a sequence encoding a region of endogenous LAG-3 with a sequence encoding a corresponding region of human LAG-3. In some embodiments, the sequence encoding the corresponding region of human LAG-3 is operably linked to an endogenous regulatory element at the endogenous LAG-3 locus, and one or more cells of the animal expresses a chimeric LAG-3. In some embodiments, the animal does not express endogenous LAG-3. In some embodiments, the region of endogenous LAG-3 is the extracellular region of LAG-3. In some embodiments, the animal has one or more cells expressing a chimeric LAG-3 having an extracellular region, a transmembrane region, and a cytoplasmic region, wherein the extracellular region comprises a sequence that is at least 50%, 60%, 70%, 80%, 90%, 95%, or 99% identical to the extracellular region of human LAG-3. In some embodiments, the extracellular region of the chimeric LAG-3 has a sequence that has at least 10, 20, 30, 40, 50, 60, 70, 80, 90, 100, 110, 120, 130, 140, 150, or 160 contiguous amino acids that are identical to a contiguous sequence present in the extracellular region of human LAG-3. In some embodiments, the animal is a mouse, and the sequence encoding the region of endogenous LAG-3 is exon 1, exon 2, exon 3, exon 4, exon 5, exon 6, exon 7 and/or exon 8 of the endogenous mouse LAG-3 gene (e.g., exon 2, exon 3, or part of exon 2 and exon 3). In some embodiments, the animal is heterozygous with respect to the replacement at the endogenous LAG-3 gene locus. In some embodiments, the animal is homozygous with respect to the replacement at the endogenous LAG-3 gene locus.

In one aspect, the disclosure relates to methods for making a genetically-modified, non-human animal, including: replacing in at least one cell of the animal, at an endogenous LAG-3 gene locus, a sequence encoding a region of an endogenous LAG-3 with a sequence encoding a corresponding region of human LAG-3. In some embodiments, the sequence encoding the corresponding region of human LAG-3 comprises exon 1, exon 2, exon 3, exon 4, exon 5, exon 6, exon 7 and/or exon 8 of a human LAG-3 gene. In some embodiments, the sequence encoding the corresponding region of LAG-3 comprises exon 2 and exon 3 of a human LAG-3 gene, and/or a part of exon 2 and/or exon 3 of a human LAG-3 gene. In some embodiments, the sequence encoding the corresponding region of human LAG-3 encodes amino acids 25-166 of SEQ ID NO: 27. In some embodiments, the region is located within the extracellular region of LAG-3. In some embodiments, the animal is a mouse, and the sequence encoding the region of the endogenous LAG-3 locus is exon 2 and exon 3 of mouse LAG-3 gene.

In one aspect, the disclosure relates to non-human animals comprising at least one cell comprising a nucleotide sequence encoding a chimeric LAG-3 polypeptide, wherein the chimeric LAG-3 polypeptide comprises at least 50 contiguous amino acid residues that are identical to the corresponding contiguous amino acid sequence of a human LAG-3, wherein the animal expresses the chimeric LAG-3. In some embodiments, the chimeric LAG-3 polypeptide has at least 50, 60, 70, 80, 90, 100, 110, 120, 130, 140, 150, or 160 contiguous amino acid residues that are identical to the corresponding contiguous amino acid sequence of a human LAG-3 extracellular region. In some embodiments, the chimeric LAG-3 polypeptide comprises a sequence that is at least 90%, 95%, or 99% identical to amino acids 25-166 of SEQ ID NO: 27. In some embodiments, the nucleotide sequence is operably linked to an endogenous LAG-3 regulatory element of the animal. In some embodiments, the chimeric LAG-3 polypeptide comprises an endogenous LAG-3 transmembrane region and/or an endogenous LAG-3 cytoplasmic region. In some embodiments, the nucleotide sequence is integrated to an endogenous LAG-3 gene locus of the animal. In some embodiments, the chimeric LAG-3 has at least one mouse LAG-3 activity (e.g., interacting with mouse MHC II, inhibiting mouse T-cell immune responses, binding to mouse CD3, L-selectin or galectin-3) and/or at least one human LAG-3 activity (e.g., interacting with human MHC II, inhibiting human T-cell immune responses, binding to human CD3, L-selectin or galectin-3).

In one aspect, the disclosure relates to methods of making a genetically-modified mouse cell that expresses a chimeric LAG-3, the method including: replacing, at an endogenous mouse LAG-3 gene locus, a nucleotide sequence encoding a region of mouse LAG-3 with a nucleotide sequence encoding a corresponding region of human LAG-3, thereby generating a genetically-modified mouse cell that includes a nucleotide sequence that encodes the chimeric LAG-3, wherein the mouse cell expresses the chimeric LAG-3. In some embodiments, the chimeric LAG-3 comprises an extracellular region of mouse LAG-3 comprising a mouse signal peptide sequence, an extracellular region of human LAG-3, a transmembrane and/or a cytoplasmic region of a mouse LAG-3. In some embodiments, the nucleotide sequence encoding the chimeric LAG-3 is operably linked to an endogenous LAG-3 regulatory region, e.g., promoter.

In some embodiments, the animals further comprise a sequence encoding an additional human or chimeric protein. In some embodiments, the additional human or chimeric protein is programmed cell death protein 1 (PD-1), cytotoxic T-lymphocyte-associated protein 4 (CTLA-4), T-cell immunoglobulin and mucin-domain containing-3 (TIM-3), B And T Lymphocyte Associated (BTLA), Programmed Cell Death 1 Ligand 1 (PD-L1), TNF Receptor Superfamily Member 9 (4-1BB), CD27, CD28, CD47, T-Cell Immunoreceptor With Ig And ITIM Domains (TIGIT), CD27, Glucocorticoid-Induced TNFR-Related Protein (GITR), or TNF Receptor Superfamily Member 4 (TNFRSF4 or OX40). In some embodiments, the animal or mouse further comprises a sequence encoding an additional human or chimeric protein. In some embodiments, the additional human or chimeric protein is programmed cell death protein 1 (PD-1), CTLA-4, TIM-3, BTLA, PD-L1, 4-1BB, CD27, CD28, CD47, TIGIT, CD27, GITR, or OX40.

In one aspect, the disclosure relates to methods of determining effectiveness of an anti-LAG-3 antibody for the treatment of cancer, including: administering the anti-LAG-3 antibody to the animal as described herein, wherein the animal has a tumor, and determining the inhibitory effects of the anti-LAG-3 antibody to the tumor. In some embodiments, the animal comprises one or more cells (e.g., tumor cells, antigen presenting cells, dendritic cells, mononuclear phagocytes, endothelial cells, thymic epithelial cells, and B cells) that express MHC II, CD3, L-selectin or galectin-3.

In some embodiments, the tumor comprises one or more cancer cells that are injected into the animal. In some embodiments, determining the inhibitory effects of the anti-LAG-3 antibody to the tumor involves measuring the tumor volume in the animal. In some embodiments, the tumor cells are melanoma cells, non-small cell lung carcinoma (NSCLC) cells, small cell lung cancer (SCLC) cells, bladder cancer cells, breast cancer cells, and/or prostate cancer cells (e.g., metastatic hormone-refractory prostate cancer).

In one aspect, the disclosure relates to methods of determining effectiveness of an anti-LAG-3 antibody for the treatment of various immune-related disorders, e.g., autoimmune diseases (e.g., psoriasis).

In one aspect, the disclosure relates to methods of determining effectiveness of an anti-LAG-3 antibody and an additional therapeutic agent for the treatment of a tumor, including administering the anti-LAG-3 antibody and the additional therapeutic agent to the animal as described herein, wherein the animal has a tumor, and determining the inhibitory effects on the tumor. In some embodiments, the animal further comprises a sequence encoding a human or chimeric programmed cell death protein 1 (PD-1) or cytotoxic T-lymphocyte-associated protein 4 (CTLA-4). In some embodiments, the additional therapeutic agent is an anti-PD-1 antibody. In some embodiments, the additional therapeutic agent is an anti-CTLA-4 antibody. In some embodiments, the animal comprises one or more cells (e.g., tumor cells, antigen presenting cells, dendritic cells, mononuclear phagocytes, endothelial cells, thymic epithelial cells, and B cells) that express MHC II, CD3, L-selectin or galectin-3. In some embodiments, the tumor comprises one or more tumor cells that express PD-L1 or PD-L2. In some embodiments, the tumor comprises one or more tumor cells that express CD80 or CD86. In some embodiments, the tumor is caused by injection of one or more cancer cells into the animal. In some embodiments, determining the inhibitory effects of the treatment involves measuring the tumor volume in the animal. In some embodiments, the tumor comprises melanoma cells, non-small cell lung carcinoma (NSCLC) cells, small cell lung cancer (SCLC) cells, bladder cancer cells, breast cancer cells, and/or prostate cancer cells (e.g., metastatic hormone-refractory prostate cancer cells).

In one aspect, the disclosure relates to proteins comprising an amino acid sequence, wherein the amino acid sequence is one of the following: (a) an amino acid sequence set forth in SEQ ID NO: 31; (b) an amino acid sequence that is at least 90% identical to SEQ ID NO: 31; (c) an amino acid sequence that is at least 91%, 92%, 93%, 94%, 95%, 96%, 97%, 98%, or 99% identical to SEQ ID NO: 31; (d) an amino acid sequence that is different from the amino acid sequence set forth in SEQ ID NO: 31 by no more than 10, 9, 8, 7, 6, 5, 4, 3, 2 or 1 amino acid; and (e) an amino acid sequence that comprises a substitution, a deletion and/or insertion of one, two, three, four, five or more amino acids to the amino acid sequence set forth in SEQ ID NO: 31. In some embodiments, provided herein are cells comprising the proteins disclosed herein. In some embodiments, provided herein are animals having the proteins disclosed herein.

In one aspect, the disclosure relates to nucleic acids comprising a nucleotide sequence, wherein the nucleotide sequence is one of the following: (a) a sequence that encodes the protein as described herein; (b) SEQ ID NO: 29; (c) SEQ ID NO: 30; (d) a sequence that is at least 90% identical to SEQ ID NO: 29 or SEQ ID NO: 30; (e) a sequence that is at least 91%, 92%, 93%, 94%, 95%, 96%, 97%, 98%, or 99% identical to SEQ ID NO: 29; and (f) a sequence that is at least 91%, 92%, 93%, 94%, 95%, 96%, 97%, 98%, or 99% identical to SEQ ID NO: 30. In some embodiments, provided herein are cells comprising the nucleic acids disclosed herein. In some embodiments, provided herein are animals having the nucleic acids disclosed herein.

In one aspect, the disclosure relates to a targeting vector, including a) a DNA fragment homologous to the 5' end of a region to be altered (5' arm), which is selected from the LAG-3 gene genomic DNAs in the length of 100 to 10,000 nucleotides; b) a desired/donor DNA sequence encoding a donor region; and c) a second DNA fragment homologous to the 3' end of the region to be altered (3' arm), which is selected from the LAG-3 gene genomic DNAs in the length of 100 to 10,000 nucleotides.

In some embodiments, a) the DNA fragment homologous to the 5' end of a region to be altered (5' arm/receptor) is selected from the nucleotide sequences that have at least 90% homology to the NCBI accession number NC_000072.6; c) the DNA fragment homologous to the 3' end of the region to be altered (3' arm/receptor) is selected from the nucleotide sequences that have at least 90% homology to the NCBI accession number NC_000072.6.

In some embodiments, a) the DNA fragment homologous to the 5' end of a region to be altered (5' arm/receptor) is selected from the nucleotides from the position 124911766 to the position 124910898 of the NCBI accession number NC_000072.6; c) the DNA fragment homologous to the 3' end of the region to be altered (3' arm/receptor) is selected from the nucleotides from the position 124910116 to the position 124908702 of the NCBI accession number NC_000072.6.

In some embodiments, a length of the selected genomic nucleotide sequence is about 1.2 kb, 1.5 kb or 1 kb. In some embodiments, the length is about 869 bp or 1415 bp. In some embodiments, the region to be altered is exon 2, exon 3, and/or part of exon 2 and exon 3 of LAG-3 gene.

In some embodiments, the sequence of the 5' arm is shown in SEQ ID NO: 32. In some embodiments, the sequence of the 3' arm is shown in SEQ ID NO: 38.

In some embodiments, the targeting vector further includes a selectable gene marker.

In some embodiments, the target region is derived from human. In some embodiments, the target region is a part or entirety of the nucleotide sequence of a humanized LAG-3. In some embodiments, the nucleotide sequence is shown as one or more of the first exon, the second exon, the third exon, the fourth exon, the fifth exon, the sixth exon, the seventh exon, and the eighth exon of the DNA sequence of the human LAG-3.

In some embodiments, the nucleotide sequence of the human LAG-3 encodes the human LAG-3 protein with the NCBI accession number NP 002277.4 (SEQ ID NO: 27).

The disclosure also relates to a cell including the targeting vector as described herein.

In another aspect, the disclosure relates to an sgRNA sequence for constructing a humanized animal model, wherein the sgRNA sequence targets the LAG-3 gene, the sgRNA is unique on the target sequence of the LAG-3 gene to be altered, and meets the sequence arrangement rule of 5'-NNN (20)-NGG3' or 5'-CCN-N (20)-3'. In some embodiments, the targeting site of the sgRNA in the mouse LAG-3 gene is located on exon 2 or exon 3 of the mouse LAG-3 gene.

In another aspect, the disclosure relates to an sgRNA sequence for constructing a humanized animal model, wherein an upstream sequence thereof is shown as SEQ ID NO: 15, and a downstream sequence thereof is shown as SEQ ID NO: 17, and the sgRNA sequence recognizes a 5' targeting site.

The disclosure also relates to an sgRNA sequence for constructing a humanized animal model, wherein an upstream sequence thereof is shown as SEQ ID NO: 16, which is obtained by adding TAGG to the 5' end of SEQ ID NO: 15; a downstream sequence thereof is shown as SEQ ID NO: 18, which is obtained by adding AAAC to the 5' end of SEQ ID NO: 17, and the sgRNA sequence recognizes a 5' targeting site.

The disclosure also relates to an sgRNA sequence for constructing a humanized animal model, wherein an upstream sequence thereof is shown as SEQ ID NO: 19, and a downstream sequence thereof is shown as SEQ ID NO: 21, and the sgRNA sequence recognizes a 3' targeting site.

The disclosure further relates to an sgRNA sequence for constructing a humanized animal model, wherein an upstream sequence thereof is shown as SEQ ID NO: 20, which is obtained by adding TAGG to the 5' end of SEQ ID NO: 19; a downstream sequence thereof is shown as SEQ ID NO: 22, which is obtained by adding AAAC to the 5' end of SEQ ID NO: 21, and the sgRNA sequence recognizes a 3' targeting site.

In one aspect, the disclosure relates to a construct including the sgRNA sequence as described herein.

The disclosure also relates to a cell comprising the construct as described herein.

In another aspect, the disclosure relates to a non-human mammalian cell, comprising the targeting vector as described herein, and one or more in vitro transcripts of the sgRNA construct.

In some embodiments, the cell includes Cas9 mRNA or an in vitro transcript thereof.

In some embodiments, the genes in the cell are heterozygous. In some embodiments, the genes in the cell are homozygous.

In some embodiments, the non-human mammalian cell is a mouse cell. In some embodiments, the cell is a fertilized egg cell. In some embodiments, the cell is a germ cell. In some embodiments, the cell is a blastocyst. In some embodiments, the cell is a lymphocyte (e.g., a B-cell or a T-cell).

In another aspect, the disclosure relates to methods for establishing a LAG-3 gene humanized animal model. The methods include the steps of:

(a) providing the cell, and preferably the cell is a fertilized egg cell;

(b) culturing the cell in a liquid culture medium;

(c) transplanting the cultured cell to the fallopian tube or uterus of the recipient female non-human mammal, allowing the cell to develop in the uterus of the female non-human mammal;

(d) identifying the germline transmission in the offspring genetically modified humanized non-human mammal of the pregnant female in step (c).

In some embodiments, the establishment of a humanized animal model of LAG-3 gene using a gene editing technique is based on CRISPR/Cas9.

In some embodiments, the non-human mammal is mouse. In some embodiments, the mouse is a C57BL/6 mouse. In some embodiments, the non-human mammal in step (c) is a female with false pregnancy.

The disclosure also relates to a method for establishing a genetically-modified non-human animal expressing two human or chimeric (e.g., humanized) genes. The method includes the steps of (a) using the method for establishing a LAG-3 gene humanized animal model to obtain a LAG-3 gene genetically modified humanized mouse;

(b) mating the LAG-3 gene genetically modified humanized mouse obtained in step (a) with another humanized mouse, and then screening to obtain a double humanized mouse model.

In some embodiments, in step (b), the LAG-3 gene genetically modified humanized mouse obtained in step (a) is mated with a PD-1 or CTLA-4 humanized mouse to obtain a LAG-3 and PD-1 double humanized mouse model or a LAG-3 and CTLA-4 double humanized mouse model.

The disclosure also relates to non-human mammal generated through the methods as described herein.

In some embodiments, the genome thereof contains human gene(s).

In some embodiments, the non-human mammal is a rodent. In some embodiments, the non-human mammal is a mouse.

In some embodiments, the non-human mammal expresses a protein encoded by a humanized LAG-3 gene.

The disclosure also relates to an offspring of the non-human mammal.

In another aspect, the disclosure relates to a tumor bearing non-human mammal model, characterized in that the non-human mammal model is obtained through the method as described herein.

In some embodiments, the non-human mammal is a rodent. In some embodiments, the non-human mammal is a mouse.

The disclosure also relates to a cell or cell line, or a primary cell culture thereof derived from the non-human mammal or an offspring thereof, or the tumor bearing non-human mammal.

The disclosure further relates to the tissue, organ or a culture thereof derived from the non-human mammal or an offspring thereof, or the tumor bearing non-human mammal.

In another aspect, the disclosure relates to a tumor tissue derived from the non-human mammal or an offspring thereof when it bears a tumor, or the tumor bearing non-human mammal.

In one aspect, the disclosure relates to a LAG-3 amino acid sequence of a humanized animal, wherein the amino acid sequence is selected from the group consisting of:

a) an amino acid sequence shown in SEQ ID NO: 31;

b) an amino acid sequence having a homology of at least 90% with the amino acid sequence shown in SEQ ID NO: 31;

c) an amino acid sequence encoded by a nucleic acid sequence, wherein the nucleic acid sequence is able to hybridize to a nucleotide sequence encoding the amino acid shown in SEQ ID NO: 31 under a low stringency condition;

d) an amino acid sequence having a homology of at least 90%, 91%, 92%, 93%, 94%, 95%, 96%, 97%, 98%, or at least 99% with the amino acid sequence shown in SEQ ID NO: 31;

e) an amino acid sequence that is different from the amino acid sequence shown in SEQ ID NO: 31 by no more than 10, 9, 8, 7, 6, 5, 4, 3, 2 or no more than 1 amino acid; or f) an amino acid sequence that comprises a substitution, a deletion and/or insertion of one or more amino acids to the amino acid sequence shown in SEQ ID NO: 31.

The disclosure also relates to a LAG-3 nucleotide sequence of a humanized animal, wherein the nucleotide sequence is selected from the group consisting of:

a) a nucleotide sequence that encodes the LAG-3 amino acid sequence of a humanized animal as described herein;

b) a nucleotide sequence that is set forth in SEQ ID NO: 30;

c) a nucleotide sequence having a coding DNA sequence (CDS) as shown in SEQ ID NO: 29;

d) a nucleotide sequence that is able to hybridize to the nucleotide sequence as shown in SEQ ID NO: 30 or SEQ ID NO: 29 under a low stringency condition;

e) a nucleotide sequence that has a homology of at least 90% with the nucleotide sequence as shown in SEQ ID NO: 29 or SEQ ID NO: 30;

f) a nucleotide sequence that encodes an amino acid sequence, wherein the amino acid sequence has a homology of at least 90% with the amino acid sequence shown in SEQ ID NO: 31;

g) a nucleotide sequence that encodes an amino acid sequence, wherein the amino acid sequence has a homology of at least 90%, 91%, 92%, 93%, 94%, 95%, 96%, 97%, 98%, or at least 99% with the amino acid sequence shown in SEQ ID NO: 31;

h) a nucleotide sequence that encodes an amino acid sequence, wherein the amino acid sequence is different from the amino acid sequence shown in SEQ ID NO: 31 by no more than 10, 9, 8, 7, 6, 5, 4, 3, 2 or no more than 1 amino acid; and/or i) a nucleotide sequence that encodes an amino acid sequence, wherein the amino acid sequence comprises a substitution, a deletion and/or insertion of 1, 2, 3, 4, 5, 6, 7, 8, 9, or more amino acids to the amino acid sequence shown in SEQ ID NO: 31.

j) and optimized SEQ ID NO: 30.

The disclosure further relates to a LAG-3 genomic DNA sequence of a humanized mouse, a DNA sequence obtained by a reverse transcription of the mRNA obtained by transcription thereof is consistent with or complementary to the DNA sequence; a construct expressing the amino acid sequence thereof; a cell comprising the construct thereof; a tissue comprising the cell thereof.

The disclosure further relates to the use of the non-human mammal or an offspring thereof, or the tumor bearing non-human mammal, the animal model generated through the method as described herein in the development of a product related to an immunization processes of human cells, the manufacture of a human antibody, or the model system for a research in pharmacology, immunology, microbiology and medicine.

The disclosure also relates to the use of the non-human mammal or an offspring thereof, or the tumor bearing non-human mammal, the animal model generated through the method as described herein in the production and utilization of an animal experimental disease model of an immunization processes involving human cells, the study on a pathogen, or the development of a new diagnostic strategy and/or a therapeutic strategy.

The disclosure further relates to the use of the non-human mammal or an offspring thereof, or the tumor bearing non-human mammal, the animal model generated through the methods as described herein, in the screening, verifying, evaluating or studying the LAG-3 gene function, human LAG-3 antibodies, the drugs or efficacies for human LAG-3 targeting sites, and the drugs for immune-related diseases and antitumor drugs.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 3A is a schematic diagram showing comparison of human and mouse LAG-3 genes.

FIG. 3B is a schematic diagram showing a humanized LAG-3 mouse gene map.

FIGS. 8A-8C), anti-human LAG-3 antibody (hLAG3 Alexa Fluor 647; FIGS. 8D-8F), or anti-human LAG-3 antibody (hLAG3 APC; FIGS. 8G-8I) and analyzed using flow cytometry. Compared to the control group (FIGS. 8A, 8D, 8G), cells expressing humanized LAG-3 protein can be detected in the spleens of humanized LAG-3 F1 heterozygous mouse; whereas in the spleens of C57BL/6 mice, no cell expressing humanized LAG-3 protein was detected.

FIGS. 9A-9C), anti-human LAG-3 antibody (hLAG3 APC; FIGS. 9D-9F), or anti-human LAG-3 antibody (hLAG3 Alexa Fluor 647; FIGS. 9G-9I), and analyzed using flow cytometry. Cells expressing humanized LAG-3 protein can be detected in the spleens of humanized LAG-3 F1 homozygotes (FIGS. 9F, 9I).

In FIGS. 13A, 13B, + is a known humanized LAG-3 homozygous mouse, − is wildtype control, WT is wildtype, "mut" indicates humanized LAG-3. In FIGS. 13C, 13D, −/− is a humanized PD-1 homozygous mouse, +/− is humanized PD-1 heterozygous mouse, WT is wildtype, "mut" indicates humanized PD-1. FIGS. 13A and 13B show that the mice numbered 3020 to 3023 were humanized LAG-3 homozygous mice. FIGS. 13C and 13D show that the mice numbered 3019 to 3027 were humanized PD-1 homozygous mice. FIGS. 13A-13D show that the four mice numbered 3020 to 3023 are double humanized mice that are homozygous for both humanized PD-1 and humanized LAG-3.

In FIGS. 16A and 16B, + is humanized CTLA-4 homozygous mouse, − is wildtype, WT is wildtype, "mut" indicates humanized CTLA-4. In FIGS. 16C and 16D, + is LAG-3 heterozygous mouse, − is wildtype, WT is wildtype, "mut" indicates humanized LAG-3. FIGS. 16A and 16B show that the mice numbered 1106 to 1117 were humanized CTLA-4 homozygous mice. FIGS. 16C and 16D show that the mice numbered 1106 to 1117 were humanized LAG-3 homozygous mice. FIGS. 16A-16D show that the twelve mice numbered 1106 to 1117 were double humanized mice that are homozygous for both humanized CTLA-4 and humanized LAG-3.

FIG. 21 shows the alignment between mouse LAG-3 amino acid sequence (NP 032505.1; SEQ ID NO: 25) and human LAG-3 amino acid sequence (NP_002277.4; SEQ ID NO: 27) by NCBI Basic Local Alignment Search Tool (BLAST).

SEQUENCE LISTING

Figures 1A, 1B:
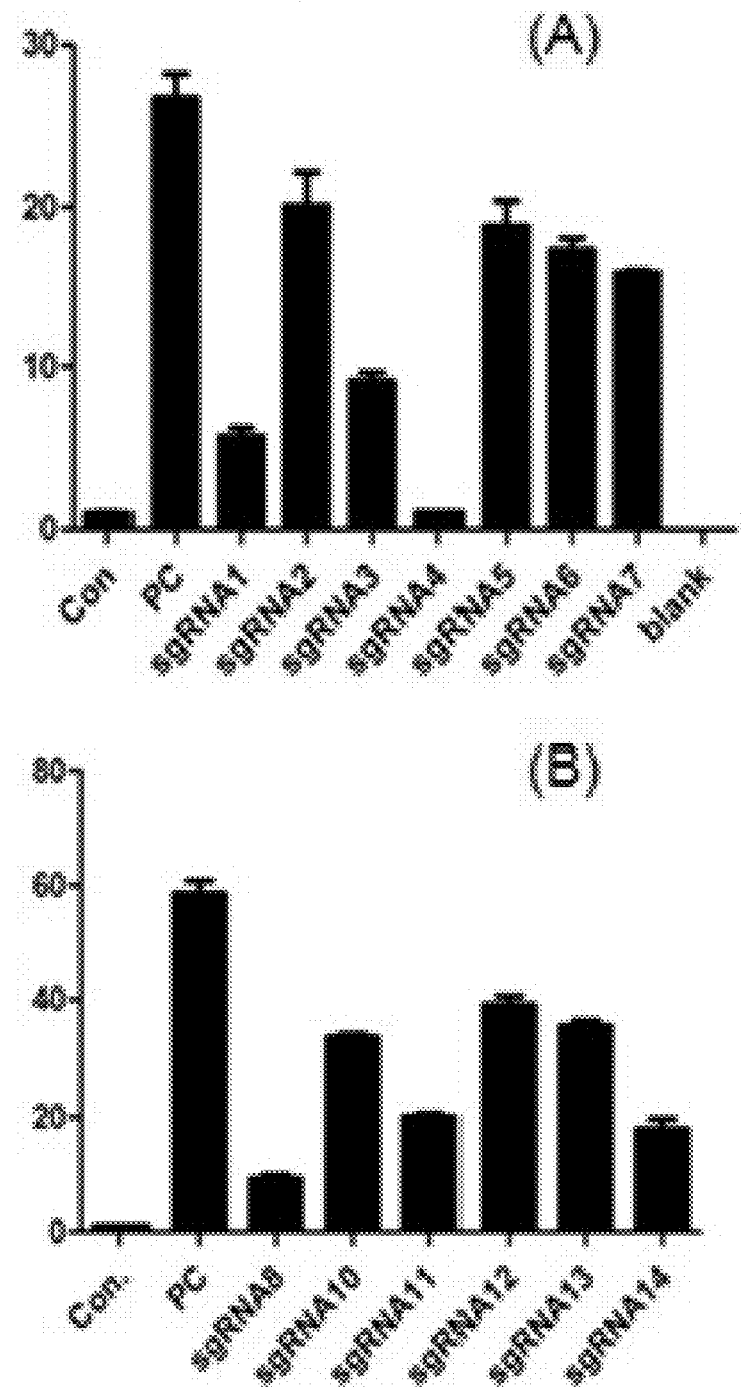
FIG. 1A is a graph showing activity testing results for sgRNA1-sgRNA7 (Con is a negative control; PC is a positive control; and blank is a blank control).
FIG. 1B is a graph showing activity testing results for sgRNA8-sgRNA14 (Con is a negative control; and PC is a positive control).

The instant application contains a Sequence Listing which has been submitted electronically in ASCII format and is hereby incorporated by reference in its entirety. Said ASCII copy, created on Aug. 19, 2019, is named Revised Sequence Listing.txt and is 38,985 bytes in size.

DETAILED DESCRIPTION

This disclosure relates to transgenic non-human animal with human or chimeric (e.g., humanized) Lymphocyte Activation Gene 3 (LAG-3), and methods of use thereof.

LAG-3 (CD223) is a co-inhibitory receptor of T cells. Expression of LAG-3 has been reported in activated CD4+ and CD8+ effector T cells, CD4+Foxp3+ Treg, Tr1 cells, B cells, plasmacytoid DCs, and NK cells. LAG-3 associates with CD3 in the TCR complex and crosslinking of LAG-3 together with CD3 negatively regulates signal transduction leading to reduced T cell proliferation and cytokine production. LAG-3 deficient OVA-specific CD4+ T cells show uncontrolled expansion upon immunization with their cognate antigen (Workman, Creg J., and Dario A A Vignali. "The CD4-related molecule, LAG-3 (CD223), regulates the expansion of activated T cells." European journal of immunology 33.4 (2003): 970-979). Similarly, increased proliferation of LAG-3 deficient donor T cells causes more severe acute GVHD. On CD8+ T cells, LAG-3 expression is induced by T cell activation and, like in CD4+ T cells, blockade of LAG-3 improves cytotoxic T cell (CTL) proliferation and effector function. In Tregs, loss of LAG-3 reduced the suppressive function of Tregs, while forced expression of LAG-3 conferred effector T cells with suppressive capacity. LAG-3 thus plays an important role in dampening immune responses by functionally contributing to immune suppression by regulatory T cells. (Nicole Joller and Vijay K. Kuchroo, "Tim-3, Lag-3, and TIGIT," Curr Top Microbiol Immunol. 2017 Sep. 13.)

As LAG-3 is involved in T cell inhibitory pathway, it thus can be expected that the LAG-3 antibody has great application values, e.g., as a tumor immunotherapy or a treatment for autoimmune disease (e.g., psoriasis and plaque psoriasis). In order to make the animal experiments more effective and more relevant, the present disclosure provides humanized LAG-3 genetically modified animal models and methods of establishing such animal models.

Experimental animal models are an indispensable research tool for studying the etiology, pathogenesis of the disease, as well as the development of prevention and control techniques and therapeutic drugs for the disease. Common experimental animals include mice, rats, guinea pigs, hamsters, rabbits, dogs, monkeys, pigs, fish and so on. However, there are many differences between human and animal genes and protein sequences, and many human proteins cannot bind to the animal's homologous proteins to produce biological activity, leading to that the results of many clinical trials do not match the results obtained from animal experiments. A large number of clinical studies are in urgent need of better animal models. With the continuous development and maturation of genetic engineering technologies, the use of human cells or genes to replace or substitute an animal's endogenous similar cells or genes to establish a biological system or disease model closer to human, and establish the humanized experimental animal models (humanized animal model) has provided an important tool for new clinical approaches or means. In this context, the genetically engineered animal model, that is, the use of genetic manipulation techniques, the use of human normal or mutant genes to replace animal homologous genes, can be used to establish the genetically modified animal models that are closer to human gene systems. The humanized animal models have various important applications. For example, due to the presence of human or humanized genes, the animals can express or express in part of the proteins with human functions, so as to greatly reduce the differences in clinical trials between humans and animals, and provide the possibility of drug screening at animal levels.

Unless otherwise specified, the practice of the methods described herein can take advantage of the techniques of cell biology, cell culture, molecular biology, transgenic biology, microbiology, recombinant DNA and immunology. These techniques are explained in detail in the following literature, for examples: Molecular Cloning A Laboratory Manual, 2nd Ed., ed. By Sambrook, Fritsch and Maniatis (Cold Spring Harbor Laboratory Press: 1989); DNA Cloning, Volumes I and II (D. N. Glovered., 1985); Oligonucleotide Synthesis (M. J. Gaited., 1984); Mullisetal U.S. Pat. No. 4,683,195; Nucleic Acid Hybridization (B. D. Hames & S. J. Higginseds. 1984); Transcription And Translation (B. D. Hames & S. J. Higginseds. 1984); Culture Of Animal Cell (R. I. Freshney, Alan R. Liss, Inc., 1987); Immobilized Cells And Enzymes (IRL Press, 1986); B. Perbal, A Practical Guide To Molecular Cloning (1984), the series, Methods In ENZYMOLOGY (J. Abelson and M. Simon, eds.-in-chief, Academic Press, Inc., New York), specifically, Vols. 154 and 155 (Wuetal. eds.) and Vol. 185, "Gene Expression Technology" (D. Goeddel, ed.); Gene Transfer Vectors For Mammalian Cells (J. H. Miller and M. P. Caloseds., 1987, Cold Spring Harbor Laboratory); Immunochemical Methods In Cell And Molecular Biology (Mayer and Walker, eds., Academic Press, London, 1987); Hand book Of Experimental Immunology, Volumes V (D. M. Weir and C. C. Blackwell, eds., 1986); and Manipulating the Mouse Embryo, (Cold Spring Harbor Laboratory Press, Cold Spring Harbor, N. Y., 1986), each of which is incorporated herein in its entirety by reference.

LAG-3 (Lymphocyte Activation Gene 3)

LAG-3 (also known as CD223) is an immunoglobulin superfamily member composed of four extracellular Ig-like domains and a type I transmembrane domain. Major histocompatibility complex class II (MHC-II) is a ligand for LAG-3; additional ligands including L-selectin and galectin-3 have also been identified. LAG-3+ tumor-infiltrating lymphocytes (TILs) have been reported in melanoma, colon, pancreatic, breast, lung, hematopoietic, and head and neck cancer patients, in association with aggressive clinical features. (Nicole Joller and Vijay K. Kuchroo, "Tim-3, Lag-3, and TIGIT," Curr Top Microbiol Immunol. 2017; Burugu, Samantha, Amanda R. Dancsok, and Torsten O. Nielsen. "Emerging targets in cancer immunotherapy." Seminars in Cancer Biology. Academic Press, 2017; Hemon, Patrice, et al. "MHC class II engagement by its ligand LAG-3 (CD223) contributes to melanoma resistance to apoptosis." The Journal of Immunology 186.9 (2011): 5173-5183).

In human genomes, LAG-3 gene locus has eight exons, exon 1, exon 2, exon 3, exon 4, exon 5, exon 6, exon 7, and exon 8 (FIG. 3A). The LAG-3 protein also has an extracellular region, a transmembrane region, and a cytoplasmic region, and the signal peptide is located at the extracellular region of LAG-3. The nucleotide sequence for human LAG-3 mRNA is NM_002286.5 (SEQ ID NO: 26), and the amino acid sequence for human LAG-3 is NP_002277.4 (SEQ ID NO: 27). The location for each exon and each region in human LAG-3 nucleotide sequence and amino acid sequence is listed below:

TABLE 1

| Human LAG-3 (approximate location) | NM_002286.5 1995 bp (SEQ ID NO: 26) | NP_002277.4 525 aa (SEQ ID NO: 27) |
|---|---|---|
| Exon 1 | 1-407 | 1-19 |
| Exon 2 | 408-555 | 20-69 |
| Exon 3 | 556-860 | 70-170 |
| Exon 4 | 861-1130 | 171-260 |
| Exon 5 | 1131-1406 | 261-352 |
| Exon 6 | 1407-1649 | 353-433 |
| Exon 7 | 1650-1780 | 434-477 |
| Exon 8 | 1781-1992 | 478-525 |
| Signal peptide | 350-415 | 1-22 |
| Extracellular region (excluding signal peptide region) | 416-1699 | 23-450 |
| Transmembrane region | 1700-1762 | 451-471 |
| Cytoplasmic region | 1763-1924 | 472-525 |
| Donor region in Example | 422-847 | 25-166 |

Similarly, in mice, LAG-3 gene locus has eight exons, exon 1, exon 2, exon 3, exon 4, exon 5, exon 6, exon 7, and exon 8 (FIG. 3A). The LAG-3 protein also has an extracellular region, a transmembrane region, and a cytoplasmic region, and the signal peptide is located at the extracellular region of LAG-3. The nucleotide sequence for mouse LAG-3 cDNA is NM_008479.2 (SEQ ID NO: 24), the amino acid sequence for mouse LAG-3 is NP_032505.1 (SEQ ID NO: 25). The location for each exon and each region in the mouse LAG-3 nucleotide sequence and amino acid sequence is listed below:

TABLE 2

| Mouse LAG-3 (approximate location) | NM_008479.2 2020 bp (SEQ ID NO: 24) | NP_032505.1 521 aa (SEQ ID NO: 25) |
|---|---|---|
| Exon 1 | 1-412 | 1-19 |
| Exon 2 | 413-560 | 20-69 |
| Exon 3 | 561-853 | 70-166 |
| Exon 4 | 854-1117 | 167-254 |
| Exon 5 | 1118-1393 | 255-346 |
| Exon 6 | 1394-1630 | 347-425 |
| Exon 7 | 1631-1761 | 426-469 |
| Exon 8 | 1762-2003 | 470-521 |
| Signal peptide | 355-420 | 1-22 |
| Extracellular region (excluding signal peptide region) | 421-1680 | 23-442 |
| Transmembrane region | 1681-1743 | 443-463 |
| Cytoplasmic region | 1744-1917 | 464-521 |
| Replaced region in Example | 427-840 | 25-162 |

The mouse LAG-3 gene (Gene ID: 16768) is located in Chromosome 11 of the mouse genome, which is located from 124904359-124912434 of NC_000072.6 (GRCm38.p4 (GCF 000001635.24)). The approximate locations of 5'-UTR, 3'-URT, exons and introns are listed below (LAG-3 has a reverse orientation on the chromosome). The 5'-UTR is from 124,911,705 to 124,911,352, exon 1 is from 124911351 to 124911294, the first intron is from 124,911, 293 to 124,910,912, exon 2 is from 124,910,911 to 124,910, 764, the second intron is from 124,910,763 to 124,910,397, exon 3 is from 124,910,396 to 124,910,104, the third intron is from 124,910,103 to 124,909,490, exon 4 is from 124, 909,489 to 124,909,226, the fourth intron is from 124,909, 225 to 124,908,653, exon 5 is from 24,908,652 to 124,908, 377, the fifth intron is from 124,908,376 to 124,905,493, exon 6 is from 124,905,492 to 124,905,256, the sixth intron is from 124,905,255 to 124,904,969, exon 7 is from 124,904,968 to 124,904,838, the seventh intron is from 124,904,837 to 124,904,601, exon 8 is from 124,904,600 to 124904442, the 3'-UTR is from 124904441 to 124,904,361 of NC_000072.6, based on transcript NM_008479.2. All relevant information for mouse LAG-3 locus can be found in the NCBI website with Gene ID: 16768, which is incorporated by reference herein in its entirety.

FIG. 22 shows the alignment between mouse LAG-3 amino acid sequence (NP_032505.1; SEQ ID NO: 25) and human LAG-3 amino acid sequence (NP_002277.4; SEQ ID NO: 27). Thus, the corresponding amino acid residue or region between human and mouse LAG-3 can also be found in FIG. 22.

LAG-3 genes, proteins, and locus of the other species are also known in the art. For example, the gene ID for LAG-3 in *Rattus norvegicus* is 297596, the gene ID for LAG-3 in *Macaca mulatta* (Rhesus monkey) is 713737, the gene ID for LAG-3 in *Sus scrofa* (pig) is 100125962. The relevant information for these genes (e.g., intron sequences, exon sequences, amino acid residues of these proteins) can be found, e.g., in NCBI database.

The present disclosure provides human or chimeric (e.g., humanized) LAG-3 nucleotide sequence and/or amino acid sequences. In some embodiments, the entire sequence of mouse exon 1, exon 2, exon 3, exon 4, exon 5, exon 6, exon 7, exon 8, signal peptide, extracellular region, transmembrane region, and/or cytoplasmic region are replaced by the corresponding human sequence. In some embodiments, a "region" or "portion" of mouse exon 1, exon 2, exon 3, exon 4, exon 5, exon 6, exon 7, exon 8, signal peptide, extracellular region, transmembrane region, and/or cytoplasmic region are replaced by the corresponding human sequence. The term "region" or "portion" can refer to at least 1, 2, 3, 4, 5, 6, 7, 8, 9, 10, 20, 30, 40, 50, 60, 70, 80, 90, 100, 110, 120, 130, 150, 200, 250, 300, 350, or 400 nucleotides, or at least 1, 2, 3, 4, 5, 6, 7, 8, 9, 10, 20, 30, 40, 50, 60, 70, 80, 90, 100, 110, 120, 130, or 150 amino acid residues. In some embodiments, the "region" or "portion" can be at least 50%, 55%, 60%, 65%, 70%, 75%, 80%, 85%, 90%, 95%, or 99% identical to exon 1, exon 2, exon 3, exon 4, exon 5, exon 6, exon 7, exon 8, signal peptide, extracellular region, transmembrane region, or cytoplasmic region. In some embodiments, a region, a portion, or the entire sequence of mouse exon 1, exon 2, exon 3, exon 4, exon 5, exon 6, exon 7, and/or exon 8 (e.g., exon 2 and exon 3) are replaced by the human exon 1, exon 2, exon 3, exon 4, exon 5, exon 6, exon 7, and/or exon 8 (e.g., exon 2 and exon 3) sequence.

In some embodiments, the present disclosure also provides a chimeric (e.g., humanized) LAG-3 nucleotide sequence and/or amino acid sequences, wherein in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from mouse LAG-3 mRNA sequence (e.g., SEQ ID NO: 24), or mouse LAG-3 amino acid sequence (e.g., SEQ ID NO: 25); and in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from human LAG-3 mRNA sequence (e.g., SEQ ID NO: 26), or human LAG-3 amino acid sequence (e.g., SEQ ID NO: 27).

In some embodiments, the sequence encoding amino acids 25-162 of mouse LAG-3 (SEQ ID NO: 25) is replaced. In some embodiments, the sequence is replaced by a sequence encoding a corresponding region of human LAG-3 (e.g., amino acids 25-166 of human LAG-3 (SEQ ID NO: 27).

In some embodiments, the nucleic acids as described herein are operably linked to a promotor or regulatory element, e.g., an endogenous mouse LAG-3 promotor, an inducible promoter, an enhancer, and/or mouse or human regulatory elements.

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that are different from a portion of or the entire mouse LAG-3 nucleotide sequence (e.g., exon 1, exon 2, exon 3, exon 4, exon 5, exon 6, exon 7, exon 8, or NM_008479.2 (SEQ ID NO: 24)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire mouse LAG-3 nucleotide sequence (e.g., exon 1, exon 2, exon 3, exon 4, exon 5, exon 6, exon 7, exon 8, or NM_008479.2 (SEQ ID NO: 24)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is different from a portion of or the entire human LAG-3 nucleotide sequence (e.g., exon 1, exon 2, exon 3, exon 4, exon 5, exon 6, exon 7, exon 8, or NM_002286.5 (SEQ ID NO: 26)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire human LAG-3 nucleotide sequence (e.g., exon 1, exon 2, exon 3, exon 4, exon 5, exon 6, exon 7, exon 8, or NM_002286.5 (SEQ ID NO: 26)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire mouse LAG-3 amino acid sequence (e.g., exon 1, exon 2, exon 3, exon 4, exon 5, exon 6, exon 7, exon 8 or NP_032505.1 (SEQ ID NO: 25)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire mouse LAG-3 amino acid sequence (e.g., exon 1, exon 2, exon 3, exon 4, exon 5, exon 6, exon 7, exon 8, or NP_032505.1 (SEQ ID NO: 25)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire human LAG-3 amino acid sequence (e.g., exon 1, exon 2, exon 3, exon 4, exon 5, exon 6, exon 7, exon 8, or NP_002277.4 (SEQ ID NO: 27)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire human LAG-3 amino acid sequence (e.g., exon 1, exon 2, exon 3, exon 4, exon 5, exon 6, exon 7, exon 8, or NP_002277.4 (SEQ ID NO: 27)).

The present disclosure also provides a humanized LAG-3 mouse amino acid sequence, wherein the amino acid sequence is selected from the group consisting of:

a) an amino acid sequence shown in SEQ ID NO: 31;

b) an amino acid sequence having a homology of at least 90% with or at least 90% identical to the amino acid sequence shown in SEQ ID NO: 31;

c) an amino acid sequence encoded by a nucleic acid sequence, wherein the nucleic acid sequence is able to hybridize to a nucleotide sequence encoding the amino acid shown in SEQ ID NO: 31 under a low stringency condition;

d) an amino acid sequence having a homology of at least 90%, 91%, 92%, 93%, 94%, 95%, 96%, 97%, 98%, or 99%, or at least 90%, 91%, 92%, 93%, 94%, 95%, 96%, 97%, 98%, or 99% identical to the amino acid sequence shown in SEQ ID NO: 31;

e) an amino acid sequence that is different from the amino acid sequence shown in SEQ ID NO: 31 by no more than 10, 9, 8, 7, 6, 5, 4, 3, 2 or no more than 1 amino acid; or f) an amino acid sequence that comprises a substitution, a deletion and/or insertion of one or more amino acids to the amino acid sequence shown in SEQ ID NO: 31.

The present disclosure also relates to a LAG-3 nucleotide (e.g., DNA or RNA) sequence, wherein the nucleotide sequence can be selected from the group consisting of:

a) a nucleotide sequence as shown in SEQ ID NO: 29, or a nucleotide sequence encoding a homologous LAG-3 amino acid sequence of a humanized mouse;

b) a nucleotide sequence that is shown in SEQ ID NO: 30;

c) a nucleotide sequence that is able to hybridize to the nucleotide sequence as shown in SEQ ID NO: 29 or SEQ ID NO: 30 under a low stringency condition;

d) a nucleotide sequence that has a homology of at least 90% or at least 90% identical to the nucleotide sequence as shown in SEQ ID NO: 29 or SEQ ID NO: 30;

e) a nucleotide sequence that encodes an amino acid sequence, wherein the amino acid sequence has a homology of at least 90% with or at least 90% identical to the amino acid sequence shown in SEQ ID NO: 31;

f) a nucleotide sequence that encodes an amino acid sequence, wherein the amino acid sequence has a homology of at least 90%, 91%, 92%, 93%, 94%, 95%, 96%, 97%, 98%, or 99% with, or at least 90%, 91%, 92%, 93%, 94%, 95%, 96%, 97%, 98%, or 99% identical to the amino acid sequence shown in SEQ ID NO: 31;

g) a nucleotide sequence that encodes an amino acid sequence, wherein the amino acid sequence is different from the amino acid sequence shown in SEQ ID NO: 31 by no more than 10, 9, 8, 7, 6, 5, 4, 3, 2 or no more than 1 amino acid; and/or h) a nucleotide sequence that encodes an amino acid sequence, wherein the amino acid sequence comprises a substitution, a deletion and/or insertion of one or more amino acids to the amino acid sequence shown in SEQ ID NO: 31.

The present disclosure further relates to a LAG-3 genomic DNA sequence of a humanized mouse. The DNA sequence is obtained by a reverse transcription of the mRNA obtained by transcription thereof is consistent with or complementary to the DNA sequence homologous to the sequence shown in SEQ ID NO: 29 or SEQ ID NO: 30.

The disclosure also provides an amino acid sequence that has a homology of at least 90% with, or at least 90% identical to the sequence shown in SEQ ID NO: 31, and has protein activity. In some embodiments, the homology with the sequence shown in SEQ ID NO: 31 is at least about 90%, 91%, 92%, 93%, 94%, 95%, 96%, 97%, 98%, or at least 99%. In some embodiments, the foregoing homology is at least about 50%, 51%, 52%, 53%, 54%, 55%, 56%, 57%, 58%, or at least about 59%.

In some embodiments, the percentage identity with the sequence shown in SEQ ID NO: 31 is at least about 90%, 91%, 92%, 93%, 94%, 95%, 96%, 97%, 98%, or at least 99%. In some embodiments, the foregoing percentage identity is at least about 50%, 51%, 52%, 53%, 54%, 55%, 56%, 57%, 58%, or at least about 59%.

The disclosure also provides a nucleotide sequence that has a homology of at least 90%, or at least 90% identical to the sequence shown in SEQ ID NO: 30, and encodes a polypeptide that has protein activity. In some embodiments, the homology with the sequence shown in SEQ ID NO: 30 is at least about 90%, 91%, 92%, 93%, 94%, 95%, 96%, 97%, 98%, or at least 99%. In some embodiments, the foregoing homology is at least about 50%, 51%, 52%, 53%, 54%, 55%, 56%, 57%, 58%, or at least about 59%.

In some embodiments, the percentage identity with the sequence shown in SEQ ID NO: 30 is at least about 90%, 91%, 92%, 93%, 94%, 95%, 96%, 97%, 98%, or at least 99%. In some embodiments, the foregoing percentage identity is at least about 50%, 51%, 52%, 53%, 54%, 55%, 56%, 57%, 58%, or at least about 59%.

The disclosure also provides a nucleic acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any nucleotide sequence as described herein, and an amino acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any amino acid sequence as described herein. In some embodiments, the disclosure relates to nucleotide sequences encoding any peptides that are described herein, or any amino acid sequences that are encoded by any nucleotide sequences as described herein. In some embodiments, the nucleic acid sequence is less than 10, 20, 30, 40, 50, 60, 70, 80, 90, 100, 110, 120, 130, 150, 200, 250, 300, 350, 400, or 500 nucleotides. In some embodiments, the amino acid sequence is less than 5, 6, 7, 8, 9, 10, 20, 30, 40, 50, 60, 70, 80, 90, 100, 110, 120, 130, or 150 amino acid residues.

In some embodiments, the amino acid sequence (i) comprises an amino acid sequence; or (ii) consists of an amino acid sequence, wherein the amino acid sequence is any one of the sequences as described herein.

In some embodiments, the nucleic acid sequence (i) comprises a nucleic acid sequence; or (ii) consists of a nucleic acid sequence, wherein the nucleic acid sequence is any one of the sequences as described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90%, 95%, or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blossum 62 scoring matrix with a gap penalty of 12, a gap extend penalty of 4, and a frameshift gap penalty of 5.

The term "percent homology" is often used to mean "sequence similarity." The percentage of identical residues (percent identity) and the percentage of residues conserved with similar physicochemical properties (percent similarity), e.g. leucine and isoleucine, are both used to "quantify the homology". Residues conserved with similar physicochemical properties are well known in the art. The percent homology, in many cases, is higher than the percent identity.

Cells, tissues, and animals (e.g., mouse) are also provided that comprise the nucleotide sequences as described herein, as well as cells, tissues, and animals (e.g., mouse) that express human or chimeric (e.g., humanized) LAG-3 from an endogenous non-human LAG-3 locus.

Genetically Modified Animals

As used herein, the term "genetically-modified non-human animal" refers to a non-human animal having exogenous DNA in at least one chromosome of the animal's genome. In some embodiments, at least one or more cells, e.g., at least 1%, 2%, 3%, 4%, 5%, 10%, 20%, 30%, 40%, 50% of cells of the genetically-modified non-human animal have the exogenous DNA in its genome. The cell having exogenous DNA can be various kinds of cells, e.g., an endogenous cell, a somatic cell, an immune cell, a T cell, a B cell, a germ cell, a blastocyst, or an endogenous tumor cell. In some embodiments, genetically-modified non-human animals are provided that comprise a modified endogenous LAG-3 locus that comprises an exogenous sequence (e.g., a human sequence), e.g., a replacement of one or more non-human sequences with one or more human sequences. The animals are generally able to pass the modification to progeny, i.e., through germline transmission.

As used herein, the term "chimeric gene" or "chimeric nucleic acid" refers to a gene or a nucleic acid, wherein two or more portions of the gene or the nucleic acid are from different species, or at least one of the sequences of the gene or the nucleic acid does not correspond to the wildtype nucleic acid in the animal. In some embodiments, the chimeric gene or chimeric nucleic acid has at least one portion of the sequence that is derived from two or more different sources, e.g., sequences encoding different proteins or sequences encoding the same (or homologous) protein of two or more different species. In some embodiments, the chimeric gene or the chimeric nucleic acid is a humanized gene or humanized nucleic acid.

As used herein, the term "chimeric protein" or "chimeric polypeptide" refers to a protein or a polypeptide, wherein two or more portions of the protein or the polypeptide are from different species, or at least one of the sequences of the protein or the polypeptide does not correspond to wildtype amino acid sequence in the animal. In some embodiments, the chimeric protein or the chimeric polypeptide has at least one portion of the sequence that is derived from two or more different sources, e.g., same (or homologous) proteins of different species. In some embodiments, the chimeric protein or the chimeric polypeptide is a humanized protein or a humanized polypeptide.

In some embodiments, the chimeric gene or the chimeric nucleic acid is a humanized LAG-3 gene or a humanized LAG-3 nucleic acid. In some embodiments, at least one or more portions of the gene or the nucleic acid is from the human LAG-3 gene, at least one or more portions of the gene or the nucleic acid is from a non-human LAG-3 gene. In some embodiments, the gene or the nucleic acid comprises a sequence that encodes a LAG-3 protein. The encoded LAG-3 protein is functional or has at least one activity of the human LAG-3 protein or the non-human LAG-3 protein, e.g., binding to human or non-human MHC II, CD3, L-selectin or galectin-3, and/or inhibiting immune responses.

In some embodiments, the chimeric protein or the chimeric polypeptide is a humanized LAG-3 protein or a humanized LAG-3 polypeptide. In some embodiments, at least one or more portions of the amino acid sequence of the protein or the polypeptide is from a human LAG-3 protein, and at least one or more portions of the amino acid sequence of the protein or the polypeptide is from a non-human LAG-3 protein. The humanized LAG-3 protein or the humanized LAG-3 polypeptide is functional or has at least one activity of the human LAG-3 protein or the non-human LAG-3 protein The genetically modified non-human animal can be various animals, e.g., a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo. These methods are known in the art, and are described, e.g., in A. Nagy, et al., "Manipulating the Mouse Embryo: A Laboratory Manual (Third Edition)," Cold Spring Harbor Laboratory Press, 2003, which is incorporated by reference herein in its entirety.

In one aspect, the animal is a mammal, e.g., of the superfamily Dipodoidea or Muroidea. In some embodiments, the genetically modified animal is a rodent. The rodent can be selected from a mouse, a rat, and a hamster. In some embodiment, the rodent is selected from the superfamily Muroidea. In some embodiments, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rates, bamboo rats, and zokors). In some embodiments, the genetically modified rodent is selected from a true mouse or rat (family Muridae), a gerbil, a spiny mouse, and a crested rat. In one embodiment, the non-human animal is a mouse.

In some embodiments, the animal is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/01a. In some embodiments, the mouse is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2. These mice are described, e.g., in Festing et al., Revised nomenclature for strain 129 mice, Mammalian Genome 10:836 (1999); Auerbach et al., Establishment and Chimera Analysis of 129/SvEv- and C57BL/6-Derived Mouse Embryonic Stem Cell Lines (2000), both of which are incorporated herein by reference in the entirety. In some embodiments, the genetically modified mouse is a mix of the 129 strain and the C57BL/6 strain. In some embodiments, the mouse is a mix of the 129 strains, or a mix of the BL/6 strains. In some embodiment, the mouse is a BALB strain, e.g., BALB/c strain. In some embodiments, the mouse is a mix of a BALB strain and another strain. In some embodiments, the mouse is from a hybrid line (e.g., 50% BALB/c-50% 129S4/Sv; or 50% C57BL/6-50% 129).

In some embodiments, the animal is a rat. The rat can be selected from a Wistar rat, an LEA strain, a Sprague Dawley strain, a Fischer strain, F344, F6, and Dark Agouti. In some embodiments, the rat strain is a mix of two or more strains selected from the group consisting of Wistar, LEA, Sprague Dawley, Fischer, F344, F6, and Dark Agouti.

The animal can have one or more other genetic modifications, and/or other modifications, that are suitable for the particular purpose for which the humanized LAG-3 animal is made. For example, suitable mice for maintaining a xenograft (e.g., a human cancer or tumor), can have one or more modifications that compromise, inactivate, or destroy the immune system of the non-human animal in whole or in part. Compromise, inactivation, or destruction of the immune system of the non-human animal can include, for example, destruction of hematopoietic cells and/or immune cells by chemical means (e.g., administering a toxin), physical means (e.g., irradiating the animal), and/or genetic modification (e.g., knocking out one or more genes). Non-limiting examples of such mice include, e.g., NOD mice, SCID mice, NOD/SCID mice, IL2Rγ knockout mice, NOD/SCID/γcnull mice (Ito, M. et al., NOD/SCID/γcnull mouse: an excellent recipient mouse model for engraftment of human cells, Blood 100(9):3175-3182, 2002), nude mice, and Rag1 and/or Rag2 knockout mice. These mice can optionally be irradiated, or otherwise treated to destroy one or more immune cell type. Thus, in various embodiments, a genetically modified mouse is provided that can include a humanization of at least a portion of an endogenous non-human LAG-3 locus, and further comprises a modification that compromises, inactivates, or destroys the immune system (or one or more cell types of the immune system) of the non-human animal in whole or in part. In some embodiments, modification is, e.g., selected from the group consisting of a modification that results in NOD mice, SCID mice, NOD/SCID mice, IL-2Rγ knockout mice, NOD/SCID/γc null mice, nude mice, Rag1 and/or Rag2 knockout mice, and a combination thereof. These genetically modified animals are described, e.g., in US20150106961, which is incorporated herein by reference in its entirety. In some embodiments, the mouse can include a replacement of all or part of mature LAG-3 coding sequence with human mature LAG-3 coding sequence.

Genetically modified non-human animals that comprise a modification of an endogenous non-human LAG-3 locus. In some embodiments, the modification can comprise a human nucleic acid sequence encoding at least a portion of a mature LAG-3 protein (e.g., at least 10%, 20%, 30%, 40%, 50%, 60%, 70%, 80%, 90%, 95%, 96%, 97%, 98%, or 99% identical to the mature LAG-3 protein sequence). Although genetically modified cells are also provided that can comprise the modifications described herein (e.g., ES cells, somatic cells), in many embodiments, the genetically modified non-human animals comprise the modification of the endogenous LAG-3 locus in the germline of the animal.

Genetically modified animals can express a human LAG-3 and/or a chimeric (e.g., humanized) LAG-3 from endogenous mouse loci, wherein the endogenous mouse LAG-3 gene has been replaced with a human LAG-3 gene and/or a nucleotide sequence that encodes a region of human LAG-3 sequence or an amino acid sequence that is at least 10%, 20%, 30%, 40%, 50%, 60%, 70&, 80%, 90%, 95%, 96%, 97%, 98%, or 99% identical to the human LAG-3 sequence. In various embodiments, an endogenous non-human LAG-3 locus is modified in whole or in part to comprise human nucleic acid sequence encoding at least one protein-coding sequence of a mature LAG-3 protein.

In some embodiments, the genetically modified mice express the human LAG-3 and/or chimeric LAG-3 (e.g., humanized LAG-3) from endogenous loci that are under control of mouse promoters and/or mouse regulatory elements. The replacement(s) at the endogenous mouse loci provide non-human animals that express human LAG-3 or chimeric LAG-3 (e.g., humanized LAG-3) in appropriate cell types and in a manner that does not result in the potential pathologies observed in some other transgenic mice known in the art. The human LAG-3 or the chimeric LAG-3 (e.g., humanized LAG-3) expressed in animal can maintain one or more functions of the wildtype mouse or human LAG-3 in the animal. For example, human or non-human MHC II can bind to the expressed LAG-3 and downregulate immune response, e.g., downregulate immune response by at least 10%, 20%, 30%, 40%, or 50%. Furthermore, in some embodiments, the animal does not express endogenous LAG-3. As used herein, the term "endogenous LAG-3" refers to LAG-3 protein that is expressed from an endogenous LAG-3 nucleotide sequence of the genetically modified non-human animal (e.g., mouse) before the genetic modification.

The genome of the animal can comprise a sequence encoding an amino acid sequence that is at least 70%, 75%, 80%, 85%, 90%, 95%, 99%, or 100% identical to human LAG-3 (NP_002277.4) (SEQ ID NO: 27). In some embodiments, the genome comprises a sequence encoding an amino acid sequence that is at least 70%, 75%, 80%, 85%, 90%, 95%, 99%, or 100% identical to SEQ ID NO: 31.

The genome of the genetically modified animal can comprise a replacement at an endogenous LAG-3 gene locus of a sequence encoding a region of endogenous LAG-3 with a sequence encoding a corresponding region of human LAG-3. In some embodiments, the sequence that is replaced is any sequence within the endogenous LAG-3 gene locus, e.g., exon 1, exon 2, exon 3, exon 4, exon 5, exon 6, exon 7, exon 8, 5'-UTR, 3'UTR, the first intron, the second intron, and the third intron, the fourth intron, the fifth intron, the sixth intron, the seventh intron etc. In some embodiments, the sequence that is replaced is within the regulatory region of the endogenous LAG-3 gene. In some embodiments, the sequence that is replaced is exon 2 and exon 3, or part thereof of an endogenous mouse LAG-3 gene locus.

The genetically modified animal can have one or more cells expressing a human or chimeric LAG-3 (e.g., humanized LAG-3) having an extracellular region and a cytoplasmic region, wherein the extracellular region comprises a sequence that is at least 50%, 60%, 70%, 80%, 90%, 95%, 99% identical to the extracellular region of human LAG-3. In some embodiments, the extracellular region of the humanized LAG-3 has a sequence that has at least 10, 20, 30, 40, 50, 60, 70, 80, 90, or 100 amino acids (e.g., contiguously or non-contiguously) that are identical to human LAG-3. Because human LAG-3 and non-human LAG-3 (e.g., mouse LAG-3) sequences, in many cases, are different, antibodies that bind to human LAG-3 will not necessarily have the same binding affinity with mouse LAG-3 or have the same effects to mouse LAG-3. Therefore, the genetically modified animal having a human or a humanized extracellular region can be used to better evaluate the effects of anti-human LAG-3 antibodies in an animal model. In some embodiments, the genome of the genetically modified animal comprises a sequence encoding an amino acid sequence that corresponds to part or the entire sequence of exon 1, exon 2, exon 3, exon 4, exon 5, exon 6, exon 7, and/or exon 8 of human LAG-3, part or the entire sequence of extracellular region of human LAG-3 (with or without signal peptide), or part or the entire sequence of amino acids 25-166 of SEQ ID NO: 27.

In some embodiments, the non-human animal can have, at an endogenous LAG-3 gene locus, a nucleotide sequence encoding a chimeric human/non-human LAG-3 polypeptide, wherein a human portion of the chimeric human/non-human LAG-3 polypeptide comprises a portion of human LAG-3 extracellular domain, and wherein the animal expresses a functional LAG-3 on a surface of a cell of the animal. The human portion of the chimeric human/non-human LAG-3 polypeptide can comprise a portion of exon 1, exon 2, exon 3, exon 4, exon 5, exon 6, exon 7, and/or exon 8 of human LAG-3. In some embodiments, the human portion of the chimeric human/non-human LAG-3 polypeptide can comprise a sequence that is at least 80%, 85%, 90%, 95%, or 99% identical to amino acids 25-166 of SEQ ID NO: 27.

In some embodiments, the non-human portion of the chimeric human/non-human LAG-3 polypeptide comprises transmembrane and/or cytoplasmic regions of an endogenous non-human LAG-3 polypeptide. There may be several advantages that are associated with the transmembrane and/or cytoplasmic regions of an endogenous non-human LAG-3 polypeptide. For example, once a LAG-3 ligand (e.g., MHC II) binds to LAG-3, they can properly transmit extracellular signals into the cells and regulate the downstream pathway. A human or humanized transmembrane and/or cytoplasmic regions may not function properly in non-human animal cells. In some embodiments, a few extracellular amino acids that are close to the transmembrane region of LAG-3 are also derived from endogenous sequence.

Furthermore, the genetically modified animal can be heterozygous with respect to the replacement at the endogenous LAG-3 locus, or homozygous with respect to the replacement at the endogenous LAG-3 locus.

In some embodiments, the humanized LAG-3 locus lacks a human LAG-3 5'-UTR. In some embodiment, the humanized LAG-3 locus comprises a rodent (e.g., mouse) 5'-UTR. In some embodiments, the humanization comprises a human 3'-UTR. In appropriate cases, it may be reasonable to presume that the mouse and human LAG-3 genes appear to be similarly regulated based on the similarity of their 5'-flanking sequence. As shown in the present disclosure, humanized LAG-3 mice that comprise a replacement at an endogenous mouse LAG-3 locus, which retain mouse regulatory elements but comprise a humanization of LAG-3 encoding sequence, do not exhibit pathologies. Both genetically modified mice that are heterozygous or homozygous for human LAG-3 are grossly normal.

The present disclosure further relates to a non-human mammal generated through the methods as described herein. In some embodiments, the genome thereof contains human gene(s).

In some embodiments, the non-human mammal is a rodent, and preferably, the non-human mammal is a mouse.

In some embodiments, the non-human mammal expresses a protein encoded by a humanized LAG-3 gene.

In addition, the present disclosure also relates to a tumor bearing non-human mammal model, characterized in that the non-human mammal model is obtained through the methods as described herein. In some embodiments, the non-human mammal is a rodent (e.g., a mouse).

The present disclosure further relates to a cell or cell line, or a primary cell culture thereof derived from the non-human mammal or an offspring thereof, or the tumor bearing non-human mammal; the tissue, organ or a culture thereof derived from the non-human mammal or an offspring thereof, or the tumor bearing non-human mammal; and the tumor tissue derived from the non-human mammal or an offspring thereof when it bears a tumor, or the tumor bearing non-human mammal.

The present disclosure also provides non-human mammals produced by any of the methods described herein. In some embodiments, a non-human mammal is provided; and the genetically modified animal contains the DNA encoding human or humanized LAG-3 in the genome of the animal.

In some embodiments, the non-human mammal comprises the genetic construct as described herein (e.g., gene construct as shown in FIG. 3). In some embodiments, a non-human mammal expressing human or humanized LAG-3 is provided. In some embodiments, the tissue-specific expression of human or humanized LAG-3 protein is provided.

In some embodiments, the expression of human or humanized LAG-3 in a genetically modified animal is controllable, as by the addition of a specific inducer or repressor substance.

Non-human mammals can be any non-human animal known in the art and which can be used in the methods as described herein. Preferred non-human mammals are mammals, (e.g., rodents). In some embodiments, the non-human mammal is a mouse.

Genetic, molecular and behavioral analyses for the non-human mammals described above can performed. The present disclosure also relates to the progeny produced by the non-human mammal provided by the present disclosure mated with the same or other genotypes.

The present disclosure also provides a cell line or primary cell culture derived from the non-human mammal or a progeny thereof. A model based on cell culture can be prepared, for example, by the following methods. Cell cultures can be obtained by way of isolation from a non-human mammal, alternatively cell can be obtained from the cell culture established using the same constructs and the standard cell transfection techniques. The integration of genetic constructs containing DNA sequences encoding human LAG-3 protein can be detected by a variety of methods.

There are many analytical methods that can be used to detect exogenous DNA expression, including methods at the level of RNA (including the mRNA quantification approaches using reverse transcriptase polymerase chain reaction (RT-PCR) or Southern blotting, and in situ hybridization) and methods at the protein level (including histochemistry, immunoblot analysis and in vitro binding studies). In addition, the expression level of the gene of interest can be quantified by ELISA techniques well known to those skilled in the art. Many standard analysis methods can be used to complete quantitative measurements. For example, transcription levels can be measured using RT-PCR and hybridization methods including RNase protection, Southern blot analysis, RNA dot analysis (RNAdot) analysis. Immunohistochemical staining, flow cytometry, Western blot analysis can also be used to assess the presence of human LAG-3 protein.

Vectors

The present disclosure relates to a targeting vector, comprising: a) a DNA fragment homologous to the 5' end of a region to be altered (5' arm), which is selected from the LAG-3 gene genomic DNAs in the length of 100 to 10,000 nucleotides; b) a desired/donor DNA sequence encoding a donor region; and c) a second DNA fragment homologous to the 3' end of the region to be altered (3' arm), which is selected from the LAG-3 gene genomic DNAs in the length of 100 to 10,000 nucleotides.

In some embodiments, a) the DNA fragment homologous to the 5' end of a conversion region to be altered (5' arm) is selected from the nucleotide sequences that have at least 90% homology to the NCBI accession number NC_000072.6; c) the DNA fragment homologous to the 3' end of the region to be altered (3' arm) is selected from the nucleotide sequences that have at least 90% homology to the NCBI accession number NC_000072.6.

In some embodiments, a) the DNA fragment homologous to the 5' end of a region to be altered (5' arm) is selected from the nucleotides from the position 124911766 to the position 124910898 of the NCBI accession number NC_000072.6; c) the DNA fragment homologous to the 3' end of the region to be altered (3' arm) is selected from the nucleotides from the position 124910116 to the position 124908702 of the NCBI accession number NC_000072.6.

In some embodiments, the length of the selected genomic nucleotide sequence in the targeting vector can be about 1.2 kb, about 1.5 kb, or about 1 kb. In some embodiments, the length is about 869 bp or about 1415 bp.

In some embodiments, the region to be altered is exon 1, exon 2, exon 3, exon 4, exon 5, exon 6, exon 7, and/or exon 8 of LAG-3 gene (e.g., exon 2 and/or exon 3 of LAG-3 gene).

The targeting vector can further include a selected gene marker.

In some embodiments, the sequence of the 5' arm is shown in SEQ ID NO: 32; and the sequence of the 3' arm is shown in SEQ ID NO: 38.

In some embodiments, the target region is derived from human (e.g., 6773206-6773988 of NC_000012.12). For example, the target region in the targeting vector is a part or entirety of the nucleotide sequence of a human LAG-3, preferably the nucleotide sequence is shown as a first exon, a second exon, a third exon, a fourth exon, a fifth exon, a sixth exon, a seventh exon and/or an eighth exon of the DNA sequence of the human LAG-3. In some embodiments, the nucleotide sequence of the humanized LAG-3 encodes the humanized LAG-3 protein with the NCBI accession number NP_002277.4 (SEQ ID NO: 27).

The disclosure also relates to a cell comprising the targeting vectors as described above.

Moreover, the disclosure also relates to an sgRNA sequence for constructing a humanized animal model, wherein the sgRNA sequence targets the LAG-3 gene, the sgRNA is unique on the target sequence of the LAG-3 gene to be altered, and meets the sequence arrangement rule of 5'-NNN (20)-NGG3' or 5'-CCN-N (20)-3'; and in some embodiments, the targeting site of the sgRNA in the mouse LAG-3 gene is located on the exon 1, exon 2, exon 3, exon 4, exon 5, exon 6, exon 7, or exon 8 of the mouse LAG-3 gene (e.g., exon 2 and/or exon 3 of the mouse LAG-3 gene).

In some embodiments, an upstream sequence thereof is shown as SEQ ID NO: 15, and a downstream sequence thereof is shown as SEQ ID NO: 17, and the sgRNA sequence recognizes a 5' targeting site. In some embodiments, the forward oligonucleotide sequence is obtained by adding TAGG to the 5' end of SEQ ID NO: 15; and the reverse oligonucleotide sequence is obtained by adding AAAC to the 5' end of SEQ ID NO: 17.

In some embodiments, the disclosure provides an sgRNA sequence for constructing a humanized animal model, wherein an upstream sequence thereof is shown as SEQ ID NO: 19, and a downstream sequence thereof is shown as SEQ ID NO: 21, and the sgRNA sequence recognizes a 3' targeting site. In some embodiments, the forward oligonucleotide sequence is obtained by adding TAGG to the 5' end of SEQ ID NO: 19; and the reverse oligonucleotide sequence is obtained by adding AAAC to the 5' end of SEQ ID NO: 21.

In some embodiments, the disclosure relates to a construct including the sgRNA sequence, and/or a cell including the construct.

In addition, the present disclosure further relates to a non-human mammalian cell, having any one of the foregoing targeting vectors, and one or more in vitro transcripts of the sgRNA construct as described herein. In some embodiments, the cell includes Cas9 mRNA or an in vitro transcript thereof.

In some embodiments, the genes in the cell are heterozygous. In some embodiments, the genes in the cell are homozygous.

In some embodiments, the non-human mammalian cell is a mouse cell. In some embodiments, the cell is a fertilized egg cell.

Methods of Making Genetically Modified Animals

Genetically modified animals can be made by several techniques that are known in the art, including, e.g., non-homologous end-joining (NHEJ), homologous recombination (HR), zinc finger nucleases (ZFNs), transcription activator-like effector-based nucleases (TALEN), and the clustered regularly interspaced short palindromic repeats (CRISPR)-Cas system. In some embodiments, homologous recombination is used. In some embodiments, CRISPR-Cas9 genome editing is used to generate genetically modified animals. Many of these genome editing techniques are known in the art, and is described, e.g., in Yin et al., "Delivery technologies for genome editing," Nature Reviews Drug Discovery 16.6 (2017): 387-399, which is incorporated by reference in its entirety. Many other methods are also provided and can be used in genome editing, e.g., micro-injecting a genetically modified nucleus into an enucleated oocyte, and fusing an enucleated oocyte with another genetically modified cell.

Thus, in some embodiments, the disclosure provides replacing in at least one cell of the animal, at an endogenous LAG-3 gene locus, a sequence encoding a region of an endogenous LAG-3 with a sequence encoding a corresponding region of human or chimeric LAG-3. In some embodiments, the replacement occurs in a germ cell, a somatic cell, a blastocyst, or a fibroblast, etc. The nucleus of a somatic cell or the fibroblast can be inserted into an enucleated oocyte.

Figure 3C:
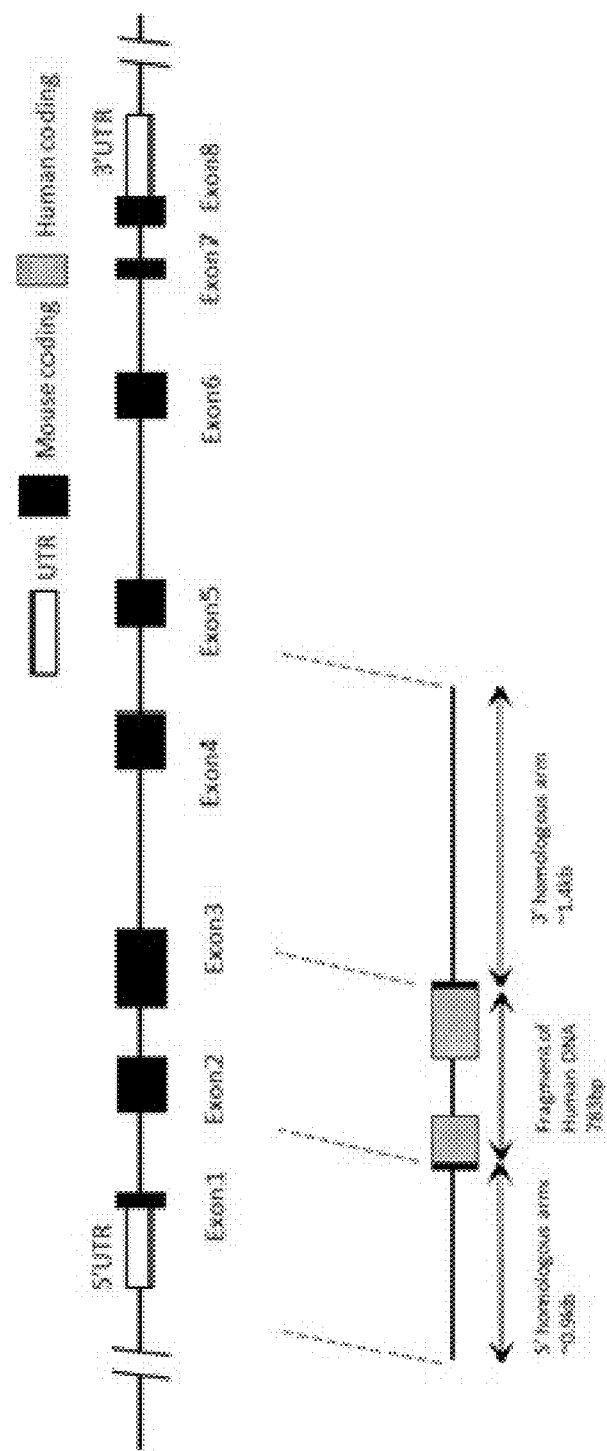
FIG. 3C is a schematic diagram showing a mouse LAG-3 gene targeting strategy.

FIG. 3C shows a humanization strategy for a mouse LAG-3 locus. In FIG. 3C, the targeting strategy involves a vector comprising the 5' end homologous arm, human LAG-3 gene fragment, 3' homologous arm. The process can involve replacing endogenous LAG-3 sequence with human sequence by homologous recombination. In some embodiments, the cleavage at the upstream and the downstream of the target site (e.g., by zinc finger nucleases, TALEN or CRISPR) can result in DNA double strands break, and the homologous recombination is used to replace endogenous LAG-3 sequence with human LAG-3 sequence.

Thus, in some embodiments, the methods for making a genetically modified, humanized animal, can include the step of replacing at an endogenous LAG-3 locus (or site), a nucleic acid encoding a sequence encoding a region of endogenous LAG-3 with a sequence encoding a corresponding region of human LAG-3. The sequence can include a region (e.g., a part or the entire region) of exon 1, exon 2, exon 3, exon 4, exon 5, exon 6, exon 7, and/or exon 8, of a human LAG-3 gene. In some embodiments, the sequence includes a region of exon 2 and exon 3 of a human LAG-3 gene (e.g., amino acids 25-166 of SEQ ID NO: 27). In some embodiments, the region is located within the extracellular region of LAG-3. In some embodiments, the endogenous LAG-3 locus is exon 2 and exon 3 of mouse LAG-3.

In some embodiments, the methods of modifying a LAG-3 locus of a mouse to express a chimeric human/mouse LAG-3 peptide can include the steps of replacing at the endogenous mouse LAG-3 locus a nucleotide sequence encoding a mouse LAG-3 with a nucleotide sequence encoding a human LAG-3, thereby generating a sequence encoding a chimeric human/mouse LAG-3.

In some embodiments, the nucleotide sequence encoding the chimeric human/mouse LAG-3 can include a first nucleotide sequence encoding an extracellular region of mouse LAG-3 (with or without the mouse signal peptide sequence); a second nucleotide sequence encoding an extracellular region of human LAG-3; a third nucleotide sequence encoding a transmembrane and a cytoplasmic region of a mouse LAG-3.

In some embodiments, the nucleotide sequences as described herein do not overlap with each other (e.g., the first nucleotide sequence, the second nucleotide sequence, and/or the third nucleotide sequence do not overlap). In some embodiments, the amino acid sequences as described herein do not overlap with each other.

The present disclosure further provides a method for establishing a LAG-3 gene humanized animal model, involving the following steps:

(a) providing the cell (e.g. a fertilized egg cell) based on the methods described herein;

(b) culturing the cell in a liquid culture medium;

(c) transplanting the cultured cell to the fallopian tube or uterus of the recipient female non-human mammal, allowing the cell to develop in the uterus of the female non-human mammal;

(d) identifying the germline transmission in the offspring genetically modified humanized non-human mammal of the pregnant female in step (c).

In some embodiments, the non-human mammal in the foregoing method is a mouse (e.g., a C57BL/6 mouse).

In some embodiments, the non-human mammal in step (c) is a female with pseudopregnancy (or false pregnancy).

In some embodiments, the fertilized eggs for the methods described above are C57BL/6 fertilized eggs. Other fertilized eggs that can also be used in the methods as described herein include, but are not limited to, FVB/N fertilized eggs, BALB/c fertilized eggs, DBA/1 fertilized eggs and DBA/2 fertilized eggs.

Fertilized eggs can come from any non-human animal, e.g., any non-human animal as described herein. In some embodiments, the fertilized egg cells are derived from rodents. The genetic construct can be introduced into a fertilized egg by microinjection of DNA. For example, by way of culturing a fertilized egg after microinjection, a cultured fertilized egg can be transferred to a false pregnant non-human animal, which then gives birth of a non-human mammal, so as to generate the non-human mammal mentioned in the method described above.

Methods of Using Genetically Modified Animals

Replacement of non-human genes in a non-human animal with homologous or orthologous human genes or human sequences, at the endogenous non-human locus and under control of endogenous promoters and/or regulatory elements, can result in a non-human animal with qualities and characteristics that may be substantially different from a typical knockout-plus-transgene animal. In the typical knockout-plus-transgene animal, an endogenous locus is removed or damaged and a fully human transgene is inserted into the animal's genome and presumably integrates at random into the genome. Typically, the location of the integrated transgene is unknown; expression of the human protein is measured by transcription of the human gene and/or protein assay and/or functional assay. Inclusion in the human transgene of upstream and/or downstream human sequences are apparently presumed to be sufficient to provide suitable support for expression and/or regulation of the transgene.

In some cases, the transgene with human regulatory elements expresses in a manner that is unphysiological or otherwise unsatisfactory, and can be actually detrimental to the animal. The disclosure demonstrates that a replacement with human sequence at an endogenous locus under control of endogenous regulatory elements provides a physiologically appropriate expression pattern and level that results in a useful humanized animal whose physiology with respect to the replaced gene are meaningful and appropriate in the context of the humanized animal's physiology.

Genetically modified animals that express human or humanized LAG-3 protein, e.g., in a physiologically appropriate manner, provide a variety of uses that include, but are not limited to, developing therapeutics for human diseases and disorders, and assessing the efficacy of these human therapeutics in the animal models.

In various aspects, genetically modified animals are provided that express human or humanized LAG-3, which are useful for testing agents that can decrease or block the interaction between LAG-3 and MHC II or the interaction between LAG-3 and other ligands (e.g., L-selectin, galectin-3), testing whether an agent can increase or decrease the immune response, and/or determining whether an agent is an LAG-3 agonist or antagonist. The genetically modified animals can be, e.g., an animal model of a human disease, e.g., the disease is induced genetically (a knock-in or knockout). In various embodiments, the genetically modified non-human animals further comprise an impaired immune system, e.g., a non-human animal genetically modified to sustain or maintain a human xenograft, e.g., a human solid tumor or a blood cell tumor (e.g., a lymphocyte tumor, e.g., a B or T cell tumor).

In some embodiments, the genetically modified animals can be used for determining effectiveness of an anti-LAG-3 antibody for the treatment of cancer. The methods involving administering the anti-LAG-3 antibody to the animal as described herein, wherein the animal has a tumor; and determining the inhibitory effects of the anti-LAG-3 antibody to the tumor. The inhibitor effects that can be determined include, e.g., a decrease of tumor size or tumor volume, a decrease of tumor growth, a reduction of the increase rate of tumor volume in a subject (e.g., as compared to the rate of increase in tumor volume in the same subject prior to treatment or in another subject without such treatment), a decrease in the risk of developing a metastasis or the risk of developing one or more additional metastasis, an increase of survival rate, and an increase of life expectancy, etc. The tumor volume in a subject can be determined by various methods, e.g., as determined by direct measurement, MRI or CT.

In some embodiments, the tumor comprises one or more tumor cells that express MHC II (Hemon, Patrice, et al. "MHC class II engagement by its ligand LAG-3 (CD223) contributes to melanoma resistance to apoptosis." The Journal of Immunology 186.9 (2011): 5173-5183). In some embodiments, the tumor comprises one or more cancer cells (e.g., human or mouse cancer cells) that are injected into the animal. In some embodiments, the anti-LAG-3 antibody or anti-MHC II antibody prevents MHC II from binding to LAG-3. In some embodiments, the anti-LAG-3 antibody or anti-MHC II antibody does not prevent MHC II from binding to LAG-3.

In some embodiments, the genetically modified animals can be used for determining whether an anti-LAG-3 antibody is an LAG-3 agonist or antagonist. In some embodiments, the methods as described herein are also designed to determine the effects of the agent (e.g., anti-LAG-3 antibodies) on LAG-3, e.g., whether the agent can stimulate T cells or inhibit T cells, whether the agent can upregulate the immune response or downregulate immune response. In some embodiments, the genetically modified animals can be used for determining the effective dosage of a therapeutic agent for treating a disease in the subject, e.g., cancer, or autoimmune diseases.

The inhibitory effects on tumors can also be determined by methods known in the art, e.g., measuring the tumor volume in the animal, and/or determining tumor (volume) inhibition rate ($TGI_{TV}$). The tumor growth inhibition rate can be calculated using the formula $TGI_{TV}$ (%)=(1−TVt/TVc)×100, where TVt and TVc are the mean tumor volume (or weight) of treated and control groups.

In some embodiments, the anti-LAG-3 antibody is designed for treating various cancers. As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "tumor" as used herein refers to cancerous cells, e.g., a mass of cancerous cells. Cancers that can be treated or diagnosed using the methods described herein include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. In some embodiments, the agents described herein are designed for treating or diagnosing a carcinoma in a subject. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the cancer is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

In some embodiments, the anti-LAG-3 antibody is designed for the treating melanoma, non-small cell lung carcinoma (NSCLC), small cell lung cancer (SCLC), bladder cancer, breast cancer, and/or prostate cancer (e.g., metastatic hormone-refractory prostate cancer).

The present disclosure also relates to the use of the animal model generated through the methods as described herein in the development of a product related to an immunization processes of human cells, the manufacturing of a human antibody, or the model system for a research in pharmacology, immunology, microbiology and medicine.

In some embodiments, the disclosure provides the use of the animal model generated through the methods as described herein in the production and utilization of an animal experimental disease model of an immunization processes involving human cells, the study on a pathogen, or the development of a new diagnostic strategy and/or a therapeutic strategy.

The disclosure also relates to the use of the animal model generated through the methods as described herein in the screening, verifying, evaluating or studying the LAG-3 gene function, human LAG-3 antibodies, drugs for human LAG-3 targeting sites, the drugs or efficacies for human LAG-3 targeting sites, the drugs for immune-related diseases and antitumor drugs.

Genetically Modified Animal Model with Two or More Human or Chimeric Genes

The present disclosure further relates to methods for generating genetically modified animal model with two or more human or chimeric genes. The animal can comprise a human or chimeric LAG-3 gene and a sequence encoding an additional human or chimeric protein.

In some embodiments, the additional human or chimeric protein can be programmed cell death protein 1 (PD-1), cytotoxic T-lymphocyte-associated protein 4 (CTLA-4), T-cell immunoglobulin and mucin-domain containing-3 (TIM-3), B And T Lymphocyte Associated (BTLA), Programmed Cell Death 1 Ligand 1 (PD-L1), TNF Receptor Superfamily Member 9 (4-1BB), CD27, CD28, CD47, T-Cell Immunoreceptor With Ig And ITIM Domains (TIGIT), CD27, Glucocorticoid-Induced TNFR-Related Protein (GITR), or TNF Receptor Superfamily Member 4 (TNFRSF4; or OX40).

The methods of generating genetically modified animal model with two or more human or chimeric genes (e.g., humanized genes) can include the following steps:
(a) using the methods of introducing human LAG-3 gene or chimeric LAG-3 gene as described herein to obtain a genetically modified non-human animal;

(b) mating the genetically modified non-human animal with another genetically modified non-human animal, and then screening the progeny to obtain a genetically modified non-human animal with two or more human or chimeric genes.

In some embodiments, in step (b) of the method, the genetically modified animal can be mated with a genetically modified non-human animal with human or chimeric PD-1, CTLA-4, TIM-3, BTLA, PD-L1, 4-1BB, CD27, CD28, CD47, TIGIT, CD27, GITR, or OX40. Some of these genetically modified non-human animals are described, e.g., in PCT/CN2017/090320, PCT/CN2017/099577, PCT/CN2017/099575, PCT/CN2017/099576, PCT/CN2017/099574, PCT/CN2017/106024; each of which is incorporated herein by reference in its entirety.

In some embodiments, the LAG-3 humanization is directly performed on a genetically modified animal having a human or chimeric PD-1, CTLA-4, BTLA, TIM-3, PD-L1, 4-1BB, CD27, CD28, CD47, TIGIT, CD27, GITR, or OX40 gene.

As these proteins may involve different mechanisms, a combination therapy that targets two or more of these proteins thereof may be a more effective treatment. In fact, many related clinical trials are in progress and have shown a good effect. The genetically modified animal model with two or more human or humanized genes can be used for determining effectiveness of a combination therapy that targets two or more of these proteins, e.g., an anti-LAG-3 antibody and an additional therapeutic agent for the treatment of cancer. The methods include administering the anti-LAG-3 antibody and the additional therapeutic agent to the animal, wherein the animal has a tumor; and determining the inhibitory effects of the combined treatment to the tumor.

In some embodiments, the animal further comprises a sequence encoding a human or humanized programmed cell death protein 1 (PD-1), or a sequence encoding a human or humanized CTLA4. In some embodiments, the additional therapeutic agent is an anti-PD-1 antibody (e.g., nivolumab, pembrolizumab, avelumab, durvalumab, atezolizumab) or an CTLA-4 antibody. In some embodiments, the tumor comprises one or more tumor cells that express MHC II, CD80, CD86, PD-L1 or PD-L2.

In some embodiments, the combination treatment is designed for treating various cancer as described herein, e.g., melanoma, non-small cell lung carcinoma (NSCLC), small cell lung cancer (SCLC), bladder cancer, and/or prostate cancer (e.g., metastatic hormone-refractory prostate cancer).

In some embodiments, the methods described herein can be used to evaluate the combination treatment with some other methods. The methods of treating a cancer that can be used alone or in combination with methods described herein, include, e.g., treating the subject with chemotherapy, e.g., campothecin, doxorubicin, cisplatin, carboplatin, procarbazine, mechlorethamine, cyclophosphamide, adriamycin, ifosfamide, melphalan, chlorambucil, bisulfan, nitrosurea, dactinomycin, daunorubicin, bleomycin, plicomycin, mitomycin, etoposide, verampil, podophyllotoxin, tamoxifen, taxol, transplatinum, 5-flurouracil, vincristin, vinblastin, and/or methotrexate. Alternatively or in addition, the methods can include performing surgery on the subject to remove at least a portion of the cancer, e.g., to remove a portion of or all of a tumor(s), from the patient.

EXAMPLES

The invention is further described in the following examples, which do not limit the scope of the invention described in the claims.

Materials and Methods

The following materials were used in the following examples.

Ambion™ in vitro transcription kit was purchased from Ambion. Catalog number is AM1354.

E. coli TOP10 competent cells were purchased from the Tiangen Biotech (Beijing) Co. Catalog number is CB104-02.

EcoRI, Scat, HindIII, BamHI, XhoI, EcoRV, SaiI, and BbsI were purchased from NEB. Catalog numbers are R3101M, R3122M, R3104M, R3136M, R0146M, R3195M, R3138M, and R0539L.

Kanamycin was purchased from Amresco. Catalog number is 0408.

Cas9 mRNA was obtained from SIGMA. Catalog number is CAS9MRNA-1EA.

AIO kit was obtained from Beijing Biocytogen Co., Ltd. Catalog number is BCG-DX-004.

UCA kit was obtained from Beijing Biocytogen Co., Ltd. Catalog number is BCG-DX-001.

C57BL/6 mice were purchased from the China Food and Drugs Research Institute National Rodent Experimental Animal Center.

B-hPD-1 mice, B-hCTLA-4 mice were obtained from Beijing Biocytogen Co., Ltd.

Mouse colon cancer cell line MC38 was purchased from Shanghai Enzyme Research Biotechnology Co., Ltd.

Anti-mouse CD3 antibody was obtained from BD. Catalog number is 563123.

PE labeled anti-mouse CD223 (LAG-3) antibody (mLAG3 PE) was obtained from Biolegend. Catalog number is 125208.

Alexa Fluor® 647 labeled anti-human CD223 (LAG-3) antibody (hLAG3 Alexa Fluor 647) was obtained from Biolegend. Catalog number is 369304.

Monoclonal anti-human LAG-3 antibody 3DS223H (hLAG3 APC) was obtained from eBioscience. Catalog number is 17-2239-42.

PerCP/Cy5.5 labeled anti-mouse TCR β chain antibody (mTcRβ PerCP) was obtained from Biolegend. Catalog number is 109228.

PE labeled anti-mouse CD279 (PD-1) antibody (mPD-1 PE) was obtained from Biolegend. Catalog number is 109104.

FITC labeled anti-human CD279 (PD-1) antibody (hPD-1 FITC) was obtained from Biolegend. Catalog number is 329904.

The Flow Cytometer was purchased from BD Biosciences; model FACS Calibur™.

Example 1: Construction of pT7-LAG-5 and pT7-LAG-12

The target sequence determines the targeting specificity of small guide RNA (sgRNA) and the efficiency of Cas9 cleavage at the target gene. Therefore, target sequence selection is important for sgRNA vector construction.

The 5'-terminal targeting sites (sgRNA1 to sgRNA7) and the 3'-terminal targeting sites (sgRNA8 to sgRNA14) were designed and synthesized. The 5'-terminal targeting sites and the 3'-terminal targeting sites are located on exon 2 and exon 3 of mouse LAG-3 gene respectively, and the targeting site sequences on LAG-3 for each sgRNA is as follows:

sgRNA-1 targeting sequence:
(SEQ ID NO: 1)
5'-GTTCCACTAGTTGTGTCTTCAGG-3' sgRNA-2 targeting sequence:
(SEQ ID NO: 2)
5'-GGCCCTGAAGACACAACTAG TGG-3' sgRNA-3 targeting sequence:
(SEQ ID NO: 3)
5'-ACCACGGGGAGCTCTTTCCCAGG-3' sgRNA-4 targeting sequence:
(SEQ ID NO: 4)
5'-CTAGTTGTGTCTTCAGGGCCTGG-3' sgRNA-5 targeting sequence:
(SEQ ID NO: 5)
5'-GCCTGGGAAAGAGCTCCCCGTGG-3' sgRNA-6 targeting sequence:
(SEQ ID NO: 6)
5'-CCTCCTGGGCCCACACCACGGGG-3' sgRNA-7 targeting sequence:
(SEQ ID NO: 7)
5'-GGAAAGAGCTCCCCGTGGTGTGG-3' sgRNA-8 targeting sequence:
(SEQ ID NO: 8)
5'-TCGAGGCCTGGCCGACGCGCAGG-3' sgRNA-9 targeting sequence:
(SEQ ID NO: 9)
5'-TCTCCGCCTGCGCGTCGGCCAGG-3' sgRNA-10 targeting sequence:
(SEQ ID NO: 10)
5'-AGGCCTGGCCGACGCGCAGGCGG-3' sgRNA-11 targeting sequence:
(SEQ ID NO: 11)
5'-TGCAGTCTCCGCCTGCGCGTCGG-3' sgRNA-12 targeting sequence:
(SEQ ID NO: 12)
5'-AGGAGAGGGCGCGGTTCGGGAGG-3' sgRNA-13 targeting sequence:
(SEQ ID NO: 13)
5'-GCGGTTCGGGAGGCGCACGGTGG-3' sgRNA-14 targeting sequence:
(SEQ ID NO: 14)
5'-TGCAGGAGAGGGCGCGGTTCGGG-3'

The UCA kit was used to detect the activities of sgRNAs (FIGS. 1A and 1B), sgRNA9 was not detected due to the incorrect sequence. The results show that the guide sgRNAs have different activities. Two of them (sgRNA5 and sgRNA12) were selected for follow-up experiments. TAGG was added to the 5' end to obtain a forward oligonucleotide sequence, and its complementary strand was added with AAAC to obtain a reverse oligonucleotide sequence. After annealing, they were respectively digested by restriction enzyme (BbsI) and ligated to pT7-sgRNA plasmid to obtain the expression vectors pT7-LAG-5 and pT7-LAG-12.

TABLE 3

| sgRNA5 and sgRNA12 sequences | |
|---|---|
| sgRNA5 sequences | |
| SEQ ID NO: 15 | Upstream: 5'-CCTGGGAAAGAGCTC CCCG-3' |
| SEQ ID NO: 16 (adding TAGG to obtain a forward oligonucleotide sequence) | Upstream: 5'-TAGGCCTGGGAAAGA GCTCCCCG-3' |
| SEQ ID NO: 17 | Downstream: 5'-CGGGGAGCTCTTT CCCAGG-3' |
| SEQ ID NO: 18 (complementary strand was added with AAAC to obtain a reverse oligonucleotide sequence) | Downstream: 5'-AAACCGGGGAGCT CTTTCCCAGG-3' |
| sgRNA12 sequences | |
| SEQ ID NO: 19 | Upstream: 5'-AGAGGGCGCGGTTCG GG-3' |
| SEQ ID NO: 20 (adding TAGG to obtain a forward oligonucleotide sequence) | Upstream: 5'-TAGGAGAGGGCGCGG TTCGGG-3' |
| SEQ ID NO: 21 | Downstream: 5'-CCCGAACCGCGCC CTCT-3' |
| SEQ ID NO: 22 (complementary strand was added with AAAC to obtain a reverse oligonucleotide sequence) | Downstream: 5'-AAACCCCGAACCG CGCCCTCT-3' |

TABLE 4

| The ligation reaction conditions (10 μL) | |
|---|---|
| Double stranded fragment | 1 μL (0.5 μM) |
| pT7-sgRNA vector | 1 μL (10 ng) |
| T4 DNA Ligase | 1 μL (5 U) |
| 10 × T4 DNA Ligase buffer | 1 μL |
| 50% PEG4000 | 1 μL |
| H₂O | Add to 10 μL |

Reaction Conditions:

The ligation reaction was carried out at room temperature for 10 to 30 minutes. The ligation product was then transferred to 304 of TOP10 competent cells. The cells were then plated on a petri dish with Kanamycin, and then cultured at 37° C. for at least 12 hours and then two clones were selected and added to LB medium with Kanamycin (5 ml), and then cultured at 37° C. at 250 rpm for at least 12 hours.

Randomly selected clones were sequenced, so as to verify their sequences. The correct expression vectors pT7-LAG-5 and pT7-LAG-12 were selected for subsequent experiments.

Source of pT7-sgRNA Plasmid

Figure 2:
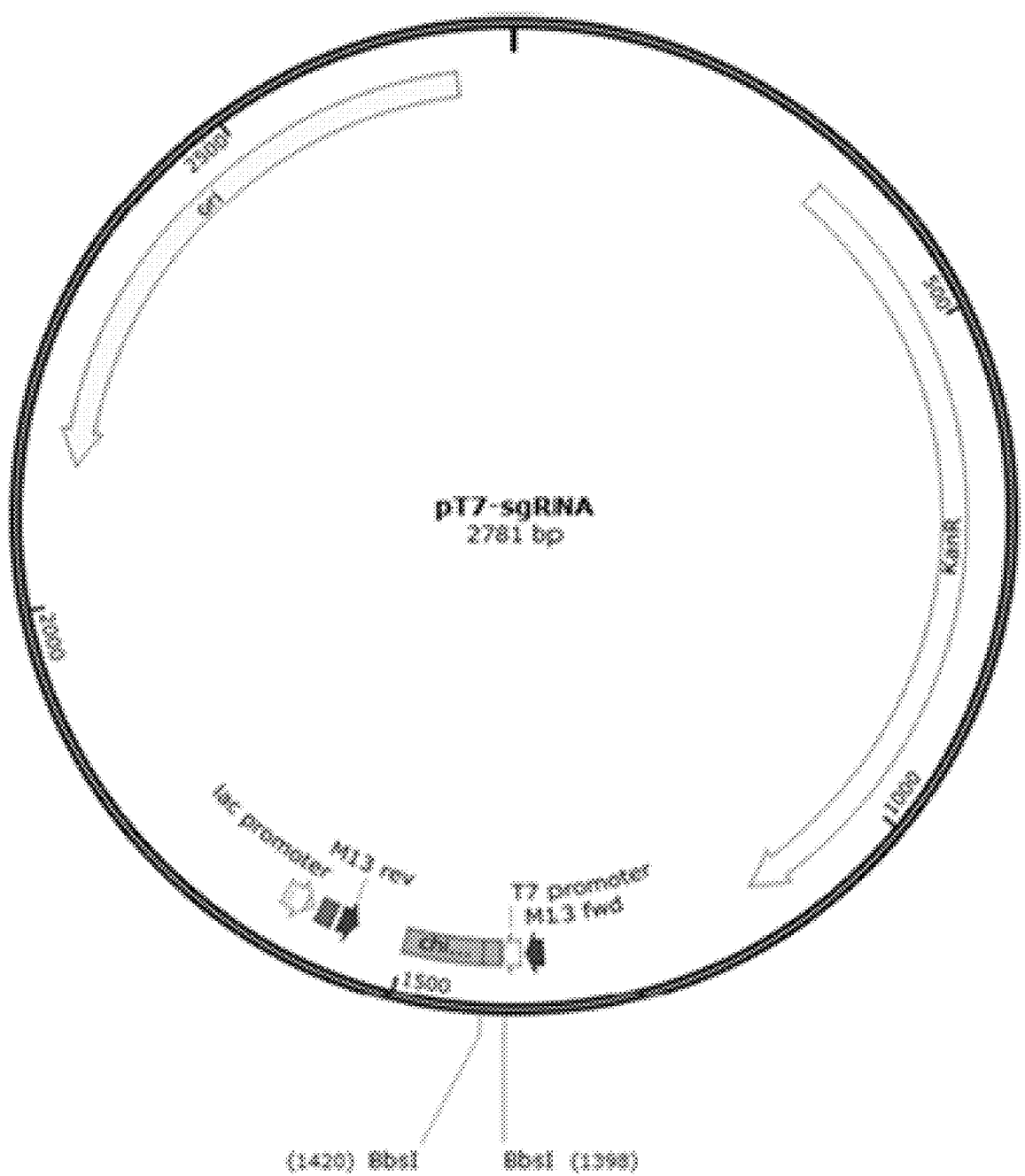
FIG. 2 is a schematic diagram showing pT7-sgRNA plasmid map.

PT7-sgRNA vector map is shown in FIG. 2. The plasmid backbone was obtained from Takara (Catalog No. 3299). The DNA fragment containing T7 promoter and sgRNA scaffold was synthesized by a plasmid synthesis company, and linked to the backbone vector by restriction enzyme digestion (EcoRI and BamHI) and ligation. The target plasmid was confirmed by the sequencing results.

The DNA fragment containing the T7 promoter and sgRNA scaffold (SEQ ID NO: 23):

```
GAATTCTAATACGACTCACTATAGGGGGTCTTCGAGAAGACCTGTTTTAG
AGCTAGAAATAGCAAGTTAAAATAAGGCTAGTCCGTTATCAACTTGAAAA
AGTGGCACCGAGTCGGTGCTTTTAAAGGATCC
```

Example 2. Construction of Vector pClon-4G-LAG

A partial coding sequence of the mouse LAG-3 gene (Gene ID: 16768) from exon 2 and exon 3 (based on the transcript of NCBI accession number NM_008479.2→NP_032505.1 whose mRNA sequence is shown in SEQ ID NO: 24, and the corresponding protein sequence is shown in SEQ ID NO: 25) was replaced with a corresponding coding sequence of human homologous LAG-3 gene (Gene ID: 3902) (based on the transcript of NCBI accession number NM_002286.5-*NP_002277.4, whose mRNA sequence was shown in SEQ ID NO: 26, and the corresponding protein sequence is shown in SEQ ID NO: 27). The comparison between the mouse LAG-3 and human LAG-3 is shown in FIG. 3A, and the finally obtained humanized LAG-3 gene is shown in FIG. 3B, the humanized mouse LAG-3 gene DNA sequence (chimeric LAG-3 gene DNA) is shown in SEQ ID NO: 28.

TTGTGTCTTCAGGG*CCAGGGGCTGAGGTCCCGGTGGTGTGGGCCCAGGAG*
*GGGGCTCCTGCCCAGCTCCCCTGCAGCCCCACAATCCCCCTCCAGGATCT*
*CAGCCTTCTGCGAAGAGCAGGGGTCACTTGGCAGCATCAGCCAGACAGGT*
*ATGCACCCCAAACTTGGGCAACAGGACCTCCGAATCCAGCACTCAACCCC*
*ACACCCGTGCCGGTCCTCTGTCCCCTGCCCTGAGGTGTCACTCCCTCTGA*
*AGCCAGTGACCCAGTCTCCCTGCCCTCGCTTGCACCGTTCCTGCCCTTGC*
*TCTGCAATCAGCGACCCTCACGCCAGCATCCCTTCTCTCCAGAAGTGGAT*
*GCGGCCAGTCCAACAGAGGGGTCGGGCGTGAGGGGACGGTTGGTGGTCAA*
*GAGAACTCTTGGGGCGGGCTTTCTCATCCTCAACGGGTGGCTGCCTGCAT*
*CCTCCCGGGCTTCCTACCCCTGGAGCTTCTCAACTCCATTCTCTTTCCCG*
*CCCAGTGGCCCGCCCGCTGCCGCCCCCGGCCATCCCCTGGCCCCCGGCCC*
*TCACCCGGCGGCGCCCTCCTCCTGGGGGCCCAGGCCCCGCCGCTACACGG*
*TGCTGAGCGTGGGTCCCGGAGGCCTGCGCAGCGGGAGGCTGCCCCTGCAG*
*CCCCGCGTCCAGCTGGATGAGCGCGGCCGGCAGCGCGGGGACTTCTCGCT*
*ATGGCTGCGCCCAGCCCGGCGCGCGGACGCCGGCGAGTACCGCGCCGCGG*
*TGCACCTCAGGGACCGCGCCCTCTCCTGCCGCCTCCGTCTGCGCCTGGGC*
CAGGCCTCGA

SEQ ID NO: 28 lists only the portion of DNA sequence involved in the modification, wherein the italicized underlined region is the human LAG-3 gene sequence fragment.

The coding region sequence, mRNA sequence and the encoded protein sequence thereof of the modified humanized LAG-3 are respectively shown in SEQ ID NO: 29, SEQ ID NO: 30, and SEQ ID NO: 31.

To the extent that either human LAG-3 or mouse LAG-3 has more than one isoforms or transcripts, the methods as described herein can be applied to other isoforms or transcripts.

A targeting strategy involving a vector comprising the 5' end homologous arm, human LAG-3 gene fragment, 3' homologous arm as shown in FIG. 3C is also developed. The process is as follows:

(1). Design upstream primers of homologous recombination fragments, and downstream primers matching therewith, as well as other related sequences. Specifically:

5' end homologous arm (SEQ ID NO: 32), nucleotide sequence of the positions from 124911766 to 124910898 of the NCBI accession number NC_000072.6 as follows:

Upstream primer (SEQ ID NO: 33):
F: 5'-tttaagaaggagatatacatggaattcgaatcagcccctcaca ctttccac-3'

Downstream primer (SEQ ID NO: 34):
R: 5'-cctcagcccctggccctgaagacacaactagtggaaca-3'

(2). Design the primers and related sequences of the desired conversion region. Human DNA fragment (783 bp) (SEQ ID NO: 35) is the nucleotide sequence from positions 6773206 to 6773988 of the NCBI accession number NC_000012.12.

The upstream primer (SEQ ID NO: 36) is:
F: 5'-gtgtcttcagggccaggggctgaggtcccggtggtg-3'

The downstream primer (SEQ ID NO: 37) is:
R: 5'-tcgaggcctggcccaggcgcagacggaggcggcag-3'

(3). Design the upstream primers of the homologous recombination fragment and the downstream primers matching therewith, as well as other related sequences. Specifically:

3' homologous arm (SEQ ID NO: 38), which was the nucleotide sequence from positions 124910116 to 124908702 of the NCBI accession number NC_000072.6.

Upstream primer (SEQ ID NO: 39):
F: 5'-cgtctgcgcctgggccaggcctcgagtaggtggg-3'

Downstream primer (SEQ ID NO: 40):
R: 5'-ttgttagcagccggatctcagggatccccagagggtggagacat caaggaag-3'

C57BL/6 mouse DNA is used as the template to carry out PCR amplification for the 5'-terminal homologous arm fragment and the 3'-terminal homologous arm fragment. Human DNA is used as the template to carry out PCR amplification for the DNA fragment, and the AIO kit is used to ligate the fragments to the pClon-4G plasmid provided by the kit, so as to obtain the vector pClon-4G-LAG.

Example 3. Verification of Vector pClon-4G-LAG

Figure 4:
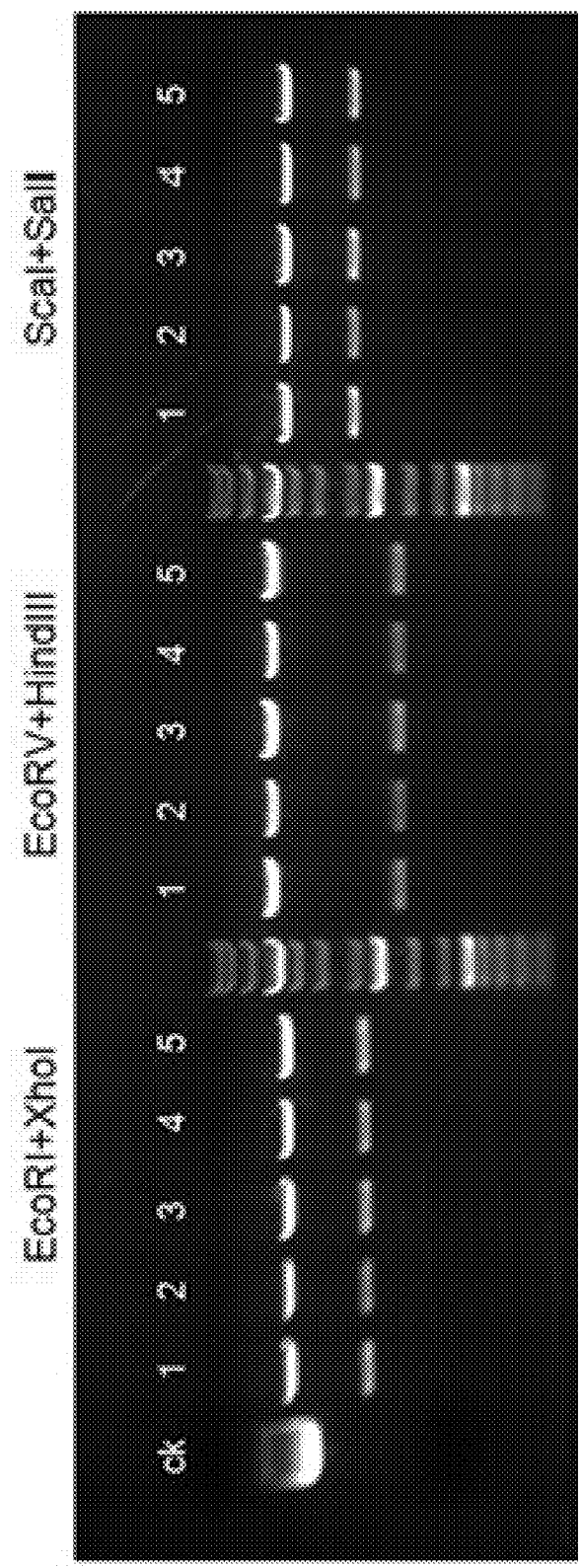
FIG. 4 shows pClon-4G-LAG plasmid digestion result (CK is undigested plasmid).

Five pClon-4G-LAG clones were randomly selected and identified by three sets of enzymes. Among them, EcoRI+XhoI should generate 1666 bp+4137 bp fragments, EcoRV+HindIII should generate 1097 bp+4706 bp fragments, ScaI+SalI should generate 1784 bp+4019 bp fragments. The results were in line with the expectations (FIG. 4). The sequences of Plasmids 1 and 2 were further verified by sequencing.

Example 4. Microinjection and Embryo Transfer

The pre-mixed Cas9 mRNA, pClon-4G-LAG plasmid and in vitro transcription products of pT7-LAG-5, pT7-LAG-12 plasmids were injected into the cytoplasm or nucleus of mouse fertilized eggs (C57BL/6 background) with a microinjection instrument (using Ambion in vitro transcription kit to carry out the transcription according to the method provided in the product instruction). The embryo microinjection was carried out according to the method described, e.g., in A. Nagy, et al., "Manipulating the Mouse Embryo: A Laboratory Manual (Third Edition)," Cold Spring Harbor Laboratory Press, 2003. The injected fertilized eggs were then transferred to a culture medium for a short time culture, and then was transplanted into the oviduct of the recipient mouse to produce the genetically modified humanized mice (F0 generation). The mice population was further expanded by cross-mating and self-mating to establish stable mouse lines. The humanized mouse was named as B-hLAG-3 mouse.

Example 5. Verification of Genetically Modified Humanized Mouse Model

1. Genotype Determination for F0 Generation Mice

PCR analysis was performed for mouse tail genomic DNA of F0 generation mice. The primers for PCR-1 were located on the left side of the 5' homologous arm, the primers for PCR-4 were located on the right side of the 3' homologous arm; in addition, the primers for PCR-2 and PCR-3 were located on the humanized fragment, which are shown below:

```
5' terminus primers:
PCR-1 (SEQ ID NO: 41): 5'-agcattcacacagggtggggaatt
t-3'

PCR-2 (SEQ ID NO: 42): 5'-ggcgtgagggtcgctgattg-3'

3' terminus primers:
PCR-3 (SEQ ID NO: 43): 5'-gacctccgaatccagcactcaac
c-3'

PCR-4 (SEQ ID NO: 44): 5'-aggagtccacttggcaatgagcaa
a-3'
```

If the recombinant vector has the correct insertion, there should be one PCR band from 5' terminus primers and one PCR band from the 3' terminus primers. The length of the 5' terminus product should be 2049 bp, and the length of the 3' terminus product should be 2206 bp.

TABLE 5

| The PCR reaction system (20 μL) | |
|---|---|
| 10 × buffer | 2 μL |
| dNTP (2 mM) | 2 μL |
| MgSO$_4$ (25 mM) | 0.8 μL |
| Upstream primer (10 μM) | 0.6 μL |
| Downstream primer (10 μM) | 0.6 μL |
| Mouse tail genomic DNA | 200 ng |
| KOD-Plus-(1 U/μL) | 0.6 μL |

TABLE 6

| The PCR reaction conditions | | |
|---|---|---|
| Temperature | Time | Cycles |
| 94° C. | 5 min | 1 |
| 94° C. | 30 sec | 15 |
| 67° C. (−0.7° C./cycle) | 30 sec | |
| 68° C. | 1 kb/min | |

TABLE 6-continued

| The PCR reaction conditions | | |
|---|---|---|
| Temperature | Time | Cycles |
| 94° C. | 30 sec | 25 |
| 56° C. | 30 sec | |
| 68° C. | 1 kb/min | |
| 68° C. | 10 min | 1 |
| 4° C. | 10 min | 1 |

Figure 5:
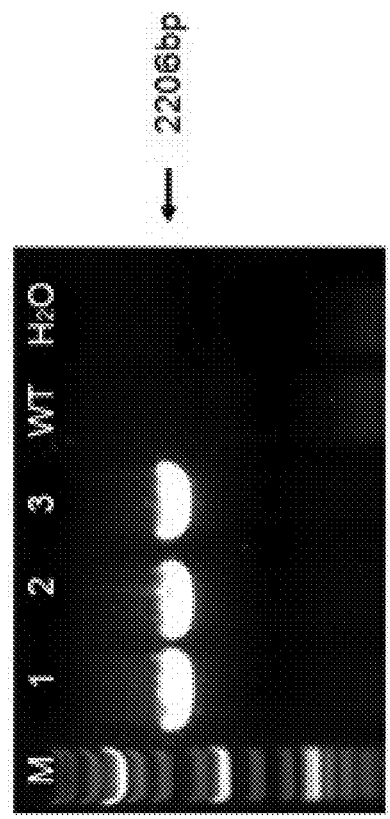
FIG. 5 shows PCR identification result of samples collected from tails of F0 generation mice (M is the Marker; WT is wildtype; mice labeled with No. 1, 2 and 3 are positive).
Figure 5:
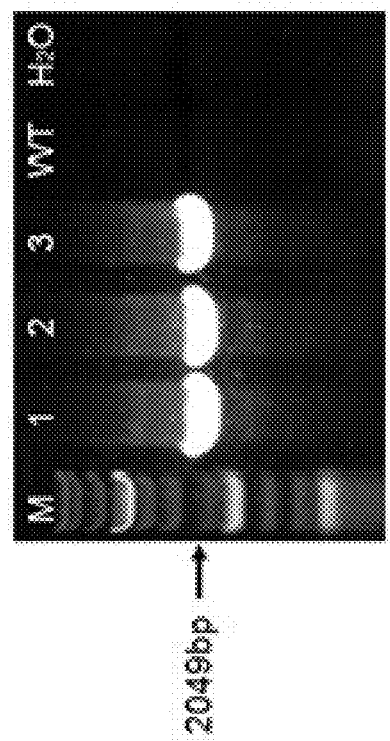

The verification results for three F0 generation mice are shown in FIG. 5.

2. Genotype Determination for F1 Generation Mice

Figure 6:
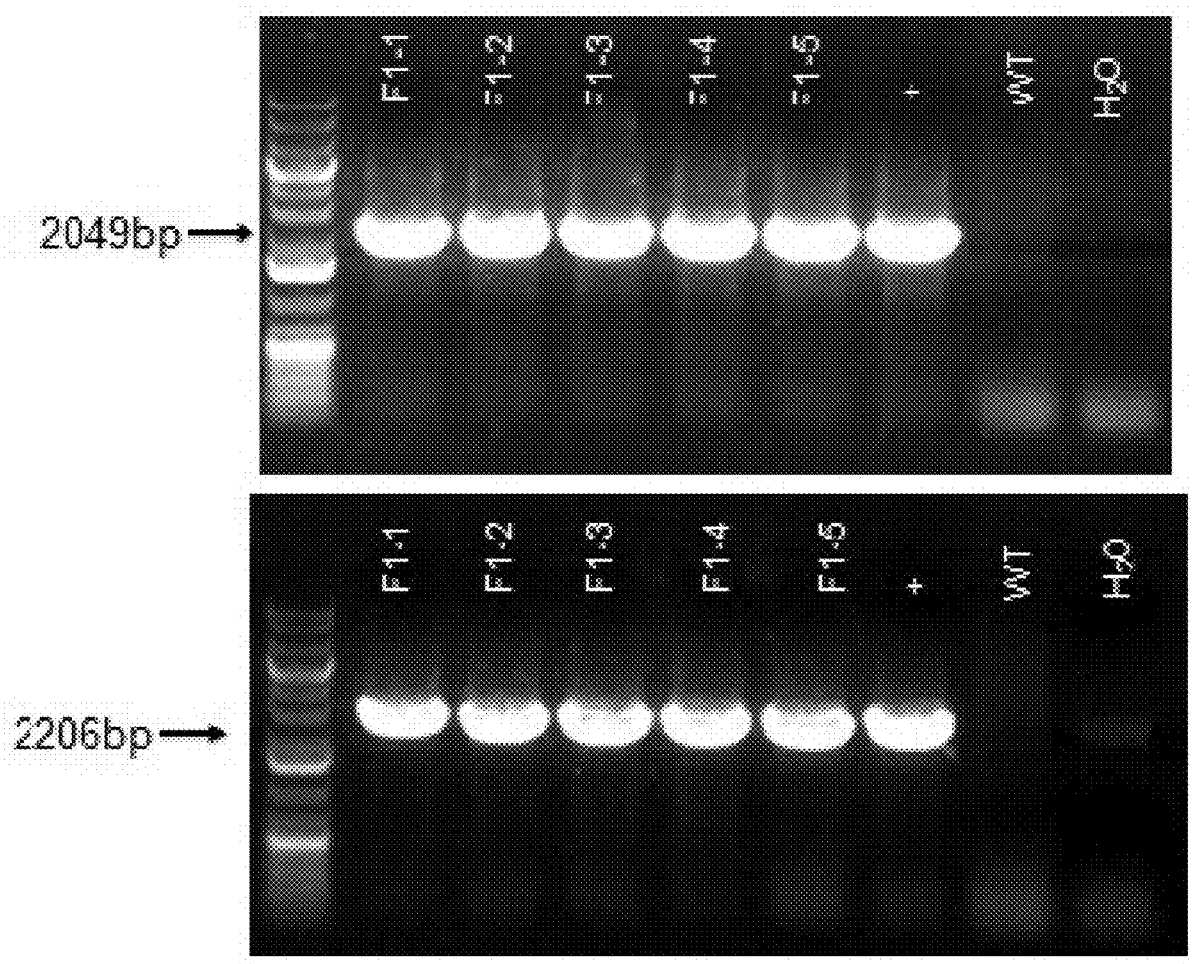
FIG. 6 shows PCR identification result of samples collected from tails of F1 generation mice (WT is wildtype; + is positive control; mice labeled with F1-1, F1-2, F1-3, F1-4, F1-5 are all positive).

F1 generation mice were obtained by cross-mating F0 generation mice with C57BL/6 mice. PCR was performed for four F1 generation mice with the same primers under the same conditions used for F0 verification. The results showed that all five F1 generation mice were positive (FIG. 6).

Five mice were further examined by Southern blotting to determine whether they had a random insertion. The genomic DNA was extracted from the mouse tail, and BamHI was used to digest the genomic DNA. The digestion products were transferred to membrane and hybridized. The probes P1 and P2 were located respectively outside of the 5' homologous arm, and on the 3' homologous arm. The primers for probe synthesis are as follows:

```
P1-F (SEQ ID NO: 45): 5'-ggccacttatcatcacttgccc-3'

P1-R (SEQ ID NO: 46): 5'-ggtggtaaaggggcctaggag-3'

P2-F (SEQ ID NO: 47): 5'-cagggagagcaatggctaggg-3'

P2-R (SEQ ID NO: 48): 5'-gctgaaaaactcatagaaatgggg
c-3'
```

The wildtype C57BL/6 mice would have a 6.3 kb band and a 10.2 kb band for probe P1 and probe P2 respectively. The genetically engineered homozygous mice should have a 16.6 kb band for either P1 or P2. The genetically engineered heterozygous mice should have a 6.3 kb band and a 16.6 kb band (P1 probe), or a 10.2 kb and a 16.6 kb band (P2 probe). No other band should be present.

Figure 7:
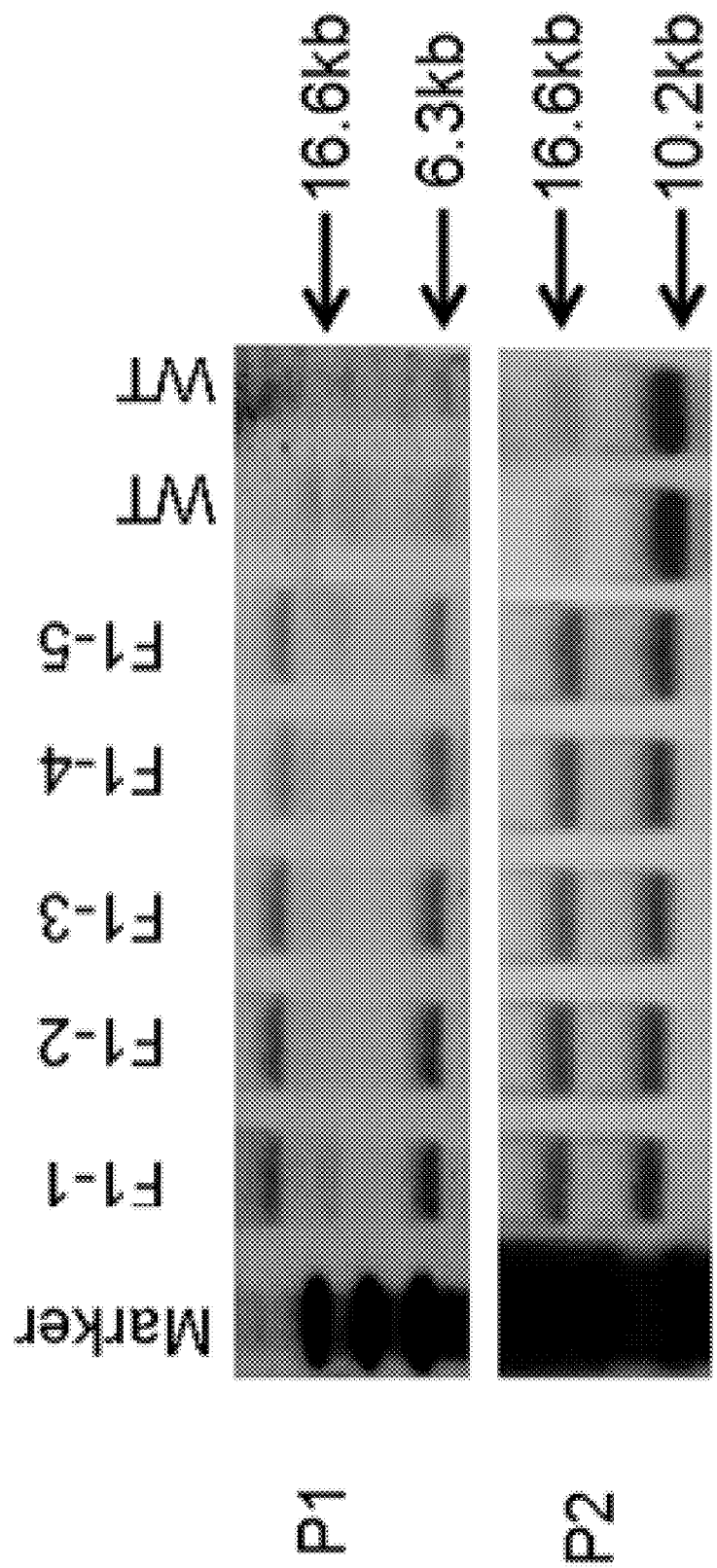
FIG. 7 shows Southern blot results for F1 generation mice by P1 and P2 probes (WT is wildtype). The results show that the mice labeled with F1-2, F1-3, and F1-4 had no random insertion.

The results are shown in FIG. 7. F1-2, F1-3, and F1-4 showed the expected bands for both the P1 probe and the P2 probe, with no other band, and without any random insertion. The results confirmed that F1-2, F1-3, and F1-4 were positive heterozygous mice with no random insertion.

It thus shows that this method can be used to generate humanized B-hLAG-3 mice with stable genetic modifications.

3. Protein Expression Analysis for Heterozygous F1 Generation Mouse

A humanized heterozygous F1 generation mouse was selected for this experiment. Wildtype C57BL/6 mice used as the control. 7.5 μg of mouse anti-CD3 antibody was injected intraperitoneally to the mice. The spleens were collected 24 hours after the injection, and the spleen samples were grinded. The ground samples were then passed through 70 μm cell mesh. The filtered cell suspensions were centrifuged and the supernatants were discarded. Erythrocyte lysis solution was added to the sample, which was lysed for 5 min and neutralized with PBS solution. The solution was centrifuged again and the supernatants were discarded. The cells were washed once with PBS.

Figures 8A, 8B, 8C, 8D, 8E, 8F, 8G, 8H, 8I:
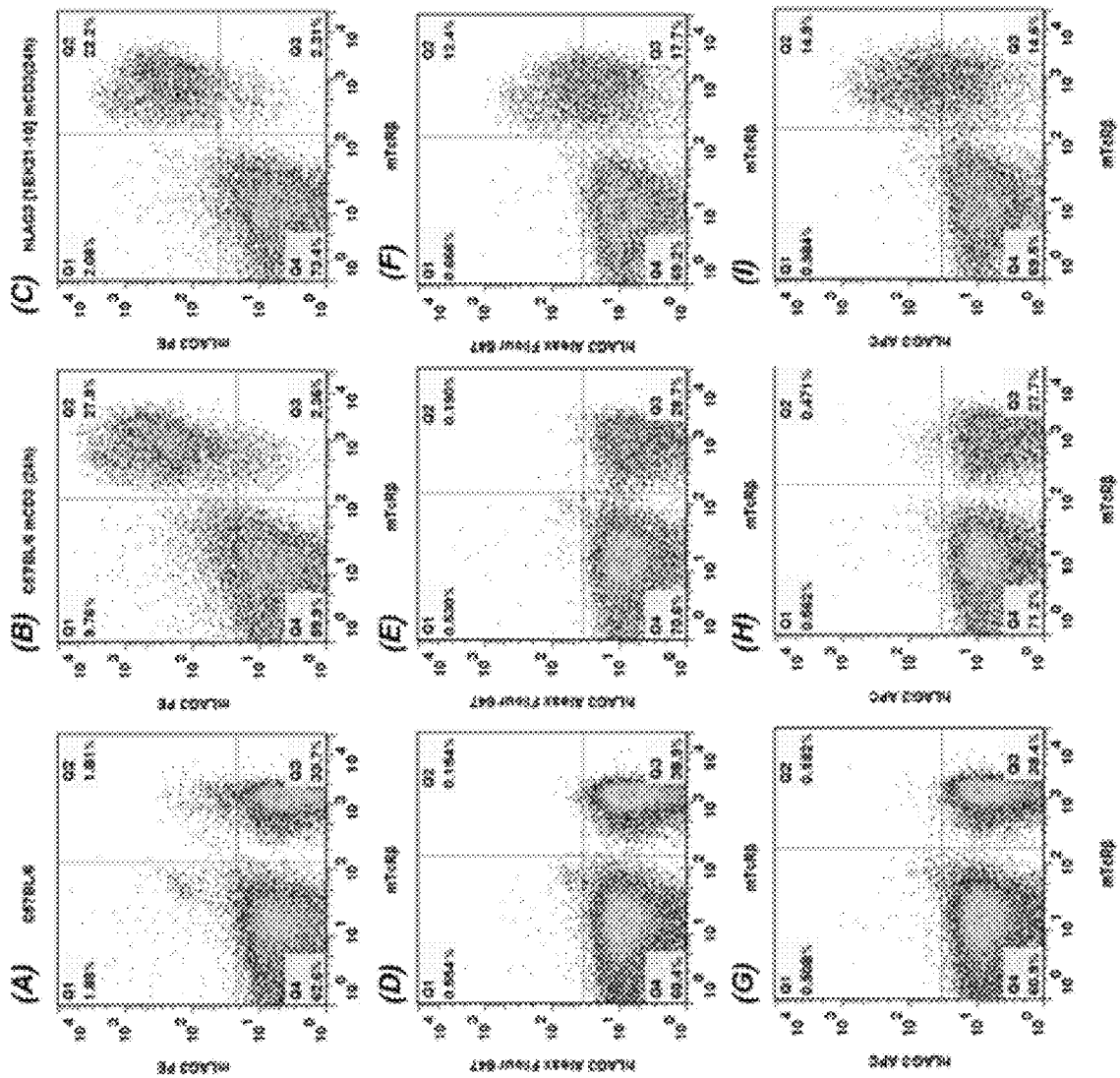
FIGS. 8A-8I are results of flow cytometry analysis for C57BL/6 mice and LAG-3 humanized mice. The anti-mouse CD3 antibody was used to stimulate the T cells in the spleens. Then the cells were labeled with anti-mouse LAG-3 antibody (mLAG3 PE.

The cells were then stained with (1) an anti-mTCRβ antibody and an anti-mouse LAG-3 antibody (mLAG3 PE; FIGS. 8A-8C); (2) an anti-mTCRβ antibody and an anti-human LAG-3 antibody (hLAG3 Alexa Fluor 647; FIGS. 8D-8F); or (3) an anti-mTCRβ antibody and an anti-human LAG-3 antibody (hLAG3 APC; FIGS. 8G-8I). The stained samples were washed in PBS once and analyzed by flow cytometry.

Results in FIGS. 8A-8I show that cells expressing humanized LAG-3 proteins were detected by anti-human LAG-3 antibodies in the spleens of humanized LAG-3 mice (FIGS. 8F and 8I). Cells expressing humanized LAG-3 proteins were not detected in the spleens of C57BL/6 mice (FIGS. 8D, 8E, 8G, and 8H).

Furthermore, the heterozygous humanized LAG-3 mice (F1) were mated with each other, producing homozygous humanized LAG-3 mice (B-hLAG-3). One homozygous B-hLAG-3 mouse (6 weeks) and two wildtype C57BL/6 mice were selected for flow cytometry analysis (FIGS. 9A-9I).

7.5 μg of mouse CD3 antibody was injected intraperitoneally to the homozygous B-hLAG-3 mouse and the control mice. The spleens were collected 24 hours after the injection, and the spleen samples were grinded. The ground samples were then passed through 70 μm cell mesh. The filtered cell suspensions were centrifuged and the supernatants were discarded. Erythrocyte lysis solution was added to the sample, which was lysed for 5 min and neutralized with PBS solution. The solution was centrifuged again and the supernatants were discarded. The cells were washed once with PBS.

Figures 9A, 9B, 9C, 9D, 9E, 9F, 9G, 9H, 9I:
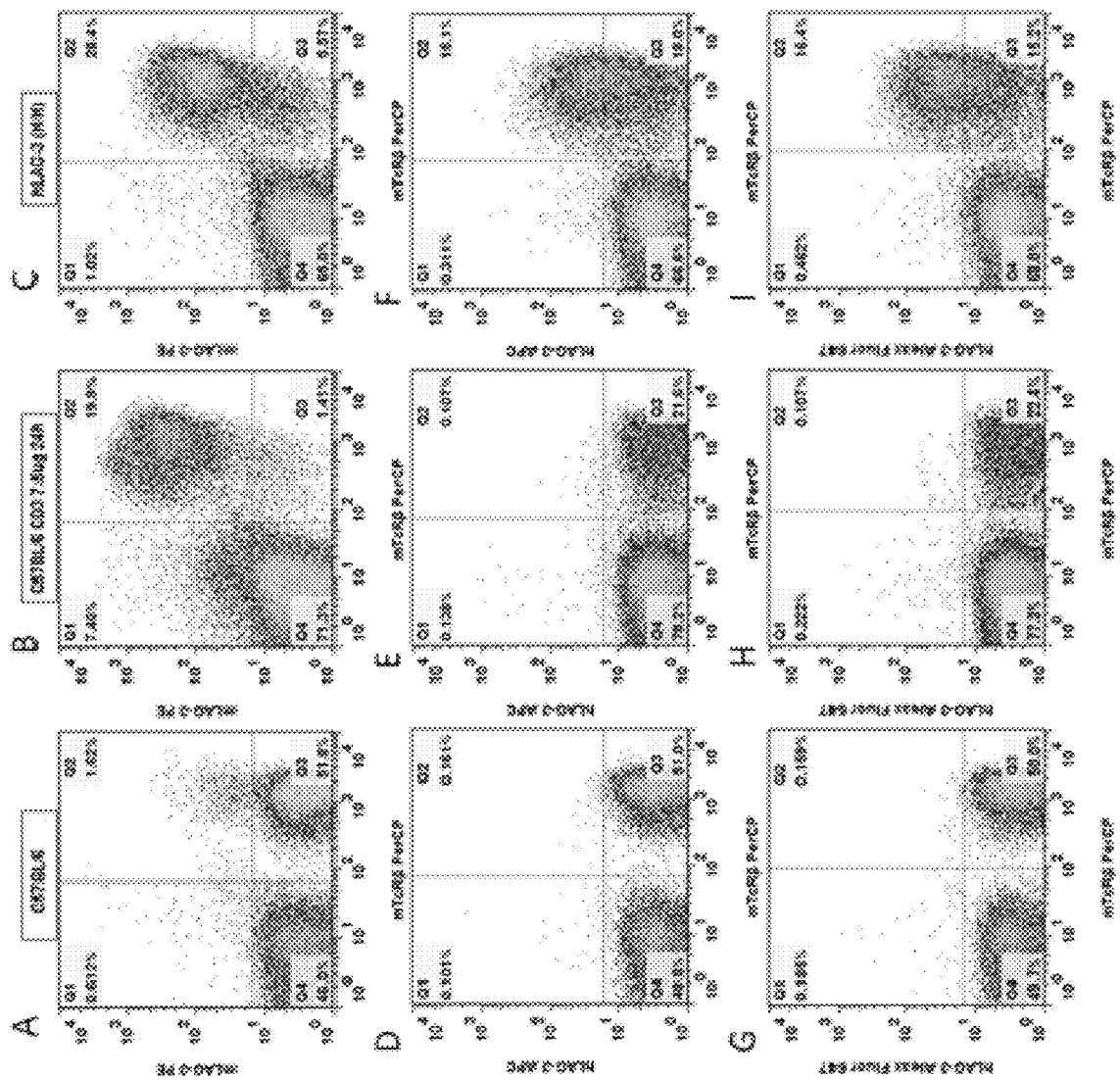
FIG. 9A-9I are results of flow cytometry analysis of C57BL/6 mice and homozygous humanized LAG-3 mice. The anti-mouse CD3 antibody was used to stimulate the T cells in the spleens. Then the cells were labeled with anti-mouse LAG-3 antibody (mLAG3 PE.

The cells were then stained with (1) an anti-mTCRβ antibody and an anti-mouse LAG-3 antibody (mLAG3 PE; FIGS. 9A-9C); (2) an anti-mTCRβ antibody and an anti-human LAG-3 antibody (hLAG-3 APC; FIGS. 9D-9F); or (3) an anti-mTCRβ antibody and an anti-human LAG-3 antibody (hLAG3 Alexa Fluor 647; FIGS. 9G-9I).

FIGS. 9A-9I show that cells expressing humanized LAG-3 were detected with anti-human LAG-3 antibody in the spleens of homozygous B-hLAG-3 mice stimulated with CD3 antibody (FIGS. 9F, 9I). No cell expressing humanized LAG-3 was detected in the spleens of C57BL/6 mice, either stimulated with CD3 antibody (FIGS. 9E and 9H), or without CD3 antibody stimulation (FIGS. 9D and 9G).

Example 6. LAG-3 Knockout Mice

Since the cleavage of Cas9 results in DNA double strands break, and the homologous recombination repair may result in insertion/deletion mutations, it is possible to obtain LAG-3 knockout mice when preparing the humanized LAG-3 mouse. A pair of primers was thus designed, located on the left side of the 5' end target site, and to the right side of the 3' end target site, which are shown as follows:

```
                                         (SEQ ID NO: 49)
F: 5'-GCTTTGGGAAGCTCCAGGTAAG-3'

(SEQ ID NO: 50)
R: 5'-CAAGGGATGGCACTCCCGCAGTAG-3'
```

Figure 10:
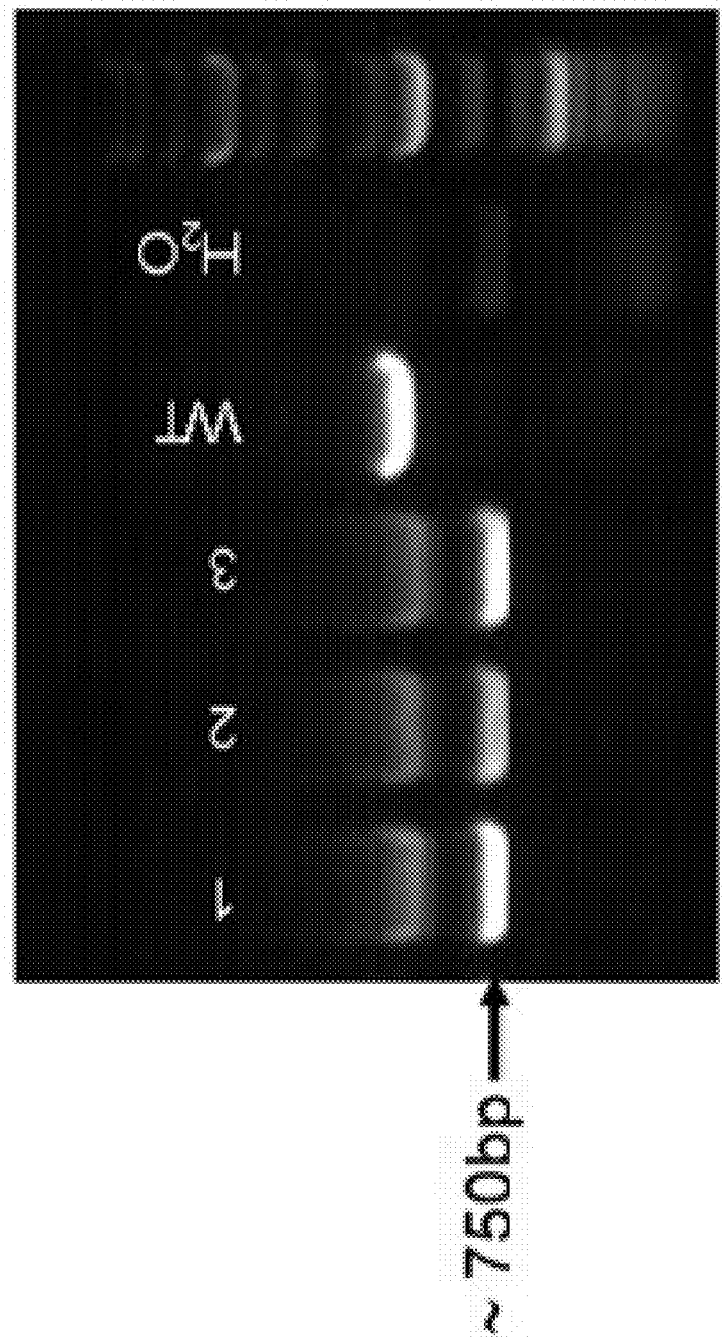
FIG. 10 shows PCR analysis results, wherein WT is wildtype C57BL/6 mouse; mice labeled No. 1, 2, and 3 were LAG-3 knockout mice.

The PRC reaction systems and conditions are listed in Table 5 and Table 6. Under these conditions, the wild type mice should have only one PCR band at approximately 1494 bp. The homozygous knockout mice should have only one band at approximately 750 bp. The results are shown in FIG. 10. The results confirmed successful generation of LAG-3 knockout mice.

Example 7. Pharmacological Validation of B-hLAG-3 Humanized Animal Model

B-hLAG-3 homozygous mice (4-6 weeks) were subcutaneously injected with mouse colon cancer cell MC38. When the tumor volume grew to about 100 mm³, the mice were randomly divided to a control group and three treatment groups (n=5/group). The treatment groups were randomly selected for treatment with anti-human LAG-3 antibodies (Ab-A, Ab-B, Ab-C) at 10 mg/kg; the control group was injected with an equal volume of blank solvent. The antibodies and control were administered through intraperitoneal injection once every three days for a total of three times. The tumor volume was measured twice a week and the body weight of the mice was weighed as well. Euthanasia was performed when the tumor volume of the mouse reached 3000 mm³.

Table 7 shows results for this experiment, including the tumor volumes at the day of grouping (Day 0), 10 days after grouping (Day 10), and at the end of the experiment (Day 17); the survival rate of the mice; the number of tumor-free mice (non-existence of tumor); the Tumor Growth Inhibition value ($TGI_{TV}$).

TABLE 7

|  |  | Tumor volume (mm³) | | | Survival | Non-existence of tumor | $TGI_{TV}$% |
|---|---|---|---|---|---|---|---|
|  |  | Day 0 | Day 10 | Day 17 |  |  |  |
| Control | G1 | 131 ± 7 | 527 ± 136 | 1344 ± 524 | 5/5 | 0/5 | N/A |
| Treatment | G2 (Ab-A) | 132 ± 3 | 472 ± 100 | 1762 ± 239 | 5/5 | 0/5 | N/A |
|  | G3 (Ab-B) | 132 ± 5 | 421 ± 83 | 1558 ± 434 | 5/5 | 0/5 | N/A |
|  | G4 (Ab-C) | 131 ± 11 | 396 ± 72 | 926 ± 141 | 5/5 | 0/5 | 34.5 |

Figure 11:
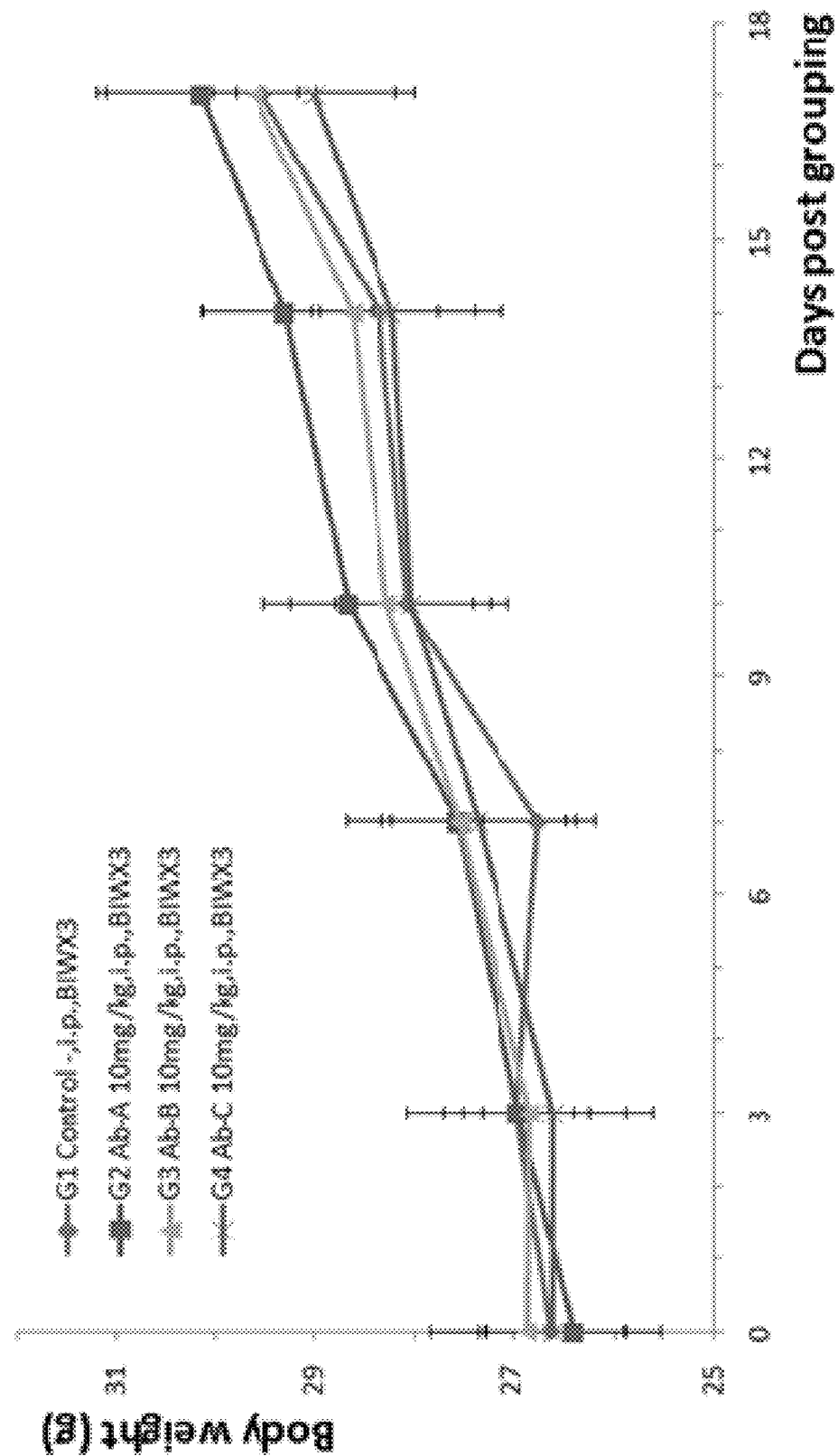
FIG. 11 shows results from experiments where mouse colon cancer cells MC38 were injected into B-hLAG-3 mice, followed by studies on antitumor efficacy of three anti-human LAG-3 antibodies (Ab-A, Ab-B, and Ab-C, 10 mg/kg). There was no significant difference in the average weight between the G1 control group and the G2-G4 treatment groups.
Figure 12:
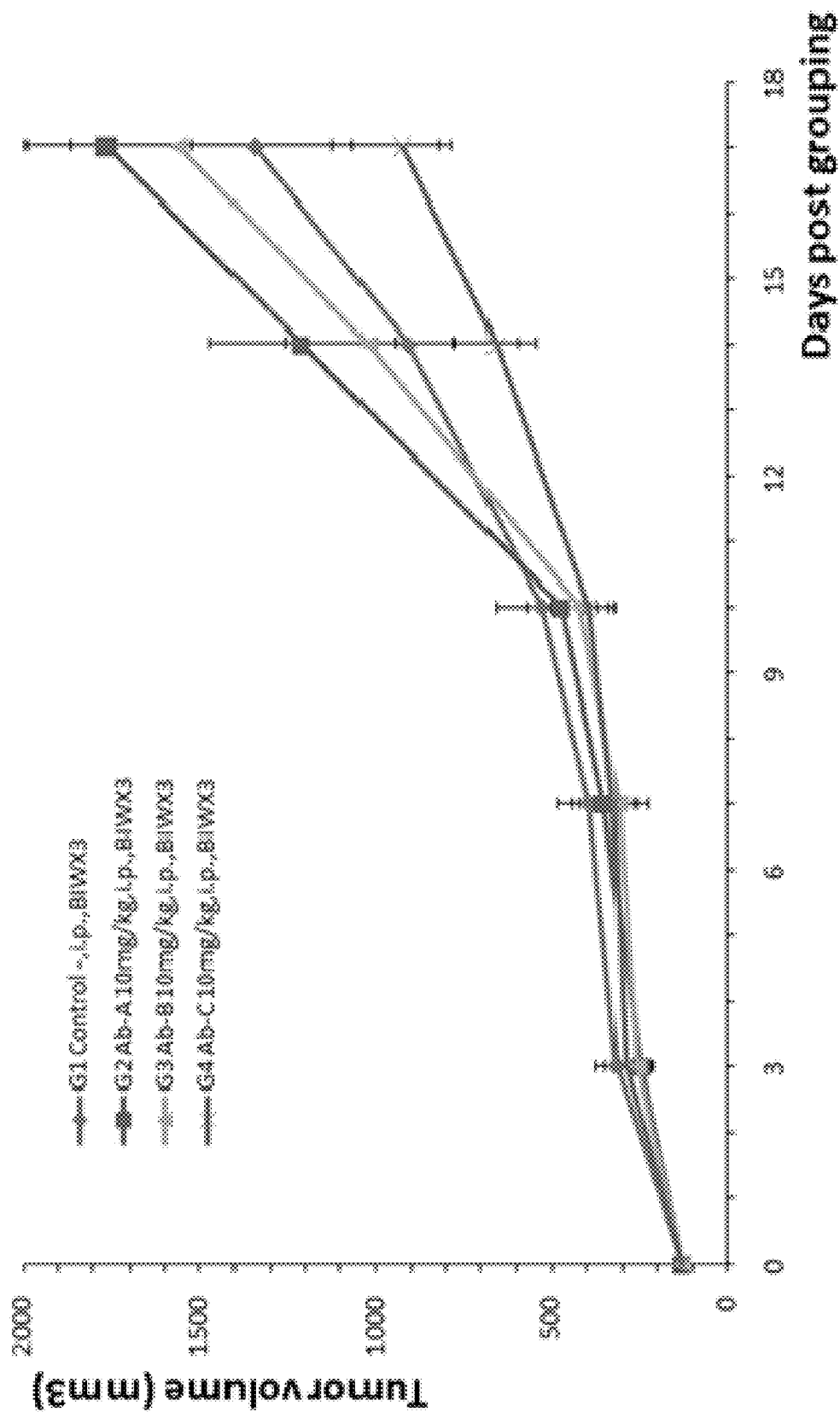
FIG. 12 shows results from experiments where mouse colon cancer cells MC38 were injected into B-hLAG-3 mice, followed by studies on antitumor efficacy of three anti-human LAG-3 antibodies (Ab-A, Ab-B, and Ab-C, 10 mg/kg). While the decease of tumor size in G2 and G3 groups were not significant, the tumor size in G4 group (treated with Ab-C) was significantly smaller compared to the G1 control group.

Overall, the animals in each group were healthy, with normal weight increase over the course of the experiment. The body weights of the treatment group mice and the control group mice were not significantly different from each other, indicating that the antibodies were well tolerated and safe to use without obvious toxicity (FIG. 11). The tumors in the control group mice continued growing during the experimental period (FIG. 12). Tumor sizes in the treatment groups G2 (Ab-A) and G3 (Ab-B) were not significantly different from the control group G1, while the tumor sizes in group G4 (Ab-C) mice were significantly smaller as compared to the control group mice (FIG. 12). The results indicated that the anti-human LAG-3 antibody Ab-C was able to inhibit tumor growth in vivo, with higher efficacy than the antibodies Ab-A and Ab-B.

The above results demonstrated that the humanized LAG-3 mouse model (B-hLAG-3) can be used as an in vivo animal model for investigating in vivo efficacy and toxicity of potential anti-cancer drugs. The humanized LAG-3 mouse model could also be used to screen for potential modulators of the LAG-3 signaling pathway, to evaluate the efficacy and toxicity of these modulators, and to design treatment regimens using these modulators. The humanized LAG-3 mouse model could additionally be used to evaluate and predict the efficacy and toxicity of anti-human LAG-3 antibodies, and the potential treatment results of drug candidates targeting human LAG-3.

Example 8. Preparing Mice with Double Humanized or Multiple Humanized Genes

Mice containing the humanized LAG-3 gene (such as the B-hLAG-3 animal model prepared using the methods described in previous sections) can also be used to prepare an animal model with double-humanized or multi-humanized genes. For example, in Example 4, the fertilized eggs used in the microinjection and embryo transfer process can be selected from the fertilized eggs of other genetically modified mice or the fertilized eggs of B-hLAG-3 mice, so as to obtain double- or multiple-gene modified mouse models.

In addition, the B-hLAG-3 animal model homozygote or heterozygote can be mated with other genetically modified homozygous or heterozygous animal models, and the progeny is then screened; according to the Mendelian law, there is a chance to obtain the double-gene or multiple-gene modified heterozygous animal models, and then the obtained heterozygous can be mated with each other to finally obtain the double-gene or multiple-gene modified homozygotes.

In the case of the generating double humanized LAG-3/PD-1 mice, since the mouse LAG-3 gene and the mouse PD-1 gene are located on different chromosomes (chromosome 6 and chromosome 2 respectively), the double humanized LAG-3/PD-1 mice were obtained by mating B-hLAG-3 mice with humanized PD-1 mice. The progeny mice were screened and further mated to obtain double humanized LAG-3/PD-1 mice.

PCR analysis was performed on the mouse tail genomic DNA of double humanized LAG-3/PD-1 mice using four pairs of primers. The specific sequences and product lengths are shown in Table 8. The reaction system and reaction conditions are shown in Table 9 and Table 10.

Figure 13A:
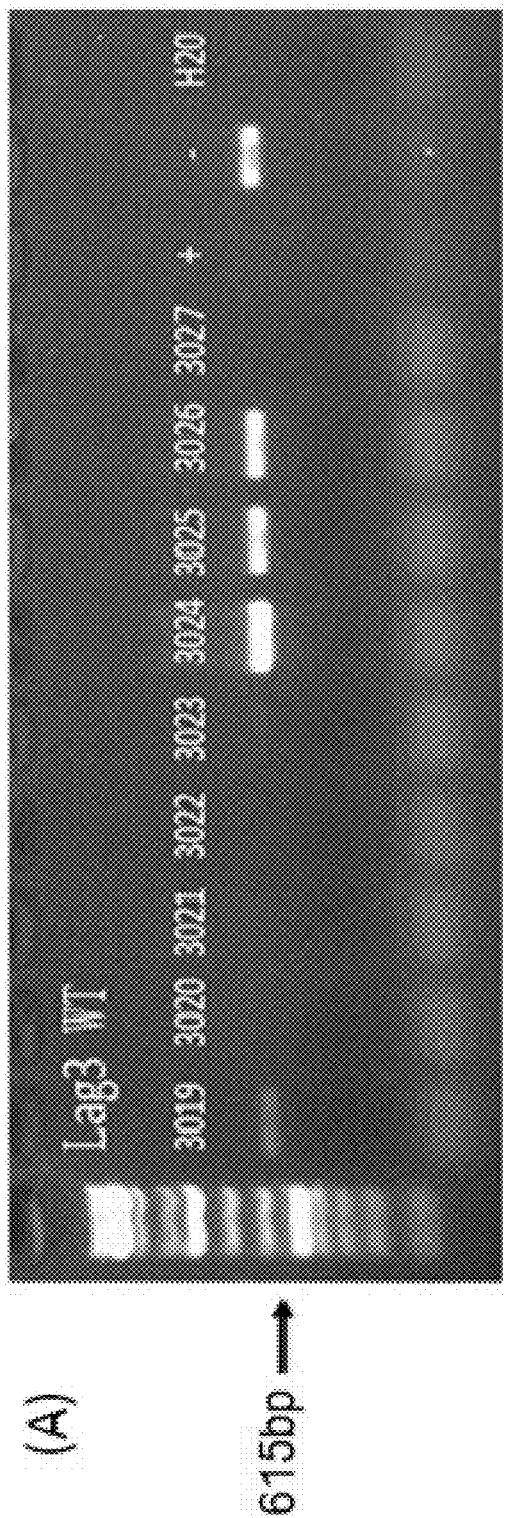
FIGS. 13A-13D show PCR detection results.
Figure 13B:
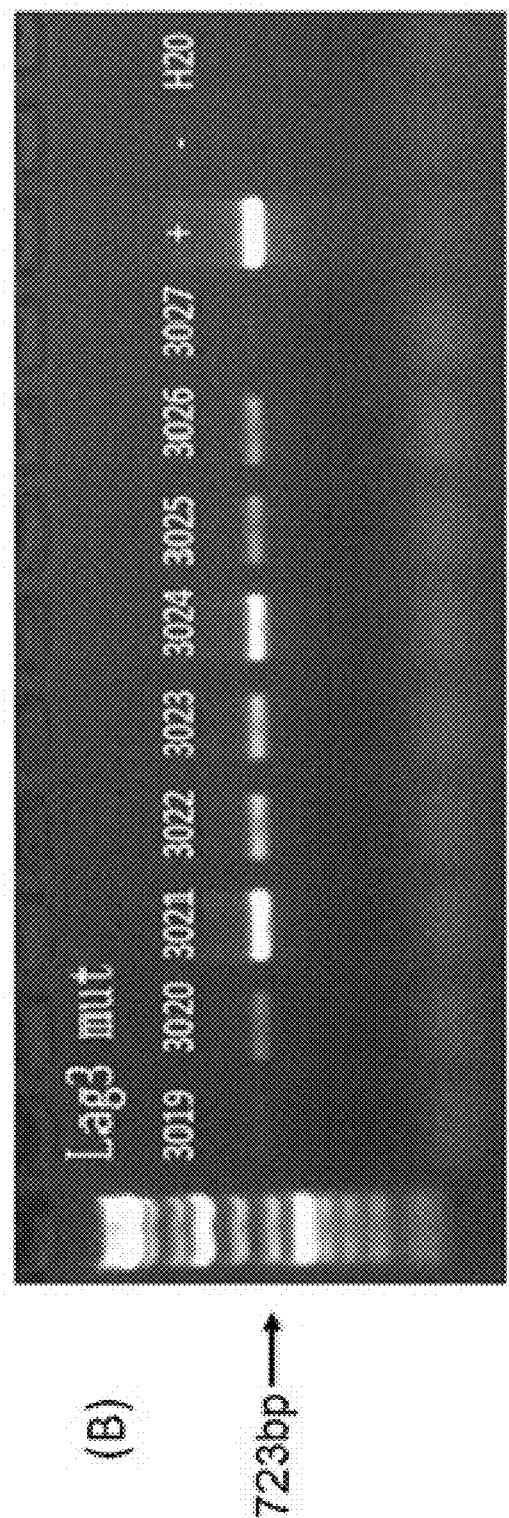
Figures 13C, 13D:
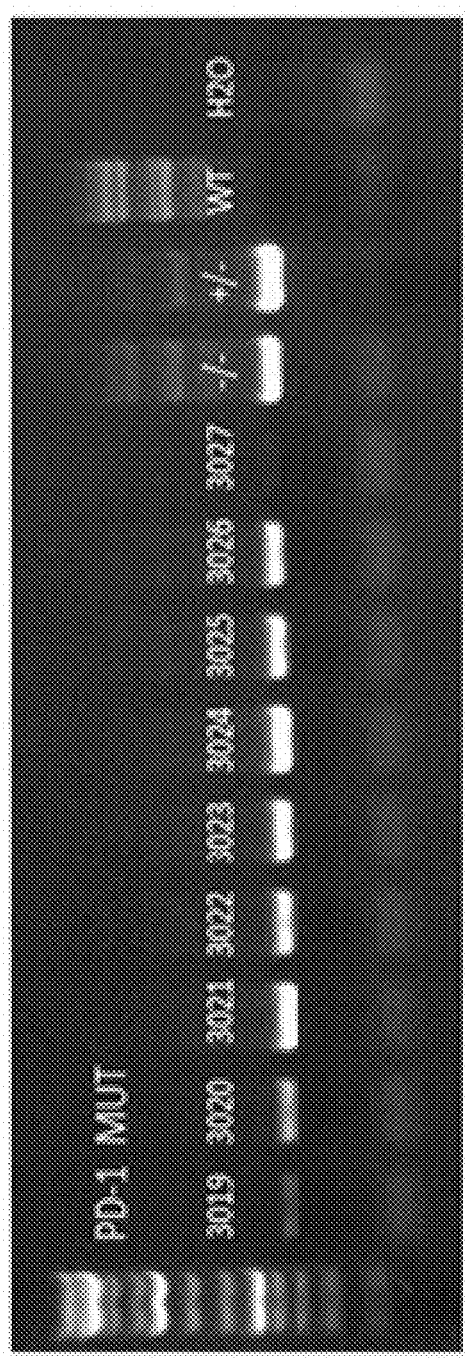

The results for a number of double humanized LAG-3/PD-1 mice are shown in FIGS. 13A-13D, wherein FIGS. 13A and 13B show that the mice numbered 3020-3023 were homozygous for humanized LAG-3, FIGS. 13C and 13D show that the mice numbered 3019-3027 were homozygous for humanized PD-1. The combined results show that the four mice numbered 3020-3023 were homozygous for both humanized LAG-3 and humanized PD-1.

TABLE 8

Primer sequences

| Primer | Sequence | Product length |
|---|---|---|
| LAG-3 WT | F: 5'-gctttgggaagctccaggtaag-3' (SEQ ID NO: 49)<br>R: 5'-gcttggacagggtttttatccattag-3' (SEQ ID NO: 51) | WT: 615 bp |
| LAG-3 MUT | F: 5'-gctttgggaagctccaggtaag-3' (SEQ ID NO: 49)<br>R: 5'-ggcgtgagggtcgctgattg-3' (SEQ ID NO: 42) | Mut: 723 bp |
| PD-1 MUT | F: 5'-cttccacatgagcgtggtcagggcc-3' (SEQ ID NO: 52)<br>R: 5'-ccaagggactattttagatgggcag-3' (SEQ ID NO: 53) | Mut: 325 bp |
| PD-1 WT | F: 5'-gaagctacaagctcctaggtaggggg-3' (SEQ ID NO: 54)<br>R: 5'-acgggttggctcaaaccattaca-3' (SEQ ID NO: 55) | WT: 345 bp |

TABLE 9

PCT reaction

| | |
|---|---|
| 2 × Master Mix | 10 μL |
| Upstream primer (10 μM) | 0.5 μL |
| Downstream primer (10 μM) | 0.5 μL |
| Mouse tail genomic DNA | 200 ng |
| KOD-Plus-(1 U/μL) | 0.6 μL |
| ddH$_2$O | Add to 20 μL |

TABLE 10

PCR amplification reaction condition

| Temperature | Time | Cycles |
|---|---|---|
| 95° C. | 5 min | 1 |
| 95° C. | 30 sec | 30 |
| 62° C. | 30 sec | |
| 72° C. | 30 sec | |
| 72° C. | 10 min | 1 |
| 4° C. | 10 min | 1 |

The double humanized LAG-3/PD-1 mice were further analyzed for protein expression using flow cytometry. One homozygous double humanized LAG-3/PD-1 mice (6-7 weeks), and two wildtype C57BL/6 mice were selected for the analysis. 7.5 μg of anti-mouse CD3 antibody was injected intraperitoneally to the mice. The spleens were collected 24 hours after the injection, and the spleen samples were grinded. The ground samples were then passed through 70 μm cell mesh. The filtered cell suspensions were centrifuged and the supernatants were discarded. Erythrocyte lysis solution was added to the sample, which was lysed for 5 min and neutralized with PBS solution. The solution was centrifuged again and the supernatants were discarded. The cells were washed once with PBS.

Figures 14A, 14B, 14C, 14D, 14E, 14F:
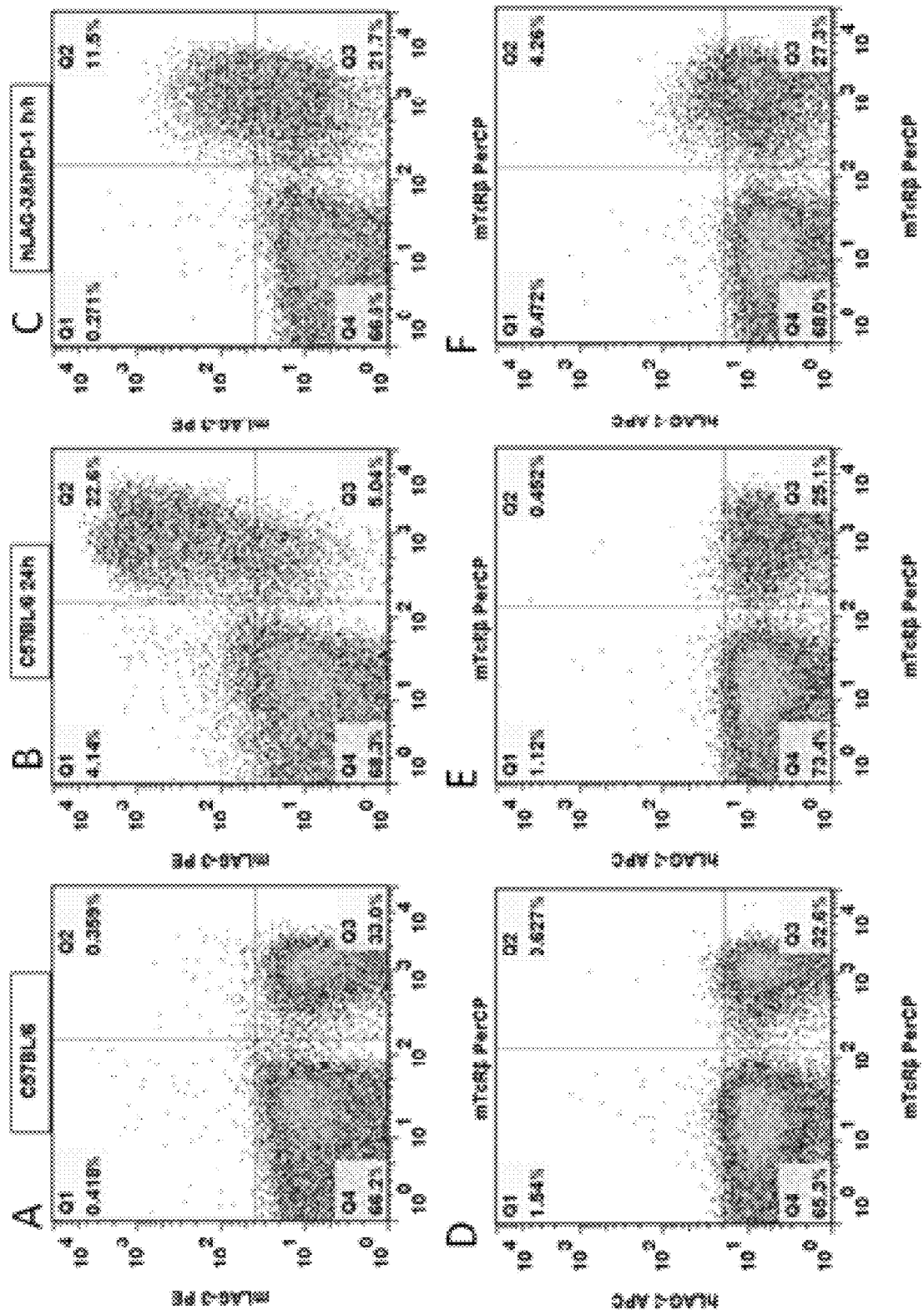
FIGS. 14A-14F are results of flow cytometry analysis for C57BL/6 mice and double humanized LAG-3/PD-1 homozygous mice. Anti-mouse CD3 antibody was used to stimulate T cell activation in the spleens of the mice. The cells were then stained with either (1) mouse LAG-3 antibody (mLAG-3 PE) and anti-mTCRβ antibody (mTcRβ PerCP) (FIGS. 14A, 14B, 14C), or (2) human LAG-3 antibody (hLAG-3 APC) and anti-mTCRβ antibody (mTcRβ PerCP) (FIGS. 14D, 14E, 14F). The results showed that the cells expressing humanized LAG-3 proteins were detected in the spleens of double humanized LAG-3/PD-1 homozygous mice, while no cell expressing humanized LAG-3 protein was detected in the spleens of C57BL/6 control mice.
Figures 15A, 15B, 15C, 15D, 15E, 15F:
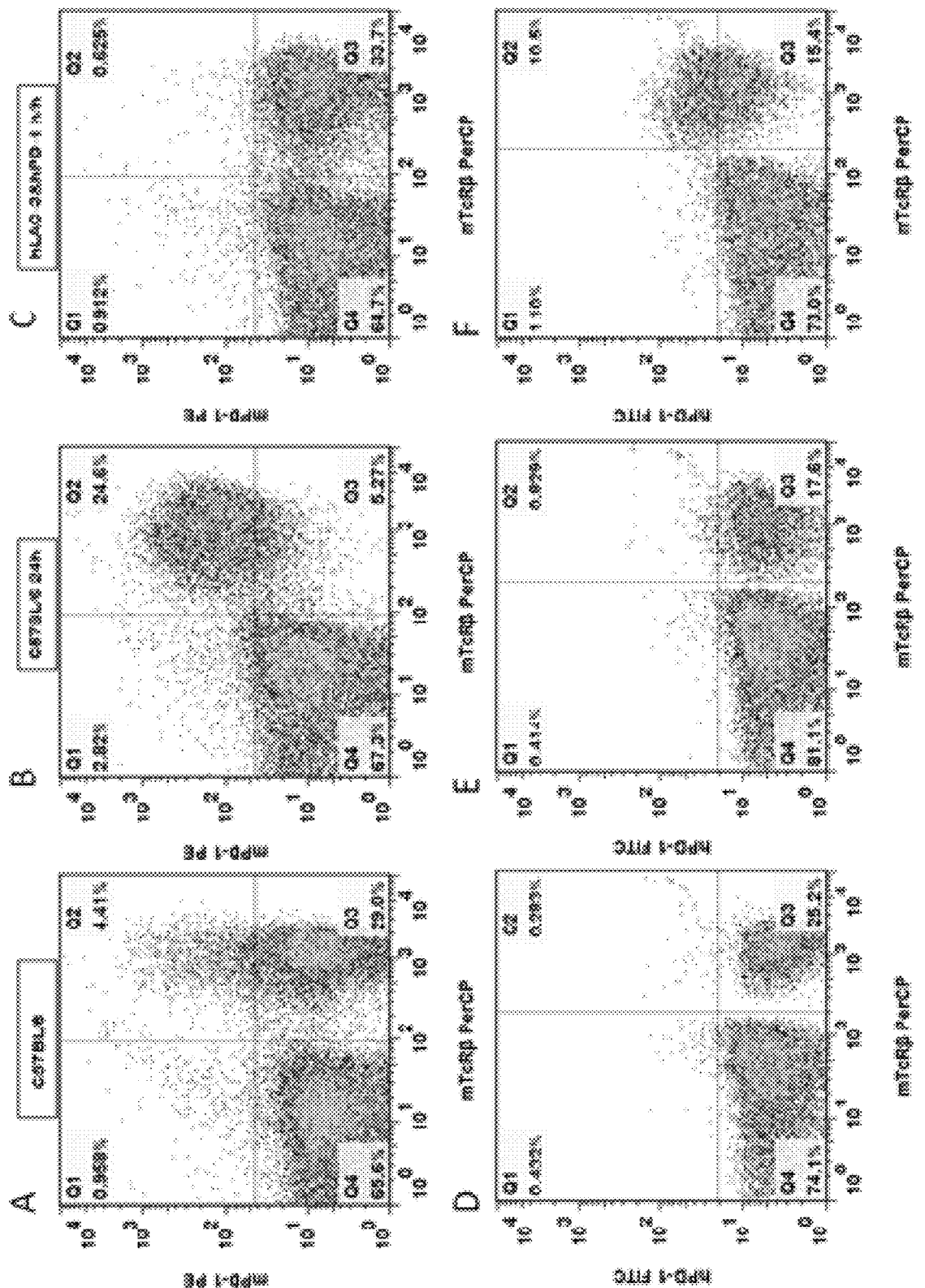
FIGS. 15A-15F are results of flow cytometry analysis for C57BL/6 mice and double humanized LAG-3/PD-1 homozygous mice. Anti-mouse CD3 antibody was used to stimulate T cell activation in the spleens of the mice. The cells were then stained with either mouse PD-1 antibody (mPD-1 PE) and anti-mTCRβ antibody (mTcRβ PerCP) (FIGS. 15A, 15B, 15C), or human PD-1 antibody (hPD-1 FITC) and anti-mTCRβ antibody (mTcRβ PerCP) (FIGS. 15D, 15E, 15F). The results showed that the cells expressing humanized PD-1 proteins were detected in the spleens of double humanized LAG-3/PD-1 homozygous mice, while no cell expressing humanized PD-1 protein was detected in the spleens of C57BL/6 control mice.

The cells were then stained with either (1) an anti-mouse LAG-3 antibody (mLAG3 PE) and an anti-mTcRβ antibody (mTcRβ PerCP) (FIGS. 14A-14C), or (2) an anti-human LAG-3 antibody (hLAG3 APC) and an anti-mTcRβ antibody (mTcRβ PerCP) (FIGS. 14D-14F). The cells were also stained with (1) an anti-mouse PD-1 antibody (mPD-1 PE) and an anti-mTcRβ antibody (mTcRβ PerCP) (FIGS. 15A-15C), or (2) an anti-human PD-1 antibody (hPD-1 FITC) and anti-mTcRβ antibody (mTcRβ PerCP) (FIGS. 15D-15E).

Results in FIGS. 14A-14F show that cells expressing humanized LAG-3 proteins were detected by anti-human LAG-3 antibodies in the spleens of homozygous double humanized LAG-3/PD-1 mice. No cells expressing humanized LAG-3 proteins were detected in the spleens of C57BL/6 mice with or without anti-CD3 antibody stimulation.

Results in FIGS. 15A-15F show that cells expressing humanized PD-1 proteins were detected by anti-human PD-1 antibodies in the spleens of homozygous double humanized LAG-3/PD-1 mice. No cells expressing humanized PD-1 proteins were to detected in the spleens of C57BL/6 mice either stimulated with or without anti-CD3 antibody stimulation.

Experiments were also performed to generate double humanized LAG-3/CTLA-4 mice. Since the mouse LAG-3 gene and CTLA-4 gene are located on different chromosomes (chromosome 6 and chromosome 1 respectively), the double humanized LAG-3/CTLA-4 mice were obtained by mating B-hLAG-3 mice with humanized CTLA-4 mice (e.g. B-hCTLA-4, mice with humanized CTLA-4 gene). The progeny mice were screened and further mated to eventually obtain double humanized LAG-3/CTLA-4 mice.

Figures 16A, 16B, 16C, 16D:
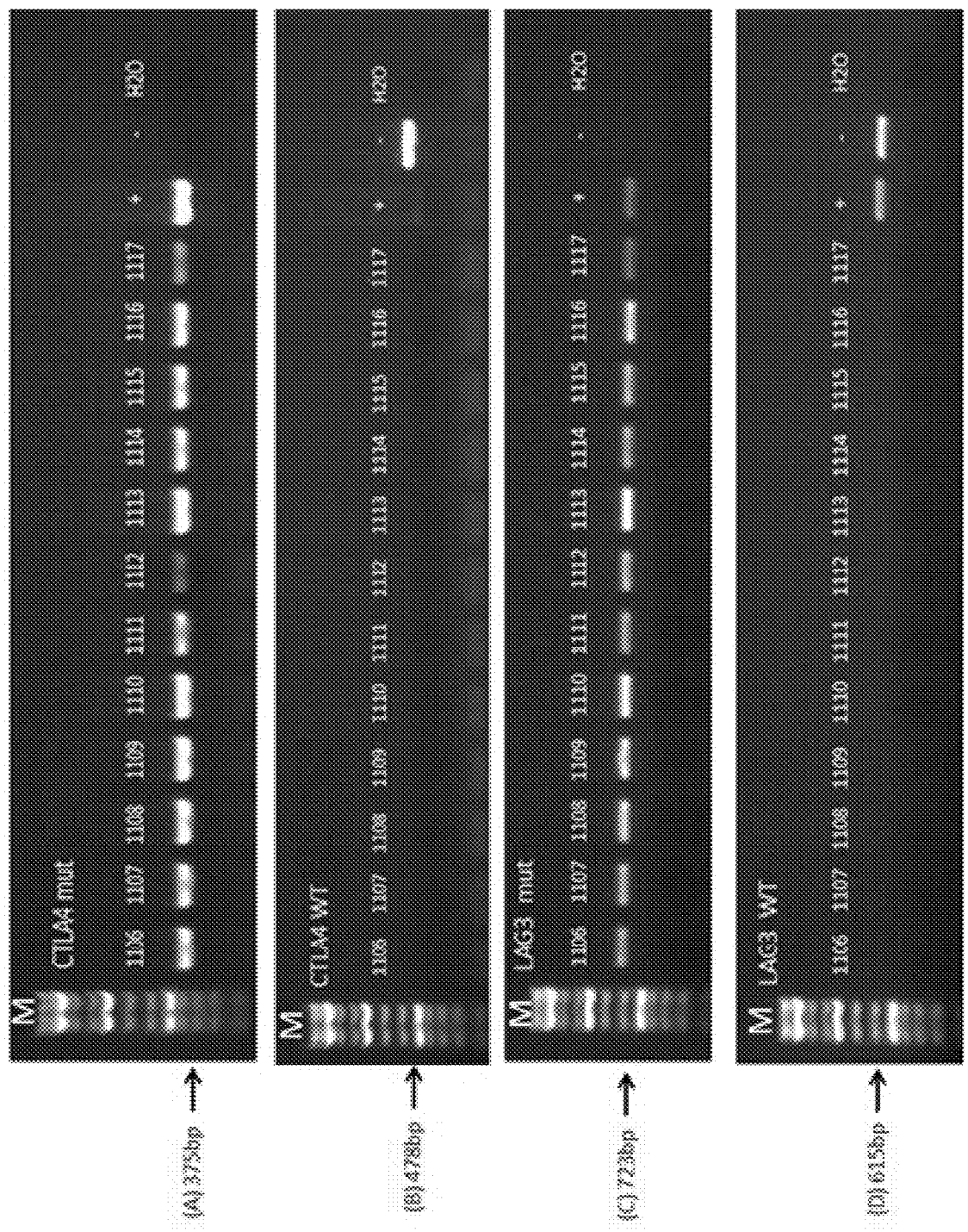
FIGS. 16A-16D are PCR results identifying double humanized LAG-3/CTLA-4 homozygous mice.

PCR analysis was performed on the mouse tail genomic DNA of double humanized LAG-3/CTLA-4 mice using four pairs of primers. The specific sequences and product lengths are shown in Table 11. The reaction system and reaction conditions are shown in Table 9 and Table 10. The results for a number of double humanized LAG-3/CTLA-4 mice are shown in FIGS. 16A-16D, wherein FIGS. 16A and 16B show that the mice numbered 1106-1117 were homozygous for humanized CTLA-4, FIGS. 16C and 16D show that the mice numbered 1106-1117 were homozygous for humanized LAG-3. These results show that the twelve mice numbered 1106-1117 were all homozygous for both humanized LAG-3 and humanized CTLA-4.

TABLE 11

Primer sequences

| Primer | Sequence | Product length |
|---|---|---|
| LAG-3 WT | F: SEQ ID NO: 49<br>R: SEQ ID NO: 51 | WT:<br>615 bp |
| LAG-3 MUT | F: SEQ ID NO: 49<br>R: SEQ ID NO: 42 | Mut:<br>723 bp |
| PD-1 MUT | F: 5'-acagctgaaagatgggaagtgg agt-3' (SEQ ID NO: 56)<br>R: 5'-tcaactcattcccatcatgt aggttgc-3' (SEQ ID NO: 57) | Mut:<br>375 bp |
| PD-1 WT | F: 5'-ccatcacacaacactgatgagg tcc-3' (SEQ ID NO: 58)<br>R: 5'-cacatcccaaatgcgtttcat tgc-3' (SEQ ID NO: 59) | WT:<br>478 bp |

Example 9. Pharmacological Validation of Double Humanized LAG-3/PD-1 Animal Model Combinations of more than one monoclonal antibody were widely used in tumor treatments. In this example, Keytruda (pembrolizumab) was combined with antibody Ab-C to demonstrate that double humanized LAG-3/PD-1 mice can be used to evaluate the efficacy of combination therapy.

Homozygous double humanized LAG-3/PD-1 mice (4-8 weeks) were subcutaneously injected with mouse colon cancer cell MC38. When the tumor volume grew to about 100 mm$^3$, the mice were randomly divided to a control group and two treatment groups. The treatment groups were randomly selected for treatment with Keytruda (0.1 mg/kg) or with both of Keytruda (0.1 mg/kg) and Ab-C (10 mg/kg). The control group was injected with an equal volume of blank solvent. The tumor volume and the body weight were measured twice a week. Euthanasia was performed when the tumor volume of the mouse reached 3000 mm$^3$. Table 12 provides more details on the method of administration.

Figure 17:
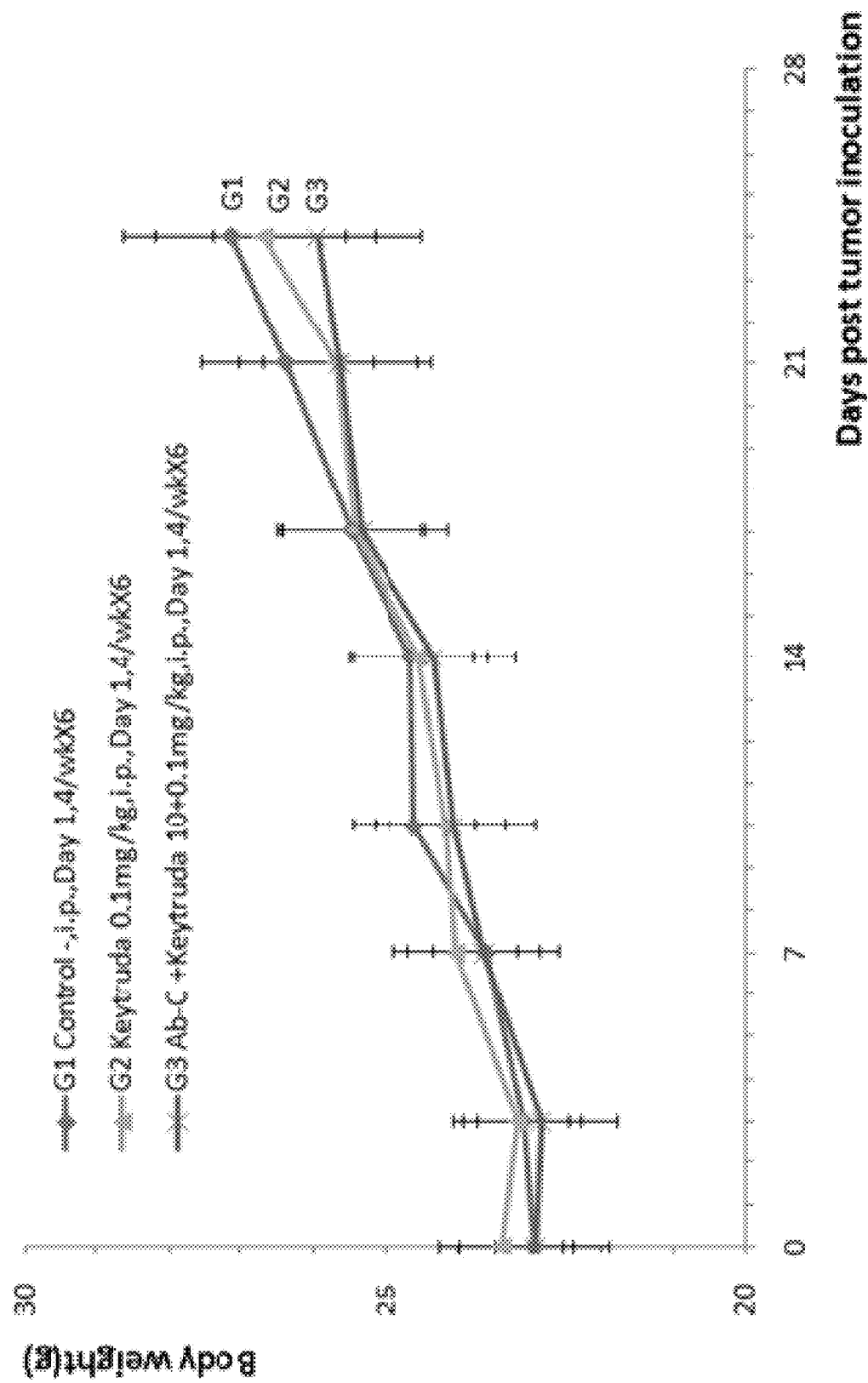
FIG. 17. Mouse colon cancer cells MC38 were injected into double humanized homozygous LAG-3/PD-1 mice. Antitumor efficacy studies were performed with Keytruda (anti-human PD-1 antibody), and Keytruda in combination with anti-human LAG-3 antibody (Ab-C). There was no significant difference in the average weight between the G1 control group and the G2-G3 treatment groups.
Figure 18:
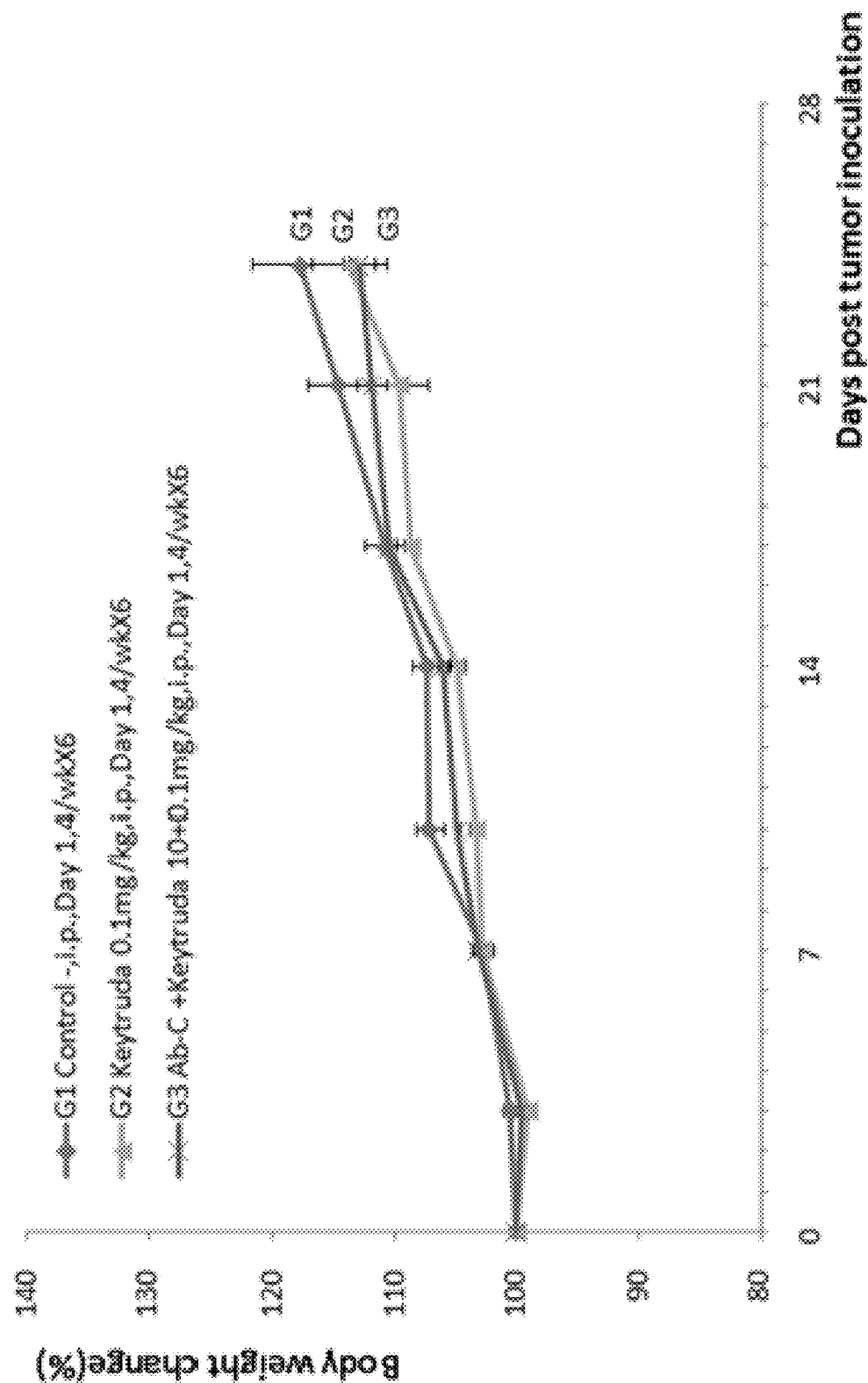
FIG. 18. Mouse colon cancer cells MC38 were injected into double humanized homozygous LAG-3/PD-1 mice. Antitumor efficacy studies were performed with Keytruda, and Keytruda in combination with anti-human LAG-3 antibody (Ab-C). There was no significant difference in the percentage of body weight change among the different groups.
Figure 19:
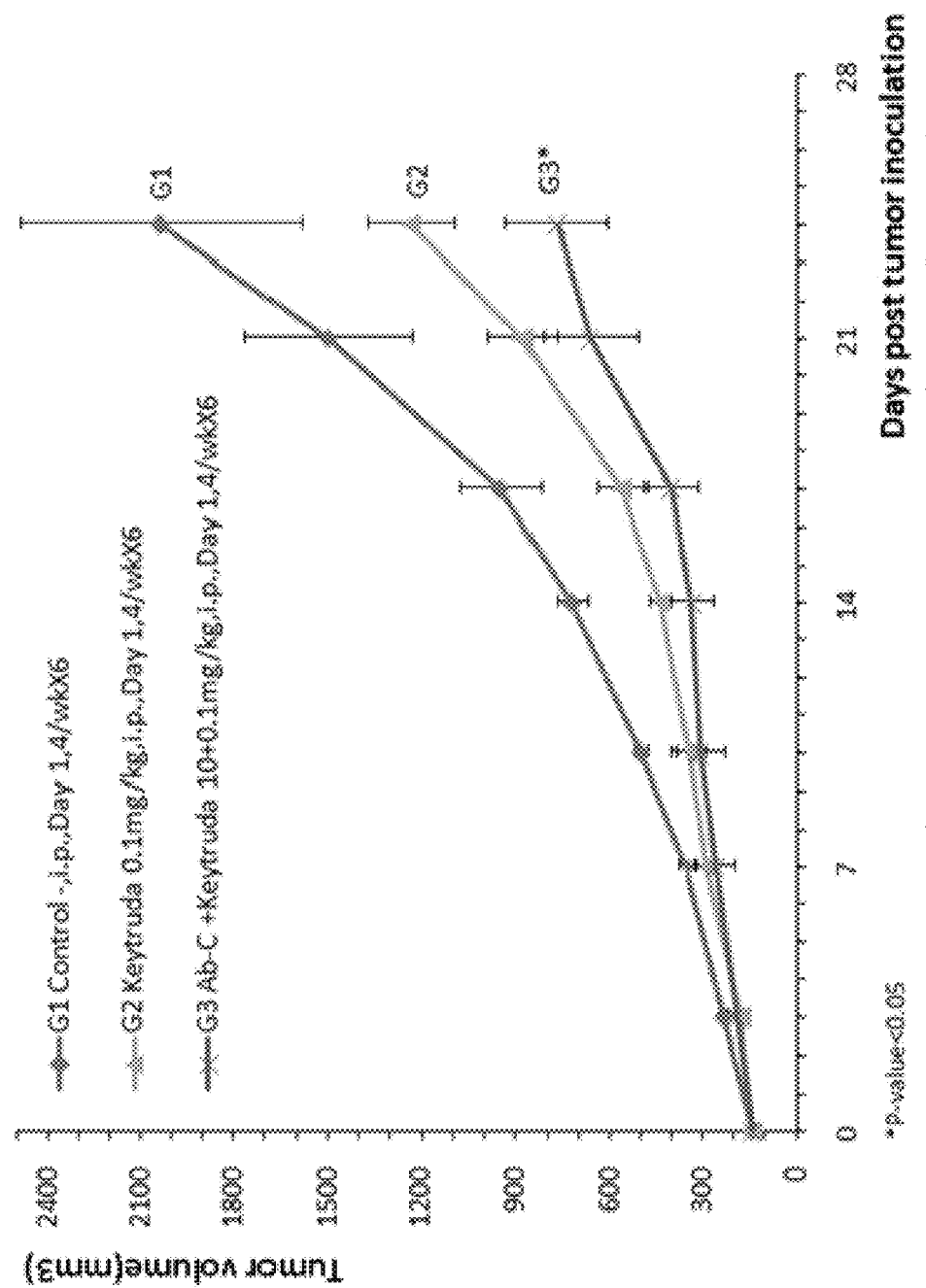
FIG. 19. Mouse colon cancer cells MC38 were injected into double humanized homozygous LAG-3/PD-1 mice. Antitumor efficacy studies were performed with Keytruda, and Keytruda in combination with anti-human LAG-3 antibody (Ab-C). The average volumes of tumors in the G2-G3 treatment groups were significantly smaller than the G1 control group. Furthermore, the tumor size in mice treated with the combination of Keytruda and Ab-C is significantly smaller than the tumor size in mice treated with Keytruda alone.

FIG. 17 and FIG. 18 show that the mice in the control group and the treatment groups had no significant difference in body weight or body weight percentage change. FIG. 19 shows that the tumors in control group mice (G1) kept growing during the experimental period, while tumor sizes in the treatment group mice (G2 and G3) decreased, indicating that tumor growth were inhibited.

Table 13 shows the tumor volumes at the day of grouping (Day 0), 17 days after grouping (Day 17), and at the end of the experiment (day 24); the survival rate of the mice; the number of tumor-free mice (non-existence of tumor); the Tumor Growth Inhibition value ($TGI_{TV}$); and the statistical differences (P value) in mouse body weight and tumor volume between the treatment and control groups.

At the end of the experiment, all mice survived. The average tumor size of the control group (G1) was 2038±423 mm$^3$; the average tumor size in the treatment group treated with Keytruda alone (G2) was 1234±142 mm$^3$; and the average tumor size in the treatment group treated with both Keytruda and Ab-C (G3) was 771±164 mm$^3$. Thus, the combination treatment group (G3) had significantly smaller tumor size as compared to G2. The $TGI_{TV}$ values were 42.3% and 66.8% for group G2 and G3 respectively, indicating that the efficacy of using a combination of these two antibodies is better than that of using only one antibody. The efficacy of the treatment in group G3 was also significant (P=0.030; $TGI_{TV}$ value >60%). Accordingly, using a combination of an anti-human PD-1 antibody (e.g., Keytruda), and an anti-human LAG-3 antibody effectively inhibited tumor growth.

TABLE 12

| Groups | Treatment or Control | Administration |
|---|---|---|
| G1 | Blank solvent | Intraperitoneal injection; twice a week; six administrations in total. |
| G2 | Keytruda | 0.1 mg/kg; intraperitoneal injection; twice a week; six administrations in total. |
| G3 | Keytruda + Ab-C | Keytruda: 0.1 mg/kg; intraperitoneal injection; twice a week; six administrations in total.<br>Ab-C: 10 mg/kg; intraperitoneal injection; twice a week; six administrations in total. |

TABLE 13

| | | Tumor volume (mm³) | | | Non-existence | | P value | |
|---|---|---|---|---|---|---|---|---|
| | | Day 0 | Day 17 | Day 24 | Survival | of tumor | $TGI_{TV}$% | Body weight | Tumor Volume |
| Control | G1 | 140 ± 10 | 949 ± 128 | 2038 ± 423 | 5/5 | 0/5 | N/A | N/A | N/A |
| Treatment | G2 | 140 ± 8 | 561 ± 79 | 1234 ± 142 | 5/5 | 0/5 | 42.3 | 0.844 | 0.129 |
| | G3 | 140 ± 7 | 404 ± 86 | 771 ± 164 | 5/5 | 0/5 | 66.8 | 0.598 | 0.030 |

Example 10. Methods Based on Embryonic Stem Cell Technologies

The non-human mammals described herein can also be prepared through other gene editing systems and approaches, including but not limited to: gene homologous recombination techniques based on embryonic stem cells (ES), zinc finger nuclease (ZFN) techniques, transcriptional activator-like effector factor nuclease (TALEN) technique, homing endonuclease (megakable base ribozyme), or other techniques.

Figure 20:
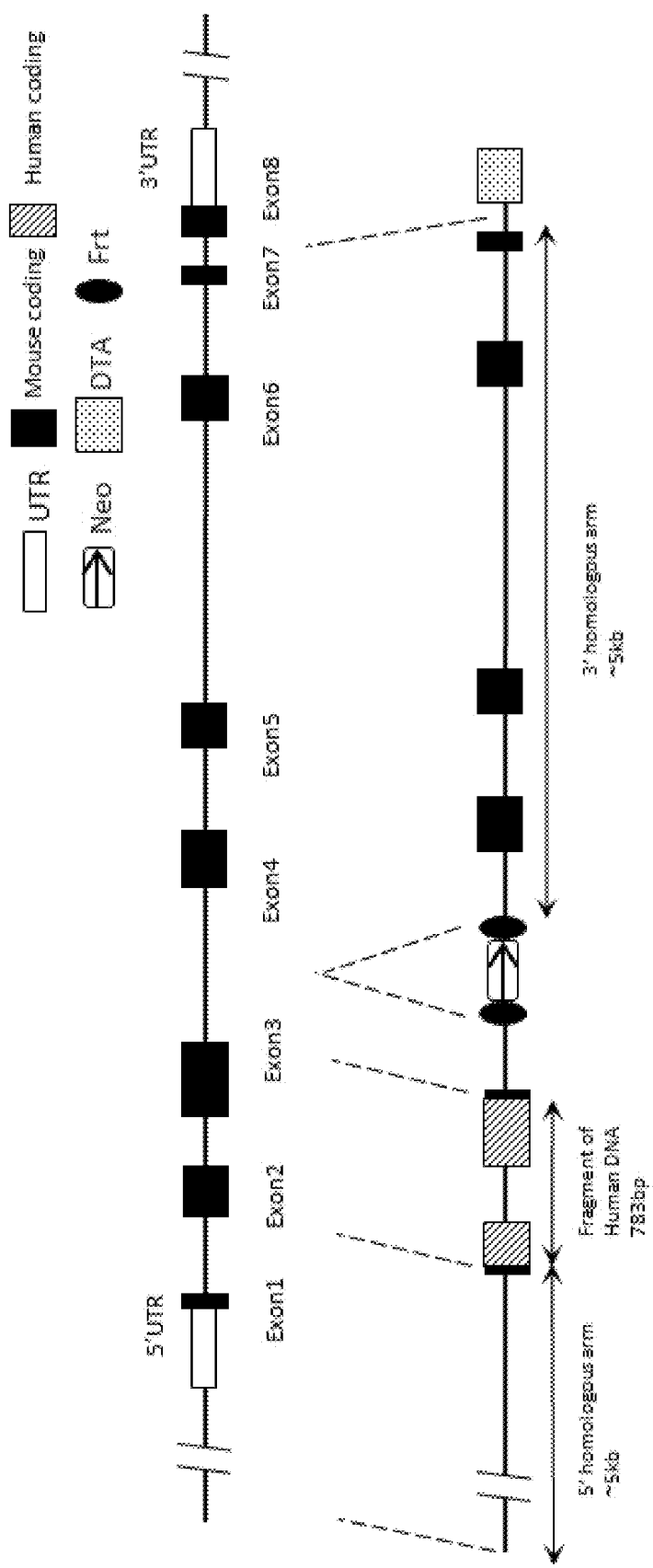
FIG. 20 is a schematic diagram of a targeting strategy for embryonic stem cells.

In this example, the conventional ES cell gene homologous recombination technique is used as an example to describe how to obtain LAG-3 gene humanized mice by other methods. Based on the humanized mouse LAG-3 gene map (FIG. 3B), a gene editing strategy and methods are shown in FIG. 20, which also shows the design of the recombinant vector. Since the objective is to replace exon 2 and exon 3 of the mouse LAG-3 gene in whole or in part with the corresponding human LAG-3 gene fragment, a recombinant vector that contains a 5' homologous arm (5068 bp), a 3' homologous arm (5180 bp) and a humanized gene fragment (783 bp) is also designed. The vector can also contain a resistance gene for positive clone screening, such as neomycin phosphotransferase coding sequence Neo. On both sides of the resistance gene, two site-specific recombination systems in the same orientation, such as Frt or LoxP, can be added. Furthermore, a coding gene with a negative screening marker, such as the diphtheria toxin A subunit coding gene (DTA), can be constructed downstream of the recombinant vector 3' homologous arm. Vector construction can be carried out using methods known in the art, such as enzyme digestion and so on. The recombinant vector with correct sequence can be next transfected into mouse embryonic stem cells, such as C57BL/6 mouse embryonic stem cells, and then the recombinant vector can be screened by positive clone screening gene. The cells transfected with the recombinant vector are next screened by using the positive clone marker gene, and Southern Blot technique can be used for DNA recombination identification. For the selected correct positive clones, the positive clonal cells (black mice) are injected into the isolated blastocysts (white mice) by microinjection according to the method described in the book A. Nagy, et al., "Manipulating the Mouse Embryo: A Laboratory Manual (Third Edition)," Cold Spring Harbor Laboratory Press, 2003. The resulting chimeric blastocysts formed following the injection are transferred to the culture medium for a short time culture and then transplanted into the fallopian tubes of the recipient mice (white mice) to produce F0 generation chimeric mice (black and white). The F0 generation chimeric mice with correct gene recombination are then selected by extracting the mouse tail genome and detecting by PCR for subsequent breeding and identification. The F1 generation mice are obtained by mating the F0 generation chimeric mice with wildtype mice. Stable gene recombination positive F1 heterozygous mice are selected by extracting rat tail genome and PCR detection. Next, the F1 heterozygous mice are mated to each other to obtain genetically recombinant positive F2 generation homozygous mice. In addition, the F1 heterozygous mice can also be mated with Flp or Cre mice to remove the positive clone screening marker gene (neo, etc.), and then the LAG-3 gene humanized homozygous mice can be obtained by mating these mice with each other. The methods of genotyping and phenotypic detection of the obtained F1 heterozygous mice or F2 homozygous mice are similar to those used in Example 5 described above.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A genetically-modified, non-human animal whose genome comprises at least one chromosome comprising a sequence encoding a chimeric Lymphocyte Activation Gene 3 (LAG-3), wherein the chimeric LAG-3 comprises an amino acid sequence that is identical to SEQ ID NO: 31.

2. The animal of claim 1, wherein the sequence encoding the chimeric LAG-3 is operably linked to an endogenous regulatory element at the endogenous LAG-3 gene locus in the at least one chromosome.

3. The animal of claim 1, wherein the chimeric LAG-3 consists of an amino acid sequence that is identical to SEQ ID NO: 31.

4. The animal of claim 1, wherein the animal is a rodent.

5. The animal of claim 1, wherein the animal is a mouse.

6. The animal of claim 1, wherein the animal does not express endogenous LAG-3.

7. The animal of claim 1, wherein the animal has one or more cells expressing the chimeric LAG-3.

8. The animal of claim 1, wherein the animal further comprises a sequence encoding an additional human or chimeric protein.

9. The animal of claim 8, wherein the additional human or chimeric protein is programmed cell death protein 1 (PD-1), cytotoxic T-lymphocyte-associated protein 4 (CTLA-4), T-cell immunoglobulin and mucin-domain containing-3 (TIM-3), B And T Lymphocyte Associated (BTLA), Programmed Cell Death 1 Ligand 1 (PD-L1), TNF Receptor Superfamily Member 9 (4-1BB), CD27, CD28, CD47, T-Cell Immunoreceptor With Ig And ITIM Domains (TIGIT), CD27, Glucocorticoid-Induced TNFR-Related Protein (GITR), or TNF Receptor Superfamily Member 4 (OX40).

10. A method of determining effectiveness of an anti-LAG-3 antibody for treating cancer, comprising:
   administering the anti-LAG-3 antibody to the animal of claim 1, wherein the animal has a tumor; and
   determining inhibitory effects of the anti-LAG-3 antibody to the tumor.

11. The method of claim 10, wherein the tumor comprises one or more human cancer cells that are injected into the animal.

12. The animal of claim 1, wherein the animal is modified and the modification is performed by CRISPR associated protein 9 (Cas9) with sgRNAs that target SEQ ID NO: 5 and SEQ ID NO: 12.

* * * * *

SEQUENCE LISTING

<160> NUMBER OF SEQ ID NOS: 59

<210> SEQ ID NO 1
<211> LENGTH: 23
<212> TYPE: DNA
<213> ORGANISM: Artificial Sequence
<220> FEATURE:
<223> OTHER INFORMATION: sgRNA targeting sequence

<400> SEQUENCE: 1
gttccactag ttgtgtcttc agg                                              23

<210> SEQ ID NO 2

```
<211> LENGTH: 23
<212> TYPE: DNA
<213> ORGANISM: Artificial Sequence
<220> FEATURE:
<223> OTHER INFORMATION: sgRNA targeting sequence

<400> SEQUENCE: 2
ggccctgaag acacaactag tgg                                               23

<210> SEQ ID NO 3
<211> LENGTH: 23
<212> TYPE: DNA
<213> ORGANISM: Artificial Sequence
<220> FEATURE:
<223> OTHER INFORMATION: sgRNA targeting sequence

<400> SEQUENCE: 3
accacgggga gctctttccc agg                                               23

<210> SEQ ID NO 4
<211> LENGTH: 23
<212> TYPE: DNA
<213> ORGANISM: Artificial Sequence
<220> FEATURE:
<223> OTHER INFORMATION: sgRNA targeting sequence

<400> SEQUENCE: 4
ctagttgtgt cttcagggcc tgg                                               23

<210> SEQ ID NO 5
<211> LENGTH: 23
<212> TYPE: DNA
<213> ORGANISM: Artificial Sequence
<220> FEATURE:
<223> OTHER INFORMATION: sgRNA targeting sequence

<400> SEQUENCE: 5
gcctgggaaa gagctccccg tgg                                               23

<210> SEQ ID NO 6
<211> LENGTH: 23
<212> TYPE: DNA
<213> ORGANISM: Artificial Sequence
<220> FEATURE:
<223> OTHER INFORMATION: sgRNA targeting sequence

<400> SEQUENCE: 6
cctcctgggc ccacaccacg ggg                                               23

<210> SEQ ID NO 7
<211> LENGTH: 23
<212> TYPE: DNA
<213> ORGANISM: Artificial Sequence
<220> FEATURE:
<223> OTHER INFORMATION: sgRNA targeting sequence

<400> SEQUENCE: 7
ggaaagagct ccccgtggtg tgg                                               23

<210> SEQ ID NO 8
<211> LENGTH: 23
<212> TYPE: DNA
<213> ORGANISM: Artificial Sequence
<220> FEATURE:
<223> OTHER INFORMATION: sgRNA targeting sequence

<400> SEQUENCE: 8
```
tcgaggcctg gccgacgcgc agg                                          23

<210> SEQ ID NO 9
<211> LENGTH: 23
<212> TYPE: DNA
<213> ORGANISM: Artificial Sequence
<220> FEATURE:
<223> OTHER INFORMATION: sgRNA targeting sequence

<400> SEQUENCE: 9
tctccgcctg cgcgtcggcc agg                                          23

<210> SEQ ID NO 10
<211> LENGTH: 23
<212> TYPE: DNA
<213> ORGANISM: Artificial Sequence
<220> FEATURE:
<223> OTHER INFORMATION: sgRNA targeting sequence

<400> SEQUENCE: 10
aggcctggcc gacgcgcagg cgg                                          23

<210> SEQ ID NO 11
<211> LENGTH: 23
<212> TYPE: DNA
<213> ORGANISM: Artificial Sequence
<220> FEATURE:
<223> OTHER INFORMATION: sgRNA targeting sequence

<400> SEQUENCE: 11
tgcagtctcc gcctgcgcgt cgg                                          23

<210> SEQ ID NO 12
<211> LENGTH: 23
<212> TYPE: DNA
<213> ORGANISM: Artificial Sequence
<220> FEATURE:
<223> OTHER INFORMATION: sgRNA targeting sequence

<400> SEQUENCE: 12
aggagagggc gcggttcggg agg                                          23

<210> SEQ ID NO 13
<211> LENGTH: 23
<212> TYPE: DNA
<213> ORGANISM: Artificial Sequence
<220> FEATURE:
<223> OTHER INFORMATION: sgRNA targeting sequence

<400> SEQUENCE: 13
gcggttcggg aggcgcacgg tgg                                          23

<210> SEQ ID NO 14
<211> LENGTH: 23
<212> TYPE: DNA
<213> ORGANISM: Artificial Sequence
<220> FEATURE:
<223> OTHER INFORMATION: sgRNA targeting sequence

<400> SEQUENCE: 14
tgcaggagag ggcgcggttc ggg                                          23

<210> SEQ ID NO 15
<211> LENGTH: 19
<212> TYPE: DNA

```
<213> ORGANISM: Artificial Sequence
<220> FEATURE:
<223> OTHER INFORMATION: sgRNA sequence

<400> SEQUENCE: 15
cctgggaaag agctccccg                                                    19

<210> SEQ ID NO 16
<211> LENGTH: 23
<212> TYPE: DNA
<213> ORGANISM: Artificial Sequence
<220> FEATURE:
<223> OTHER INFORMATION: sgRNA sequence

<400> SEQUENCE: 16
taggcctggg aaagagctcc ccg                                               23

<210> SEQ ID NO 17
<211> LENGTH: 19
<212> TYPE: DNA
<213> ORGANISM: Artificial Sequence
<220> FEATURE:
<223> OTHER INFORMATION: sgRNA sequence

<400> SEQUENCE: 17
cggggagctc tttcccagg                                                    19

<210> SEQ ID NO 18
<211> LENGTH: 23
<212> TYPE: DNA
<213> ORGANISM: Artificial Sequence
<220> FEATURE:
<223> OTHER INFORMATION: sgRNA sequence

<400> SEQUENCE: 18
aaaccgggga gctctttccc agg                                               23

<210> SEQ ID NO 19
<211> LENGTH: 17
<212> TYPE: DNA
<213> ORGANISM: Artificial Sequence
<220> FEATURE:
<223> OTHER INFORMATION: sgRNA sequence

<400> SEQUENCE: 19
agagggcgcg gttcggg                                                      17

<210> SEQ ID NO 20
<211> LENGTH: 21
<212> TYPE: DNA
<213> ORGANISM: Artificial Sequence
<220> FEATURE:
<223> OTHER INFORMATION: sgRNA sequence

<400> SEQUENCE: 20
taggagaggg cgcggttcgg g                                                 21

<210> SEQ ID NO 21
<211> LENGTH: 17
<212> TYPE: DNA
<213> ORGANISM: Artificial Sequence
<220> FEATURE:
<223> OTHER INFORMATION: sgRNA sequence

<400> SEQUENCE: 21
cccgaaccgc gcccct                                                       17
```

<210> SEQ ID NO 22
<211> LENGTH: 21
<212> TYPE: DNA
<213> ORGANISM: Artificial Sequence
<220> FEATURE:
<223> OTHER INFORMATION: sgRNA sequence

<400> SEQUENCE: 22 aaacccgaa ccgcgccctc t                                              21

<210> SEQ ID NO 23
<211> LENGTH: 132
<212> TYPE: DNA
<213> ORGANISM: Artificial Sequence
<220> FEATURE:
<223> OTHER INFORMATION: synthesized sequence

<400> SEQUENCE: 23
gaattctaat acgactcact ataggggtc ttcgagaaga cctgttttag agctagaaat     60
agcaagttaa aataaggcta gtccgttatc aacttgaaaa agtggcaccg agtcggtgct  120
tttaaaggat cc                                                      132

<210> SEQ ID NO 24
<211> LENGTH: 2020
<212> TYPE: DNA
<213> ORGANISM: Mus musculus

<400> SEQUENCE: 24
gggcagtggg gaggagaagc agaaggactg ggtctggagg agcagctcaa gttctagcta    60
gctgcagtgg gtttgcctgc actctgctct gggtcccagc ccgggcctct gatcattatc   120
catcctgctg tctccagtcc ccactcctgg ggcgtcctct tcaccctaca ttctttccct   180
ccgcctcacc tcctccttgt agaacttctc tctctctctc tctctctctc tctctctctc   240
tctctctctc tctgtgtgtg tgtgtgtgtc tgtctgtctg tctgtctctc tctcctccca   300 ggacctttt ctaacctccc ttggagggct ggggaggccc gggccataga ggagatgagg    360
gaggacctgc tccttggctt tttgcttctg ggactgcttt gggaagctcc agttgtgtct   420
tcagggcctg ggaaagagct ccccgtggtg tgggcccagg agggagctcc cgtccatctt   480
ccctgcagcc tcaaatcccc caacctggat cctaactttc tacgaagagg aggggttatc   540
tggcaacatc aaccagacag tggccaaccc actcccatcc cggcccttga ccttcaccag   600
gggatgccct cgcctagaca acccgcaccc ggtcgctaca cggtgctgag cgtggctcca   660
ggaggcctgc gcagcgggag gcagcccctg catccccacg tgcagctgga ggagcgcggc   720
ctccagcgcg gggacttctc tctgtggttg cgcccagctc tgcgcaccga tgcgggcgag   780
taccacgcca ccgtgcgcct cccgaaccgc gccctctcct gcagtctccg cctgcgcgtc   840
ggccaggcct cgatgattgc tagtccctca ggagtcctca agctgtctga ttgggtcctt   900
ttgaactgct ccttcagccg tcctgaccgc ccagtctctg tgcactggtt ccagggccag   960
aaccgagtgc ctgtctacaa ctcaccgcgt cattttttag ctgaaacttt cctgttactg  1020
ccccaagtca gcccctgga ctctgggacc tgggctgtg tcctcaccta cagagatggc   1080
ttcaatgtct ccatcacgta caacctcaag gttctgggtc tggagcccgt agccctctg   1140 acagtgtacg ctgctgaagg ttctagggtg gagctgccct gtcatttgcc cccaggagtg  1200 gggaccccctt ctttgctcat tgccaagtgg actcctcctg gaggaggtcc tgagctcccc  1260

```
gtggctggaa agagtggcaa ttttacccct caccttgagg ctgtgggtct ggcacaggct   1320
gggacctaca cctgtagcat ccatctgcag ggacagcagc tcaatgccac tgtcacgttg   1380
gcggtcatca cagtgactcc caaatccttc gggttacctg gctcccgggg gaagctgttg   1440
tgtgaggtaa ccccggcatc tggaaaggaa agatttgtgt ggcgtcccct gaacaatctg   1500
tccaggagtt gcccgggccc tgtgctggag attcaggagg ccaggctcct tgctgagcga   1560
tggcagtgtc agctgtacga gggccagagg cttcttggag cgacagtgta cgccgcagag   1620
tctagctcag gcgcccacag tgctaggaga atctcaggtg accttaaagg aggccatctc   1680
gttctcgttc tcatccttgg tgccctctcc ctgttccttt tggtggccgg ggcctttggc   1740
tttcactggt ggagaaaaca gttgctactg agaagatttt ctgccttaga acatgggatt   1800
cagccatttc cggctcagag gaagatagag gagctggagc gagaactgga gacgagatg    1860 ggacaggagc cggagcccga gccggagcca gcagctgagc cagagcccag gcagctctga   1920
cctggagccg aggcagccag caggtctcag cagctccgcc cgcccgcccg cccgcccgaa   1980
taaactccct gtcagcagca tcaaaaaaaa aaaaaaaaa                          2020
```

<210> SEQ ID NO 25
<211> LENGTH: 521
<212> TYPE: PRT
<213> ORGANISM: Mus musculus

<400> SEQUENCE: 25

```
Met Arg Glu Asp Leu Leu Gly Phe Leu Leu Gly Leu Leu Trp
1               5                   10                  15

Glu Ala Pro Val Ser Ser Gly Pro Gly Lys Glu Leu Pro Val Val
                20                  25                  30

Trp Ala Gln Glu Gly Ala Pro Val His Leu Pro Cys Ser Leu Lys Ser
            35                  40                  45

Pro Asn Leu Asp Pro Asn Phe Leu Arg Arg Gly Gly Val Ile Trp Gln
        50                  55                  60

His Gln Pro Asp Ser Gly Gln Pro Thr Pro Ile Pro Ala Leu Asp Leu
65                  70                  75                  80

His Gln Gly Met Pro Ser Pro Arg Gln Pro Ala Pro Gly Arg Tyr Thr
                85                  90                  95

Val Leu Ser Val Ala Pro Gly Gly Leu Arg Ser Gly Arg Gln Pro Leu
            100                 105                 110

His Pro His Val Gln Leu Glu Glu Arg Gly Leu Gln Arg Gly Asp Phe
        115                 120                 125

Ser Leu Trp Leu Arg Pro Ala Leu Arg Thr Asp Ala Gly Glu Tyr His
    130                 135                 140

Ala Thr Val Arg Leu Pro Asn Arg Ala Leu Ser Cys Ser Leu Arg Leu
145                 150                 155                 160

Arg Val Gly Gln Ala Ser Met Ile Ala Ser Pro Ser Gly Val Leu Lys
                165                 170                 175

Leu Ser Asp Trp Val Leu Leu Asn Cys Ser Phe Ser Arg Pro Asp Arg
            180                 185                 190

Pro Val Ser Val His Trp Phe Gln Gly Gln Asn Arg Val Pro Val Tyr
        195                 200                 205

Asn Ser Pro Arg His Phe Leu Ala Glu Thr Phe Leu Leu Leu Pro Gln
    210                 215                 220

Val Ser Pro Leu Asp Ser Gly Thr Trp Gly Cys Val Leu Thr Tyr Arg
225                 230                 235                 240
```

Asp Gly Phe Asn Val Ser Ile Thr Tyr Asn Leu Lys Val Leu Gly Leu
                245                 250                 255

Glu Pro Val Ala Pro Leu Thr Val Tyr Ala Ala Glu Gly Ser Arg Val
            260                 265                 270

Glu Leu Pro Cys His Leu Pro Pro Gly Val Gly Thr Pro Ser Leu Leu
        275                 280                 285

Ile Ala Lys Trp Thr Pro Pro Gly Gly Gly Pro Glu Leu Pro Val Ala
    290                 295                 300

Gly Lys Ser Gly Asn Phe Thr Leu His Leu Glu Ala Val Gly Leu Ala
305                 310                 315                 320

Gln Ala Gly Thr Tyr Thr Cys Ser Ile His Leu Gln Gly Gln Gln Leu
                325                 330                 335

Asn Ala Thr Val Thr Leu Ala Val Ile Thr Val Thr Pro Lys Ser Phe
            340                 345                 350

Gly Leu Pro Gly Ser Arg Gly Lys Leu Leu Cys Glu Val Thr Pro Ala
        355                 360                 365

Ser Gly Lys Glu Arg Phe Val Trp Arg Pro Leu Asn Asn Leu Ser Arg
    370                 375                 380

Ser Cys Pro Gly Pro Val Leu Glu Ile Gln Glu Ala Arg Leu Leu Ala
385                 390                 395                 400

Glu Arg Trp Gln Cys Gln Leu Tyr Glu Gly Gln Arg Leu Leu Gly Ala
                405                 410                 415

Thr Val Tyr Ala Ala Glu Ser Ser Ser Gly Ala His Ser Ala Arg Arg
            420                 425                 430

Ile Ser Gly Asp Leu Lys Gly Gly His Leu Val Leu Val Leu Ile Leu
        435                 440                 445

Gly Ala Leu Ser Leu Phe Leu Leu Val Ala Gly Ala Phe Gly Phe His
    450                 455                 460

Trp Trp Arg Lys Gln Leu Leu Leu Arg Arg Phe Ser Ala Leu Glu His
465                 470                 475                 480

Gly Ile Gln Pro Phe Pro Ala Gln Arg Lys Ile Glu Glu Leu Glu Arg
                485                 490                 495

Glu Leu Glu Thr Glu Met Gly Gln Glu Pro Glu Pro Glu Pro Glu Pro
            500                 505                 510

Gln Leu Glu Pro Glu Pro Arg Gln Leu
        515                 520

<210> SEQ ID NO 26
<211> LENGTH: 1995
<212> TYPE: DNA
<213> ORGANISM: Homo sapiens

<400> SEQUENCE: 26 acagggtga aggcccagag accagcagaa cggcatccca gccacgacgg ccactttgct      60
ctgtctgctc tccgccacgg ccctgctctg ttccctggga cacccccgcc cccacctcct     120
caggctgcct gatctgccca gctttccagc tttcctctgg attccggcct ctggtcatcc     180
ctccccaccc tctctccaag gccctctcct ggtctcccct cttctagaac cccttcctcc     240
acctccctct ctgcagaact tctcctttac ccccacccc ccaccactgc cccctttcct      300
tttctgacct ccttttggag ggctcagcgc tgcccagacc ataggagaga tgtgggaggc     360
tcagttcctg ggcttgctgt ttctgcagcc gctttgggtg gctccagtga agcctctcca     420
gccaggggct gaggtcccgg tggtgtgggc ccaggagggg gctcctgccc agctcccctg     480
cagccccaca atccccctcc aggatctcag ccttctgcga agagcagggg tcacttggca     540

```
gcatcagcca gacagtggcc cgcccgctgc cgccccggc catccctgg ccccgggccc      600
tcacccggcg gcgccctcct cctgggggcc caggccccgc cgctacacgg tgctgagcgt      660
gggtcccgga ggcctgcgca gcgggaggct gcccctgcag cccgcgtcc agctggatga      720
gcgcggccgg cagcgcgggg acttctcgct atggctgcgc ccagcccggc gcgcggacgc      780
cggcgagtac cgcgccgcgg tgcacctcag ggaccgcgcc ctctcctgcc gcctccgtct      840
gcgcctgggc caggcctcga tgactgccag ccccccagga tctctcagag cctccgactg      900
ggtcattttg aactgctcct tcagccgccc tgaccgccca gcctctgtgc attggttccg      960
gaaccggggc cagggccgag tccctgtccg ggagtccccc catcaccact tagcggaaag     1020
cttcctcttc ctgccccaag tcagccccat ggactctggg ccctggggct gcatcctcac     1080
ctacagagat ggcttcaacg tctccatcat gtataacctc actgttctgg gtctggagcc     1140
cccaactccc ttgacagtgt acgctggagc aggttccagg gtgggctgc cctgccgcct     1200
gcctgctggt gtggggaccc ggtctttcct cactgccaag tggactcctc ctgggggagg     1260
ccctgacctc ctggtgactg agacaatgg cgactttacc cttcgactag aggatgtgag     1320
ccaggcccag gctgggacct acacctgcca tatccatctg caggaacagc agctcaatgc     1380
cactgtcaca ttggcaatca tcacagtgac tcccaaatcc tttgggtcac ctggatccct     1440
ggggaagctg ctttgtgagg tgactccagt atctggacaa gaacgctttg tgtgagctc     1500
tctggacacc ccatcccaga ggagtttctc aggaccttgg ctggaggcac aggaggccca     1560
gctcctttcc cagccttggc aatgccagct gtaccagggg gagaggcttc ttggagcagc     1620
agtgtacttc acagagctgt ctagcccagg tgcccaacgc tctgggagag ccccaggtgc     1680
cctcccagca ggccacctcc tgctgttct catccttggt gtcctttctc tgctcctttt     1740
ggtgactgga gccttttggct ttcaccttg agaagacag tggcgaccaa gacgattttc     1800
tgccttagag caagggattc accctccgca ggctcagagc aagatagagg agctggagca     1860
agaaccggag ccggagccgg agccggaacc ggagcccgag cccgagcccg agccggagca     1920
gctctgacct ggagctgagg cagccagcag atctcagcag cccagtccaa ataaactccc     1980
tgtcagcagc aaaaa                                                      1995

<210> SEQ ID NO 27
<211> LENGTH: 525
<212> TYPE: PRT
<213> ORGANISM: Homo sapiens

<400> SEQUENCE: 27

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110
```

-continued

```
Arg Leu Pro Leu Gln Pro Arg Val Gln Leu Asp Glu Arg Gly Arg Gln
            115                 120                 125
Arg Gly Asp Phe Ser Leu Trp Leu Arg Pro Ala Arg Ala Asp Ala
130             135                 140
Gly Glu Tyr Arg Ala Ala Val His Leu Arg Asp Arg Ala Leu Ser Cys
145                 150                 155                 160
Arg Leu Arg Leu Arg Leu Gly Gln Ala Ser Met Thr Ala Ser Pro Pro
            165                 170                 175
Gly Ser Leu Arg Ala Ser Asp Trp Val Ile Leu Asn Cys Ser Phe Ser
            180                 185                 190
Arg Pro Asp Arg Pro Ala Ser Val His Trp Phe Arg Asn Arg Gly Gln
            195                 200                 205
Gly Arg Val Pro Val Arg Glu Ser Pro His His Leu Ala Glu Ser
            210                 215                 220
Phe Leu Phe Leu Pro Gln Val Ser Pro Met Asp Ser Gly Pro Trp Gly
225                 230                 235                 240
Cys Ile Leu Thr Tyr Arg Asp Gly Phe Asn Val Ser Ile Met Tyr Asn
            245                 250                 255
Leu Thr Val Leu Gly Leu Glu Pro Pro Thr Pro Leu Thr Val Tyr Ala
            260                 265                 270
Gly Ala Gly Ser Arg Val Gly Leu Pro Cys Arg Leu Pro Ala Gly Val
            275                 280                 285
Gly Thr Arg Ser Phe Leu Thr Ala Lys Trp Thr Pro Pro Gly Gly Gly
            290                 295                 300
Pro Asp Leu Leu Val Thr Gly Asp Asn Gly Asp Phe Thr Leu Arg Leu
305                 310                 315                 320
Glu Asp Val Ser Gln Ala Gln Ala Gly Thr Tyr Thr Cys His Ile His
            325                 330                 335
Leu Gln Glu Gln Gln Leu Asn Ala Thr Val Thr Leu Ala Ile Ile Thr
            340                 345                 350
Val Thr Pro Lys Ser Phe Gly Ser Pro Gly Ser Leu Gly Lys Leu Leu
            355                 360                 365
Cys Glu Val Thr Pro Val Ser Gly Gln Glu Arg Phe Val Trp Ser Ser
            370                 375                 380
Leu Asp Thr Pro Ser Gln Arg Ser Phe Ser Gly Pro Trp Leu Glu Ala
385                 390                 395                 400
Gln Glu Ala Gln Leu Leu Ser Gln Pro Trp Gln Cys Gln Leu Tyr Gln
            405                 410                 415
Gly Glu Arg Leu Leu Gly Ala Ala Val Tyr Phe Thr Glu Leu Ser Ser
            420                 425                 430
Pro Gly Ala Gln Arg Ser Gly Arg Ala Pro Gly Ala Leu Pro Ala Gly
            435                 440                 445
His Leu Leu Leu Phe Leu Ile Leu Gly Val Leu Ser Leu Leu Leu Leu
            450                 455                 460
Val Thr Gly Ala Phe Gly Phe His Leu Trp Arg Arg Gln Trp Arg Pro
465                 470                 475                 480
Arg Arg Phe Ser Ala Leu Glu Gln Gly Ile His Pro Pro Gln Ala Gln
            485                 490                 495
Ser Lys Ile Glu Glu Leu Glu Gln Glu Pro Glu Pro Glu Pro Glu Pro
            500                 505                 510
Glu Pro Glu Pro Glu Pro Glu Pro Glu Pro Glu Gln Leu
            515                 520                 525
```

<210> SEQ ID NO 28
<211> LENGTH: 810
<212> TYPE: DNA
<213> ORGANISM: Artificial Sequence
<220> FEATURE:
<223> OTHER INFORMATION: human and mouse

<400> SEQUENCE: 28

| | | | | | |
|---|---|---|---|---|---|
| ttgtgtcttc | agggccaggg | gctgaggtcc | cggtggtgtg | ggcccaggag | ggggctcctg | 60 |
| cccagctccc | ctgcagcccc | acaatccccc | tccaggatct | cagccttctg | cgaagagcag | 120 |
| gggtcacttg | gcagcatcag | ccagacaggt | atgcacccca | aacttgggca | acaggacctc | 180 |
| cgaatccagc | actcaacccc | acaccgtgc | cggtcctctg | tcccctgccc | tgaggtgtca | 240 |
| ctccctctga | agccagtgac | ccagtctccc | tgccctcgct | tgcaccgttc | ctgcccttgc | 300 |
| tctgcaatca | gcgaccctca | cgccagcatc | ccttctctcc | agaagtggat | gcggccagtc | 360 |
| caacagaggg | gtcgggcgtg | agggacggt | tggtggtcaa | gagaactctt | ggggcgggct | 420 |
| ttctcatcct | caacgggtgg | ctgcctgcat | cctcccgggc | ttcctacccc | tggagcttct | 480 |
| caactccatt | ctctttcccg | cccagtggcc | cgcccgctgc | cgcccccggc | catccctgg | 540 |
| cccccggccc | tcacccggcg | gcgccctcct | cctgggggcc | caggccccgc | cgctacacgg | 600 |
| tgctgagcgt | gggtcccgga | ggcctgcgca | gcgggaggct | gccctgcag | ccccgcgtcc | 660 |
| agctggatga | gcgcggccgg | cagcgcgggg | acttctcgct | atggctgcgc | ccagcccggc | 720 |
| gcgcggacgc | cggcgagtac | cgcgccgcgg | tgcacctcag | ggaccgcgcc | ctctcctgcc | 780 |
| gcctccgtct | gcgcctgggc | caggcctcga | | | | 810 |

<210> SEQ ID NO 29
<211> LENGTH: 1578
<212> TYPE: DNA
<213> ORGANISM: Artificial Sequence
<220> FEATURE:
<223> OTHER INFORMATION: human and mouse

<400> SEQUENCE: 29

| | | | | | |
|---|---|---|---|---|---|
| atgagggagg | acctgctcct | tggcttttg | cttctgggac | tgctttggga | agctccagtt | 60 |
| gtgtcttcag | ggccaggggc | tgaggtccg | gtggtgtggg | cccaggaggg | ggctcctgcc | 120 |
| cagctcccct | gcagcccac | aatccccctc | caggatctca | gccttctgcg | aagagcaggg | 180 |
| gtcacttggc | agcatcagcc | agacagtggc | ccgcccgctg | ccgcccccgg | ccatcccctg | 240 |
| gccccggcc | ctcacccggc | ggcgccctcc | tctgggggc | caggccccg | ccgctacacg | 300 |
| gtgctgagcg | tgggtcccgg | aggcctgcgc | agcgggaggc | tgcccctgca | gccccgcgtc | 360 |
| cagctggatg | agcgcggccg | gcagcgcggg | gacttctcgc | tatggctgcg | cccagcccgg | 420 |
| cgcgcggacg | ccggcgagta | ccgcgccgcg | gtgcacctca | gggaccgcgc | cctctcctgc | 480 |
| cgcctccgtc | tgcgcctggg | ccaggcctcg | atgattgcta | gtccctcagg | agtcctcaag | 540 |
| ctgtctgatt | gggtccttt | gaactgctcc | ttcagccgtc | ctgaccgccc | agtctctgtg | 600 |
| cactggttcc | agggccagaa | ccgagtgcct | gtctacaact | caccgcgtca | ttttttagct | 660 |
| gaaactttcc | tgttactgcc | ccaagtcagc | ccctgact | ctgggacctg | ggctgtgtc | 720 |
| ctcacctaca | gagatggctt | caatgtctcc | atcacgtaca | acctcaaggt | tctgggtctg | 780 |
| gagcccgtag | cccctctgac | agtgtacgct | gctgaaggtt | ctagggtgga | gctgccctgt | 840 |
| catttgcccc | caggagtggg | gaccccttct | ttgctcattg | ccaagtggac | tcctcctgga | 900 |
| ggaggtcctg | agctccccgt | ggctggaaag | agtggcaatt | ttaccccttca | ccttgaggct | 960 |

```
gtgggtctgg cacaggctgg gacctacacc tgtagcatcc atctgcaggg acagcagctc      1020
aatgccactg tcacgttggc ggtcatcaca gtgactccca aatccttcgg gttacctggc      1080
tcccggggga agctgttgtg tgaggtaacc ccggcatctg gaaaggaaag atttgtgtgg      1140
cgtcccctga acaatctgtc caggagttgc ccgggccctg tgctggagat tcaggaggcc      1200
aggctccttg ctgagcgatg gcagtgtcag ctgtacgagg ccagaggct tcttggagcg       1260 acagtgtacg ccgcagagtc tagctcaggc gcccacagtg ctaggagaat ctcaggtgac      1320
cttaaaggag gccatctcgt tctcgttctc atccttggtg ccctctccct gttccttttg      1380
gtggccgggg ccttttggctt tcactggtgg agaaaacagt tgctactgag aagattttct     1440
gccttagaac atgggattca gccatttccg gctcagagga agatagagga gctggagcga     1500
gaactggaga cggagatggg acaggagccg gagcccgagc cggagccaca gctggagcca     1560
gagcccaggc agctctga                                                    1578

<210> SEQ ID NO 30
<211> LENGTH: 2032
<212> TYPE: DNA
<213> ORGANISM: Artificial Sequence
<220> FEATURE:
<223> OTHER INFORMATION: human and mouse

<400> SEQUENCE: 30
gggcagtggg gaggagaagc agaaggactg ggtctggagg agcagctcaa gttctagcta      60
gctgcagtgg gtttgcctgc actctgctct gggtcccagc ccgggcctct gatcattatc      120
catcctgctg tctccagtcc ccactcctgg ggcgtcctct tcaccctaca ttctttccct      180
ccgcctcacc tcctccttgt agaacttctc tctctctctc tctctctctc tctctctctc      240
tctctctctc tctgtgtgtg tgtgtgtgtc tgtctgtctg tctgtctctc tctcctccca      300
ggaccttttt ctaacctccc ttggagggct ggggaggccc gggccataga ggagatgagg      360
gaggacctgc tccttggctt tttgcttctg ggactgcttt gggaagctcc agttgtgtct      420
tcagggccag gggctgaggt cccggtggtg tgggcccagg aggggctcc tgcccagctc       480 ccctgcagcc ccacaatccc cctccaggat ctcagccttc tgcgaagagc aggggtcact      540
tggcagcatc agccagacag tggccgcc gctgccgccc ccggccatcc cctggccccc        600
ggccctcacc cggcggcgcc ctcctcctgg gggcccaggc ccgccgcta acgtgctg          660 agcgtgggtc ccggaggcct gcgcagcggg aggctgcccc tgcagccccg cgtccagctg      720
gatgagcgcg gccggcagcg cggggacttc tcgctatggc tgcgcccagc ccggcgcgcg      780
gacgccggcg agtaccgcgc gcggtgcac ctcagggacc gcgccctctc ctgccgcctc        840
cgtctgcgcc tgggccaggc ctcgatgatt gctagtccct caggagtcct caagctgtct      900
gattgggtcc tttttgaactg ctccttcagc cgtcctgacc gcccagtctc tgtgcactgg    960
ttccagggcc agaaccgagt gcctgtctac aactcaccgc gtcatttttt agctgaaact      1020
ttcctgttac tgccccaagt cagccccctg gactctggga cctggggctg tgtcctcacc     1080
tacagagatg gcttcaatgt ctccatcacg tacaacctca aggttctggg tctggagccc     1140
gtagcccctc tgacagtgta cgctgctgaa ggttctaggg tggagctgcc ctgtcatttg     1200 ccccaggag tggggacccc ttctttgctc attgccaagt ggactcctcc tggaggaggt      1260
cctgagctcc ccgtgctgg aaagagtggc aattttaccc ttcaccttga ggctgtgggt     1320
ctggcacagg ctgggaccta cacctgtagc atccatctgc agggacagca gctcaatgcc    1380
```

```
actgtcacgt tggcggtcat acagtgact cccaaatcct tcgggttacc tggctcccgg    1440
gggaagctgt tgtgtgaggt aaccccggca tctggaaagg aaagatttgt gtggcgtccc    1500
ctgaacaatc tgtccaggag ttgcccgggc cctgtgctgg agattcagga ggccaggctc    1560
cttgctgagc gatggcagtg tcagctgtac gagggccaga ggcttcttgg agcgacagtg    1620
tacgccgcag agtctagctc aggcgcccac agtgctagga gaatctcagg tgaccttaaa    1680
ggaggccatc tcgttctcgt tctcatcctt ggtgccctct ccctgttcct tttggtggcc    1740
ggggcctttg gctttcactg gtggagaaaa cagttgctac tgagaagatt ttctgcctta    1800
gaacatggga ttcagccatt tccggctcag aggaagatag aggagctgga gcgagaactg    1860
gagacggaga tgggacagga gccggagccc gagccggagc cacagctgga gccagagccc    1920
aggcagctct gacctggagc cgaggcagcc agcaggtctc agcagctccg cccgcccgcc    1980 cgccccgcccg aataaactcc ctgtcagcag catcaaaaaa aaaaaaaaaa aa    2032
```

<210> SEQ ID NO 31
<211> LENGTH: 525
<212> TYPE: PRT
<213> ORGANISM: Artificial Sequence
<220> FEATURE:
<223> OTHER INFORMATION: human and mouse

<400> SEQUENCE: 31

```
Met Arg Glu Asp Leu Leu Gly Phe Leu Leu Gly Leu Leu Trp
1               5                   10                  15

Glu Ala Pro Val Val Ser Ser Gly Pro Gly Ala Glu Val Pro Val Val
                20                  25                  30

Trp Ala Gln Glu Gly Ala Pro Ala Gln Leu Pro Cys Ser Pro Thr Ile
            35                  40                  45

Pro Leu Gln Asp Leu Ser Leu Leu Arg Arg Ala Gly Val Thr Trp Gln
        50                  55                  60

His Gln Pro Asp Ser Gly Pro Pro Ala Ala Ala Pro Gly His Pro Leu
    65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
                100                 105                 110

Arg Leu Pro Leu Gln Pro Arg Val Gln Leu Asp Glu Arg Gly Arg Gln
            115                 120                 125

Arg Gly Asp Phe Ser Leu Trp Leu Arg Pro Ala Arg Arg Ala Asp Ala
        130                 135                 140

Gly Glu Tyr Arg Ala Ala Val His Leu Arg Asp Arg Ala Leu Ser Cys
    145                 150                 155                 160

Arg Leu Arg Leu Arg Leu Gly Gln Ala Ser Met Ile Ala Ser Pro Ser
                165                 170                 175

Gly Val Leu Lys Leu Ser Asp Trp Val Leu Leu Asn Cys Ser Phe Ser
            180                 185                 190

Arg Pro Asp Arg Pro Val Ser Val His Trp Phe Gln Gly Gln Asn Arg
        195                 200                 205

Val Pro Val Tyr Asn Ser Pro Arg His Phe Leu Ala Glu Thr Phe Leu
    210                 215                 220

Leu Leu Pro Gln Val Ser Pro Leu Asp Ser Gly Thr Trp Gly Cys Val
225                 230                 235                 240

Leu Thr Tyr Arg Asp Gly Phe Asn Val Ser Ile Thr Tyr Asn Leu Lys
                245                 250                 255
```

Val Leu Gly Leu Glu Pro Val Ala Pro Leu Thr Val Tyr Ala Ala Glu
            260                 265                 270

Gly Ser Arg Val Glu Leu Pro Cys His Leu Pro Pro Gly Val Gly Thr
            275                 280                 285

Pro Ser Leu Leu Ile Ala Lys Trp Thr Pro Pro Gly Gly Gly Pro Glu
            290                 295                 300

Leu Pro Val Ala Gly Lys Ser Gly Asn Phe Thr Leu His Leu Glu Ala
305                 310                 315                 320

Val Gly Leu Ala Gln Ala Gly Thr Tyr Thr Cys Ser Ile His Leu Gln
            325                 330                 335

Gly Gln Gln Leu Asn Ala Thr Val Thr Leu Ala Val Ile Thr Val Thr
            340                 345                 350

Pro Lys Ser Phe Gly Leu Pro Gly Ser Arg Gly Lys Leu Leu Cys Glu
            355                 360                 365

Val Thr Pro Ala Ser Gly Lys Glu Arg Phe Val Trp Arg Pro Leu Asn
            370                 375                 380

Asn Leu Ser Arg Ser Cys Pro Gly Pro Val Leu Glu Ile Gln Glu Ala
385                 390                 395                 400

Arg Leu Leu Ala Glu Arg Trp Gln Cys Gln Leu Tyr Glu Gly Gln Arg
            405                 410                 415

Leu Leu Gly Ala Thr Val Tyr Ala Ala Glu Ser Ser Ser Gly Ala His
            420                 425                 430

Ser Ala Arg Arg Ile Ser Gly Asp Leu Lys Gly Gly His Leu Val Leu
            435                 440                 445

Val Leu Ile Leu Gly Ala Leu Ser Leu Phe Leu Leu Val Ala Gly Ala
            450                 455                 460

Phe Gly Phe His Trp Trp Arg Lys Gln Leu Leu Leu Arg Arg Phe Ser
465                 470                 475                 480

Ala Leu Glu His Gly Ile Gln Pro Phe Pro Ala Gln Arg Lys Ile Glu
            485                 490                 495

Glu Leu Glu Arg Glu Leu Glu Thr Glu Met Gly Gln Glu Pro Glu Pro
            500                 505                 510

Glu Pro Glu Pro Gln Leu Glu Pro Glu Pro Arg Gln Leu
            515                 520                 525

<210> SEQ ID NO 32
<211> LENGTH: 869
<212> TYPE: DNA
<213> ORGANISM: Mus musculus

<400> SEQUENCE: 32
gaatcagccc cctcacactt tccactgcga agcgaaaccc cgcgccttgg tctgggggggg      60 cgggcagtgg ggaggagaag cagaaggact gggtctggag gagcagctca agttctagct     120
agctgcagtg ggtttgcctg cactctgctc tgggtcccag cccgggcctc tgatcattat     180
ccatcctgct gtctccagtc cccactcctg gggcgtcctc ttcacccttac attctttccc     240 tccgcctcac ctcctccttg tagaacttct ctctctctct ctctctctct ctctctctct     300
ctctctctct ctctgtgtgt gtgtgtgtgt cgtctgtctg gtctgtctct ctctcctccc     360 aggaccttt tctaacctcc cttggagggc tggggaggcc cgggccatag aggagatgag     420
ggaggacctg ctccttggct ttttgcttct gggactgctt tgggaagctc caggtaaggt     480
ggagagtcca gcagggacct ctatggctgt ctctttagct gtggtgatat ccaatgctt     540 ttgttgaggg gaggggtgtg tgtgtgtgtg tgtgtgtgtg ttttgagaca gggtttcttt     600

```
gtgttgccct ggctgtcctg ggactggctc tgatgaccag gctggccttg aatttatagt    660
gatccacttg cctctgcctc cccagtgctg ggattagagg cgtgcaccat cactttgtat    720
aagggcagat cccaaagctg cctcagcctc ccttcaacag ggaggcatga tgtttctttc    780
ttaggaaagc cagggcattt ctctattctc caatctcttg gctcaatgcc cttggcctct    840
cttttgttcc actagttgtg tcttcaggg                                       869
```

```
<210> SEQ ID NO 33
<211> LENGTH: 52
<212> TYPE: DNA
<213> ORGANISM: Artificial Sequence
<220> FEATURE:
<223> OTHER INFORMATION: PCR primer

<400> SEQUENCE: 33
tttaagaagg agatatacat ggaattcgaa tcagccccct cacactttcc ac             52
```

```
<210> SEQ ID NO 34
<211> LENGTH: 38
<212> TYPE: DNA
<213> ORGANISM: Artificial Sequence
<220> FEATURE:
<223> OTHER INFORMATION: PCR primer

<400> SEQUENCE: 34
cctcagcccc tggccctgaa gacacaacta gtggaaca                             38
```

```
<210> SEQ ID NO 35
<211> LENGTH: 783
<212> TYPE: DNA
<213> ORGANISM: Homo sapiens

<400> SEQUENCE: 35
ccaggggctg aggtcccggt ggtgtgggcc caggaggggg ctcctgccca gctcccctgc     60
agccccacaa tcccctcca ggatctcagc cttctgcgaa gagcaggggt cacttggcag    120
catcagccag acaggtatgc accccaaact tgggcaacag gacctccgaa tccagcactc    180
aaccccacac ccgtgccggt cctctgtccc ctgcctgag gtgtcactcc ctctgaagcc    240
agtgacccag tctccctgcc ctcgcttgca ccgttcctgc ccttgctctg caatcagcga    300
ccctcacgcc agcatccctt ctctccagaa gtggatgcgg ccagtccaac agaggggtcg    360
ggcgtgaggg gacggttggt ggtcaagaga actcttgggg cgggctttct catcctcaac    420
gggtggctgc ctgcatcctc ccgggcttcc taccctgga gcttctcaac tccattctct    480
ttcccgccca gtggcccgcc cgctgccgcc cccggccatc ccctggcccc cggccctcac    540
ccggcggcgc cctcctcctg ggggcccagg ccccgccgct acacggtgct gagcgtgggt    600
cccggaggcc tgcgcagcgg gaggctgccc ctgcagcccc gcgtccagct ggatgagcgc    660
ggccggcagc gcggggactt ctcgctatgg ctgcgcccag cccggcgcgc ggacgccggc    720
gagtaccgcg ccgcggtgca cctcagggac cgcgccctct cctgccgcct ccgtctgcgc    780
ctg                                                                  783
```

```
<210> SEQ ID NO 36
<211> LENGTH: 36
<212> TYPE: DNA
<213> ORGANISM: Artificial Sequence
<220> FEATURE:
<223> OTHER INFORMATION: PCR primer
```

<400> SEQUENCE: 36
gtgtcttcag ggccaggggc tgaggtcccg gtggtg                                  36

<210> SEQ ID NO 37
<211> LENGTH: 35
<212> TYPE: DNA
<213> ORGANISM: Artificial Sequence
<220> FEATURE:
<223> OTHER INFORMATION: PCR primer

<400> SEQUENCE: 37
tcgaggcctg gcccaggcgc agacggaggc ggcag                                   35

<210> SEQ ID NO 38
<211> LENGTH: 1415
<212> TYPE: DNA
<213> ORGANISM: Mus musculus

<400> SEQUENCE: 38
ggccaggcct cgagtaggtg gggccggaca aagggagaga gagggcctgg gaagcagatc        60
cctgcttccc ccggggcagg gagagcaatg gctaggggtt gtgatttaga ccctgtctga      120
ggacctccag aagtgtagaa gaaggggatgg ccccctgatg gcaggatgga aaggcaggtt     180
ggaaagtgcc ccctgaaacg ctcgccttta ggcggggatg aggggctat ggagaaattg       240 tatcacccca cccccttcca actcccttc ccccacctac tgcggagtg ccatcccttg        300 tagaggtaga gatggggaag cacctcttct ttgggggct agagtgattc atctaagata       360
tctgtagctc gtccttaggc caggtctgcc caaagcaag taaagtagag caggaggcc        420 gtggaaaaga gtcccgggtc tcttggagat ccacccataa acatccccag gtttcaagaa     480
ctgacttgga atgagcgggt gtgtggagaa tctgaaagca atgccccatt tctatgagtt     540
tttcagcttg gtttggccgg ctgcgttgag aaagcatttc catctattgg actgattttt     600 ttttttttt ttttaacttt tgcacagtga ttgctagtcc ctcaggagtc ctcaagctgt      660
ctgattgggt cctttgaac tgctccttca gccgtcctga ccgccagtc tctgtgcact       720 ggttccaggg ccagaaccga gtgcctgtct acaactcacc gcgtcatttt ttagctgaaa     780
ctttcctgtt actgccccaa gtcagccccc tggactctgg gacctgggc tgtgtcctca      840 cctacagaga tggcttcaat gtctccatca cgtacaacct caaggttctg ggtaactctt     900
ctaagcagcc ttgaccacaa ccttcctgct caccacctct cctgactcat gcatggaccc    960
ccaaaacttt ctcagctgcg tgtggtctca ctccacatca ctttgtttca gtgtccaaac   1020
cattttctct ctgggcatct tttagctgct gtctctctta cttttattta tttatttgtg    1080
tgtttattta tttattttca ttttagcgtg cgttggtgtt ttgcctgcat agatgtctgt    1140
gtcagggtat tggattccct ggaacttgac ctacagacag tcatgagata ccatatgggt    1200
gctgggaatt gaacccagct cctctggaag gacagccagt gttctaatct gccatctctc   1260
actgtttatc ccttggctgt tcagcctcct gagcctttgg tctcttgctg cctcagtttc    1320
cctagtttct ctgctttgct ctgtttcttt ctgtgttaca gccaaatgcc tccttcccc     1380 ttctgcctta cttccttgat gtctccaccc tctgg                              1415

<210> SEQ ID NO 39
<211> LENGTH: 34
<212> TYPE: DNA
<213> ORGANISM: Artificial Sequence
<220> FEATURE:
<223> OTHER INFORMATION: PCR primer

```
<400> SEQUENCE: 39
cgtctgcgcc tgggccaggc ctcgagtagg tggg                                    34

<210> SEQ ID NO 40
<211> LENGTH: 52
<212> TYPE: DNA
<213> ORGANISM: Artificial Sequence
<220> FEATURE:
<223> OTHER INFORMATION: PCR primer

<400> SEQUENCE: 40
ttgttagcag ccggatctca gggatcccca gagggtggag acatcaagga ag               52

<210> SEQ ID NO 41
<211> LENGTH: 25
<212> TYPE: DNA
<213> ORGANISM: Artificial Sequence
<220> FEATURE:
<223> OTHER INFORMATION: PCR primer

<400> SEQUENCE: 41
agcattcaca cagggtgggg aattt                                              25

<210> SEQ ID NO 42
<211> LENGTH: 20
<212> TYPE: DNA
<213> ORGANISM: Artificial Sequence
<220> FEATURE:
<223> OTHER INFORMATION: PCR primer

<400> SEQUENCE: 42
ggcgtgaggg tcgctgattg                                                    20

<210> SEQ ID NO 43
<211> LENGTH: 24
<212> TYPE: DNA
<213> ORGANISM: Artificial Sequence
<220> FEATURE:
<223> OTHER INFORMATION: PCR primer

<400> SEQUENCE: 43
gacctccgaa tccagcactc aacc                                               24

<210> SEQ ID NO 44
<211> LENGTH: 25
<212> TYPE: DNA
<213> ORGANISM: Artificial Sequence
<220> FEATURE:
<223> OTHER INFORMATION: PCR primer

<400> SEQUENCE: 44
aggagtccac ttggcaatga gcaaa                                              25

<210> SEQ ID NO 45
<211> LENGTH: 22
<212> TYPE: DNA
<213> ORGANISM: Artificial Sequence
<220> FEATURE:
<223> OTHER INFORMATION: PCR primer

<400> SEQUENCE: 45
ggccacttat catcacttgc cc                                                 22

<210> SEQ ID NO 46
```

```
<211> LENGTH: 21
<212> TYPE: DNA
<213> ORGANISM: Artificial Sequence
<220> FEATURE:
<223> OTHER INFORMATION: PCR primer

<400> SEQUENCE: 46
ggtggtaaag gggcctagga g                                            21

<210> SEQ ID NO 47
<211> LENGTH: 21
<212> TYPE: DNA
<213> ORGANISM: Artificial Sequence
<220> FEATURE:
<223> OTHER INFORMATION: PCR primer

<400> SEQUENCE: 47
cagggagagc aatggctagg g                                            21

<210> SEQ ID NO 48
<211> LENGTH: 25
<212> TYPE: DNA
<213> ORGANISM: Artificial Sequence
<220> FEATURE:
<223> OTHER INFORMATION: PCR primer

<400> SEQUENCE: 48
gctgaaaaac tcatagaaat ggggc                                        25

<210> SEQ ID NO 49
<211> LENGTH: 22
<212> TYPE: DNA
<213> ORGANISM: Artificial Sequence
<220> FEATURE:
<223> OTHER INFORMATION: PCR primer

<400> SEQUENCE: 49
gctttgggaa gctccaggta ag                                           22

<210> SEQ ID NO 50
<211> LENGTH: 24
<212> TYPE: DNA
<213> ORGANISM: Artificial Sequence
<220> FEATURE:
<223> OTHER INFORMATION: PCR primer

<400> SEQUENCE: 50
caagggatgg cactcccgca gtag                                         24

<210> SEQ ID NO 51
<211> LENGTH: 25
<212> TYPE: DNA
<213> ORGANISM: Artificial Sequence
<220> FEATURE:
<223> OTHER INFORMATION: PCR primer

<400> SEQUENCE: 51
gcttggacag ggttttatcc attag                                        25

<210> SEQ ID NO 52
<211> LENGTH: 25
<212> TYPE: DNA
<213> ORGANISM: Artificial Sequence
<220> FEATURE:
<223> OTHER INFORMATION: PCR primer

<400> SEQUENCE: 52
```
cttccacatg agcgtggtca gggcc                                              25

<210> SEQ ID NO 53
<211> LENGTH: 25
<212> TYPE: DNA
<213> ORGANISM: Artificial Sequence
<220> FEATURE:
<223> OTHER INFORMATION: PCR primer

<400> SEQUENCE: 53
ccaagggact attttagatg ggcag                                              25

<210> SEQ ID NO 54
<211> LENGTH: 26
<212> TYPE: DNA
<213> ORGANISM: Artificial Sequence
<220> FEATURE:
<223> OTHER INFORMATION: PCR primer

<400> SEQUENCE: 54
gaagctacaa gctcctaggt aggggg                                             26

<210> SEQ ID NO 55
<211> LENGTH: 23
<212> TYPE: DNA
<213> ORGANISM: Artificial Sequence
<220> FEATURE:
<223> OTHER INFORMATION: PCR primer

<400> SEQUENCE: 55
acgggttggc tcaaaccatt aca                                                23

<210> SEQ ID NO 56
<211> LENGTH: 25
<212> TYPE: DNA
<213> ORGANISM: Artificial Sequence
<220> FEATURE:
<223> OTHER INFORMATION: PCR primer

<400> SEQUENCE: 56
acagctgaaa gatgggaagt ggagt                                              25

<210> SEQ ID NO 57
<211> LENGTH: 28
<212> TYPE: DNA
<213> ORGANISM: Artificial Sequence
<220> FEATURE:
<223> OTHER INFORMATION: PCR primer

<400> SEQUENCE: 57
tcaactcatt ccccatcatg taggttgc                                           28

<210> SEQ ID NO 58
<211> LENGTH: 25
<212> TYPE: DNA
<213> ORGANISM: Artificial Sequence
<220> FEATURE:
<223> OTHER INFORMATION: PCR primer

<400> SEQUENCE: 58
ccatcacaca acactgatga ggtcc                                              25

<210> SEQ ID NO 59
<211> LENGTH: 25
<212> TYPE: DNA

-continued

```
<213> ORGANISM: Artificial Sequence
<220> FEATURE:
<223> OTHER INFORMATION: PCR primer

<400> SEQUENCE: 59
cacatcccca aatgcgtttc attgc                                              25
```